(12) United States Patent
Li et al.

(10) Patent No.: US 7,342,108 B2
(45) Date of Patent: Mar. 11, 2008

(54) DE NOVO DNA CYTOSINE METHYLTRANSFERASE GENES, POLYPEPTIDES AND USES THEREOF

(75) Inventors: En Li, Newton, MA (US); Masaki Okano, Malden, MA (US); Shaoping Xie, East Brunswick, NJ (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/720,086

(22) PCT Filed: Jun. 25, 1999

(86) PCT No.: PCT/US99/14373

§ 371 (c)(1),
(2), (4) Date: Jul. 13, 2001

(87) PCT Pub. No.: WO99/67397

PCT Pub. Date: Dec. 29, 1999

(65) Prior Publication Data

US 2006/0084053 A1    Apr. 20, 2006

(51) Int. Cl.
C07H 21/00    (2006.01)
C07H 21/02    (2006.01)
C07H 5/00     (2006.01)
C07H 19/00    (2006.01)
C08B 37/00    (2006.01)
A61K 38/00    (2006.01)

(52) U.S. Cl. .................. 536/23.2; 536/1; 536/18.7; 536/22.1; 536/23.1; 536/23.5; 530/300; 530/350; 435/4; 435/6; 435/7.21; 435/69.1; 435/69.2; 435/183; 435/325

(58) Field of Classification Search .............. 435/4, 435/6, 7.21, 69.1, 69.2, 183, 325; 530/300, 530/350
See application file for complete search history.

(56) References Cited

U.S. PATENT DOCUMENTS 5,578,716 A    11/1996  Szyf et al.
6,183,968 B1 *  2/2001  Bandman et al.
6,492,168 B1 * 12/2002  Kladde et al.

FOREIGN PATENT DOCUMENTS

WO    WO 92/06985      4/1992
WO    WO9514772    *   6/1995

OTHER PUBLICATIONS

GenCore nucleic acid and amino acid database. Sequence comparison between accession No. AF067972 from Gene 1999 paper and Applicants' SEQ ID No. 7 and 8, Feb. 12, 2001.*
Okano et al. Cloning and characterizationof a family of novel mammalian DNA (cytosine-5) methyltransferases. Nature Genetics 19:219 and 220, Jul. 1998.*
GenCore nucleic acid database. Sequence comparison between accession No. AAT21884 from WO document 9514772-A1 and Applicants' SEQ ID No. 1 and 3, Jun. 1, 1995.*
GenCore nucleic acid and amino acid database. Sequence comparison between sequence 47 of U.S. Patent 6,183,968 and Applicants' SEQ ID No. 2 and 5-8, Mar. 27, 1998.*
Lazar et al. Transforming Grouwth Factor alpha: Mutation of Aspartic Acid 47 and Leucine 48 Results in Different Biological Activities. Molecular and Cellular Biology 8(3): 1247-1252, Mar. 1998.*
Editors, Ausubel et al. Current Protocols in Molecular Biology, Supplement 10, vol. 2:16.8.1-16.11.7, 1990.*
Xie et al. Cloning, expression and chromosome locations of the human DNMT3 gene family. Gene 236(1): 87-95, 1999.*
GenCore nucleic acid and amino acid database. Sequence comparison between accession No. AF069625 from nature Genetics 1998 paper and Applicants' SEQ ID No. 5 and 6, Dec. 6, 1999.*
GenCore database. Sequence alignment between SEQ ID No. 3 and Accession No. AF067972 of Xie et al. Gene 236(1): 87-95, 1999, 3 sheets.*
GenCore database. Sequence alignment between SEQ ID No. 2 and Accession No. AF068626 and AF068627 of Okano et al. Nat. Genet. 19(3): 219 and 220, 1998, 8 sheets.*
GenCore DNA sequence alignment between prior art and Applicants' SEQ ID No. 1-4, a total of 18 sheets.*
Okano, M., et al., "Dnmt2 is not required for *de novo* and maintenance methylation of viral DNA in embryonic stem cells," *Nucl. Acids Res.* 26:2536-2540, Oxford University Press (Jun. 1998).
Pradhan, S., et al., "Baculovirus-mediated expression and characterization of the full-length murine DNA methyltransferase," *Nucl. Acids Res.* 25:4666-4673, Oxford University Press (Nov. 1997).
Aoki, A., et al., "Enzymatic properties of *de novo*-type mouse DNA (cytosine-5) methyltransferases," *Nucl. Acids Res.* 29:3506-3512, Oxford University Press (Sep. 2001).
Ariel, M., et al., "Gamete-specific methylation correlates with imprinting of the murine Xist gene," *Nat. Genet.* 9:312-315, Nature Publishing Group (1995).
Bachman, K.E., et al., "Dnmt3a and Dnmt3b Are Transcriptional Repressors That Exhibit Unique Localization Properties to Heterochromatin," *J. Biol. Chem.* 276:32282-32287, The American Society for Biochemistry and Molecular Biology, Inc. (Aug. 2001).
International Search Report for International Application No. PCT/US99/14373, mailed Dec. 10, 1999, European Patent Office, Netherlands.
Baylin, S.B., et al., "Alterations in DNA Methylation: A Fundamental Aspect of Neoplasia," *Adv. Cancer Res.* 72:141-196, Academic Press (Feb. 1998).
Bestor, T., et al., "Cloning and Sequencing of a cDNA Encoding DNA Methyltransferase of Mouse Cells," *J. Mol. Biol.* 203:971-983, Academic Press (1988).

(Continued)

*Primary Examiner*—Alana M. Harris
(74) *Attorney, Agent, or Firm*—Sterne, Kessler, Goldstein & Fox P.L.L.C.

(57) ABSTRACT

De novo DNA cytosine methyltransferase polynucleotides and polypeptides and methods for producing said polypeptides are disclosed. Also disclosed are methods for utilizing de novo DNA cytosine methyltransferase polynucleotides and polypeptides in diagnostic assays, for an in vitro DNA methylation application and therapeutic applications such as the treatment of neoplastic disorders.

35 Claims, 38 Drawing Sheets

OTHER PUBLICATIONS

Bestor, T.H., "Activation of mammalian DNA methyltransferase by cleavage of a Zn binding regulatory domain," *EMBO J. 11*:2611-2617, Oxford University Press (1992).

Brandeis, M., et al., "The ontogeny of allele-specific methylation associated with imprinted genes in the mouse," *EMBO J. 12*:3669-3677, Oxford University Press (1993).

Brockdorff, N., "Convergent themes in X chromosome inactivation and autosomal imprinting," in *Genomic Imrinting*, Reik, W., and Surani, A., eds., Oxford University Press, Oxford, UK, pp. 191-210 (Dec. 1997).

Chaillet, J.R., et al., "Parental-Specific Methylation of an Imprinted Transgene in Established during Gametogenesis and Progressively Changes during Embryogenesis," *Cell 66*:77-83, Cell Press (1991).

Chen, T., et al., "A Novel Dnmt3a Isoform Produced from an Alternative Promoter Localizes to Euchromatin and Its Expression Correlates with Active de Novo Methylation," *J. Biol. Chem. 277*:38746-38754, The American Society for Biochemistry and Molecular Biology, Inc. (Oct. 2002).

Cheng, X., "Structure and function of DNA methyltransferases," *Annu. Rev. Biophys. Biomol. Struct. 24*:293-318, Annual Reviews, Inc. (1995).

Finnegan, E.J., and Dennis, E.S., "Isolation and identification by sequence homology of a putative cytosine methyltransferase from *Arabidopsis thaliana*," *Nucl. Acids Res. 21*:2383-2388, Oxford University Press (1993).

Flynn, J., et al., "Murine DNA Cytosine-$C^5$ Methyltransferase: Pre-Steady- and Steady-State Kinetic Analysis with Regulatory DNA Sequences," *Biochem. 35*:7308-7315, American Chemical Society (1996).

Flynn, J., et al., "DNA Binding Discrimination of the Murine DNA Cytosine-$C^5$ Methyltransferase," *J. Mol. Biol. 279*:101-116, Academic Press (May 1998).

Hata, K., et al., "Dnmt3L cooperates with the Dnmt3 family of de novo DNA methyltransferases to establish maternal imprints in mice," *Develop. 129*:1983-1993, Company of Biologists Ltd. (Apr. 2002).

Jähner, D., and Jaenisch, R., "DNA Methylation in Early Mammalian Development," in *DNA Methylation. Biochemistry and Biological Significance*, Razin, A., eds., Springer-Verlag, New York, NY, pp. 189-219 (1984).

Jentsch, S., et al., "DNA methyltransferases affecting the sequence 5'CCGG," *Nucl. Acids Res. 9*:2753-2759, IRL Press (1981).

Jones, P.A., and Gonzalgo, M.L., "Altered DNA methylation and genome instability: A new pathway to cancer?," *Proc. Natl. Acad. Sci. USA 94*:2103-2105, National Academy of Sciences (Mar. 1997).

Klimašauskas, S., et al., "The sequence specificity domain of cytosine-C5 methylases," *Nucl. Acids Res. 19*:6183-6190, IRL Press at Oxford University Press (1991).

Kumar, S., et al., "The DNA (cytosine-5) methyltransferases," *Nucl. Acids Res. 22*:1-10, Oxford University Press (1994).

Laird, P.W., and Jaenisch, R., "The Role of DNA Methylation in Cancer Genetics and Epigenetics," *Annu. Rev. Genet. 30*:441-464, Annual Reviews Inc. (1996).

Lauster, R., et al., "Cytosine-specific Type II DNA Methyltransferases. A Conserved Enzyme Core with Variable Target-recognizing Domains," *J. Mol. Biol. 206*:305-312, Academic Press Ltd. (1989).

Lei, H., et al., "De novo DNA cytosine methyltransferase activities in mouse embryonic stem cells," *Development 122*:3195-3205, The Company of Biologists Ltd. (1996).

Leonhardt, H., et al., "A Targeting Sequence Directs DNA Methyltransferase to Sites of DNA Replication in Mammalian Nuclei," *Cell 71*:865-873, Cell Press (1992).

Li, E., et al., "Targeted Mutation of the DNA Methyltransferase Gene Results in Embryonic Lethality," *Cell 69*:915-926, Cell Press (1992).

Li, E., "Role of DNA methylation in mammalian development," in *Genomic Imprinting*, Reik, W., and Surani, A. eds., Oxford University Press, Oxford, UK, pp. 1-20 (Dec. 1997).

Malagnac, F., et al., "A Gene Essential for De Novo Methylation and Development in Ascobolus Reveals a Novel Type of Eukaryotic DNA Methyltransferase Structure," *Cell 91*:281-290, Cell Press (Oct. 1997).

Narayan, A., et al., "Hypomethylation of Pericentromeric DNA in Breast Adenocarcinomas," *Int. J. Cancer 77*:833-838, Wiley-Liss, Inc. (Sep. 1998).

Okano, M., et al., "Dnmt2 is not required for *de novo* and maintenance methylation of viral DNA in embryonic stem cells," *Nucl. Acids Res. 26*:2536-2540, Oxford University Press (Jun. 1998).

Okano, M., et al., "DNA Methyltransferases Dnmt3a and Dnmt3b Are Essential for De Novo Methylation and Mammalian Development," *Cell 99*:247-257, Cell Press (Oct. 1999).

Okano, M., and Li, E., "Genetic Analyses of DNA Methyltransferase Genes in Mouse Model System," *J. Nutr. 132*:2462S-2465S, American Institute of Nutrition (Aug. 2002).

Qu, G. -Z., et al., "Satellite DNA hypomethylation vs. overall genomic hypomethylation in ovarian epithelial tumors of different malignant potential," *Mutat. Res. 423*:91-101, Elsevier Science (Jan. 1999).

Razin, A., and Cedar, H., "DNA methylation and embryogensis," in *DNA Methylation: Molecular Biology and Biological Significance*, Jost, J.P., and Saluz, H.P., eds., Birkhäuser Verlag, Basel, Switzerland, pp. 343-357 (1993).

Reid, G.K., et al., "Selective inhibition of DNA methyltransferase enzymes as a novel strategy for cancer treatment," *Curr. Opin. Mol. Ther. 4*:130-137, Current Drugs (Apr. 2002).

Robertson, K.D., et al., "The human DNA methyltransferases (DNMTs) 1, 3a and 3b: coordinate mRNA expression in normal tissues and overexpression in tumors," *Nucl. Acids Res. 27*:2291-2298, Oxford University Press (Jun. 1999).

Stöger, R., et al., "Maternal-Specific Methylation of the Imprinted Mouse *Igf2r* Locus Identifies the Expressed Locus as Carrying the Imprinting Signal," *Cell 73*:61-71, Cell Press (1993).

Szyf, M., et al., "Induction of Myogenic Differentiation by an Expression Vector Encoding the DNA Methyltransferase cDNA Sequence in the Antisense Orientation," *J. Biol. Chem. 267*:12831-12836, The American Society for Biochemistry and Molecular Biology, Inc. (1992).

Szyf, M., and Detich, N., "Regulation of the DNA Methylation Machinery and Its Role in Cellular Transformation," in *Progress in Nucleic Acid Research and Molecular Biology*, Moldave, K., ed., Academic Press, San Diego, CA, pp. 47-79 (Aug. 2001).

Trasler, J.M., et al., "DNA Methyltransferase in Normal and $Dnmt^n/Dnmt^n$ Mouse Embryos," *Dev. Dyn. 206*:239-247, Wiley-Liss, Inc. (1996).

Tremblay, K.D., et al., "A paternal-specific methylation imprint marks the alleles of the mouse *H19* gene," *Nat. Genet. 9*:407-413, Nature Publishing Group (1995).

Tucker, K.L., et al., "Germ-line passage is required for establishment of methylation and expression patterns of imprinted but not of nonimprinted genes," *Genes & Develop. 10*:1008-1020, Cold Spring Harbor Laboratory Press (1996).

Yen, R.-W. C., et al., "Isolation and Characterization of the cDNA encoding human DNA methyltransferase," *Nucl. Acids Res. 20*:2287-2291, Oxford University Press (1992).

Yoder, J.A., and Bestor, T.H., "A candidate mammalian DNA methyltransferase related to pmt1p of fission yeast," *Hum. Mol. Genet. 7*:279-284, Oxford University Press (Feb. 1998).

Zuccotti, M., and Monk, M., "Methylation of the mouse *Xist* gene in sperm and eggs correlates with imprinted *Xist* expression and paternal X-inactivation," *Nat. Genet. 9*:316-320, Nature Publishing Group (1995).

\* cited by examiner

Mouse Dnmt3a DNA sequence

```
   1  GAATTCCGGC CTGCTGCCGG GCCGCCCGAC CCGCCGGGCC ACACGGCAGA
  51  GCCGCCTGAA GCCCAGCGCT GAGGCTGCAC TTTTCCGAGG GCTTGACATC
 101  AGGGTCTATG TTTAAGTCTT AGCTCTTGCT TACAAAGACC ACGGCAATTC
 151  CTTCTCTGAA GCCCTCGCAG CCCCACAGCG CCCTCGCAGC CCCAGCCTGC
 201  CGCCTACTGC CCAGCAATGC CCTCCAGCGG CCCCGGGGAC ACCAGCAGCT
 251  CCTCTCTGGA GCGGGAGGAT GATCGAAAGG AAGGAGAGGA ACAGGAGGAG
 301  AACCGTGGCA AGAAGAGCG CCAGGAGCCC AGCGCCACGG CCCGGAAGGT
 351  GGGGAGGCCT GGCCGGAAGC GCAAGCACCC ACCGGTGGAA AGCAGTGACA
 401  CCCCCAAGGA CCCAGCAGTG ACCACCAAGT CTCAGCCCAT GGCCCAGGAC
 451  TCTGGCCCCT CAGATCTGCT ACCCAATGGA GACTTGGAGA AGCGGAGTGA
 501  ACCCCAACCT GAGGAGGGGA GCCCAGCTGC AGGGCAGAAG GGTGGGGCCC
 551  CAGCTGAAGG AGAGGGAACT GAGACCCCAC CAGAAGCCTC CAGAGCTGTG
 601  GAGAATGGCT GCTGTGTGAC CAAGGAAGGC CGTGGAGCCT CTGCAGGAGA
 651  GGGCAAAGAA CAGAAGCAGA CCAACATCGA ATCCATGAAA ATGGAGGGCT
 701  CCCGGGGCCG ACTGCGAGGT GGCTTGGGCT GGGAGTCCAG CCTCCGTCAG
 751  CGACCCATGC CAAGACTCAC CTTCCAGGCA GGGGACCCCT ACTACATCAG
 801  CAAACGGAAA CGGGATGAGT GGCTGGCACG TTGGAAAAGG GAGGCTGAGA
 851  AGAAAGCCAA GGTAATTGCA GTAATGAATG CTGTGGAAGA GAACCAGGCC
 901  TCTGGAGAGT CTCAGAAGGT GGAGGAGGCC AGCCCTCCTG CTGTGCAGCA
 951  GCCCACGGAC CCTGCTTCTC CGACTGTGGC CACCACCCCT GAGCCAGTAG
1001  GAGGGGATGC TGGGGACAAG AATGCTACCA AAGCAGCCGA CGATGAGCCT
1051  GAGTATGAGG ATGGCCGGGG CTTTGGCATT GGAGAGCTGG TGTGGGGGAA
1101  ACTTCGGGGC TTCTCCTGGT GGCCAGGCCG AATTGTGTCT TGGTGGATGA
```

FIG. 1A-1

```
1151  CAGGCCGGAG CCGAGCAGCT GAAGGCACTC GCTGGGTCAT GTGGTTCGGA

1201  GATGGCAAGT TCTCAGTGGT GTGTGTGGAG AAGCTCATGC CGCTGAGCTC

1251  CTTCTGCAGT GCATTCCACC AGGCCACCTA CAACAAGCAG CCCATGTACC

1301  GCAAAGCCAT CTACGAAGTC CTCCAGGTGG CCAGCAGCCG TGCCGGGAAG

1351  CTGTTTCCAG CTTGCCATGA CAGTGATGAA AGTGACAGTG GCAAGGCTGT

1401  GGAAGTGCAG AACAAGCAGA TGATTGAATG GGCCCTCGGT GGCTTCCAGC

1451  CCTCGGGTCC TAAGGGCCTG GAGCCACCAG AAGAAGAGAA GAATCCTTAC

1501  AAGGAAGTTT ACACCGACAT GTGGGTGGAG CCTGAAGCAG CTGCTTACGC

1551  CCCACCCCCA CCAGCCAAGA AACCCAGAAA GAGCACAACA GAGAAACCTA

1601  AGGTCAAGGA GATCATTGAT GAGCGCACAA GGGAGCGGCT GGTGTATGAG

1651  GTGCGCCAGA AGTGCAGAAA CATCGAGGAC ATTTGTATCT CATGTGGGAG

1701  CCTCAATGTC ACCCTGGAGC ACCCACTCTT CATTGGAGGC ATGTGCCAGA

1751  ACTGTAAGAA CTGCTTCTTG GAGTGTGCTT ACCAGTATGA CGACGATGGG

1801  TACCAGTCCT ATTGCACCAT CTGCTGTGGG GGGCGTGAAG TGCTCATGTG

1851  TGGGAACAAC AACTGCTGCA GGTGCTTTTG TGTCGAGTGT GTGGATCTCT

1901  TGGTGGGGCC AGGAGCTGCT CAGGCAGCCA TTAAGGAAGA CCCCTGGAAC

1951  TGCTACATGT GCGGGCATAA GGGCACCTAT GGGCTGCTGC GAAGACGGGA

2001  AGACTGGCCT TCTCGACTCC AGATGTTCTT TGCCAATAAC CATGACCAGG

2051  AATTTGACCC CCCAAAGGTT TACCCACCTG TGCCAGCTGA GAAGAGGAAG

2101  CCCATCCGCG TGCTGTCTCT CTTTGATGGG ATTGCTACAG GGCTCCTGGT

2151  GCTGAAGGAC CTGGGCATCC AAGTGGACCG CTACATTGCC TCCGAGGTGT

2201  GTGAGGACTC CATCACGGTG GGCATGGTGC GGCACCAGGG AAAGATCATG

2251  TACGTCGGGG ACGTCCGCAG CGTCACACAG AAGCATATCC AGGAGTGGGG

2301  CCCATTCGAC CTGGTGATTG GAGGCAGTCC CTGCAATGAC CTCTCCATTG
```

FIG. 1A-2

2351 TCAACCCTGC CCGCAAGGGA CTTTATGAGG GTACTGGCCG CCTCTTCTTT

2401 GAGTTCTACC GCCTCCTGCA TGATGCGCGG CCCAAGGAGG GAGATGATCG

2451 CCCCTTCTTC TGGCTCTTTG AGAATGTGGT GGCCATGGGC GTTAGTGACA

2501 AGAGGGACAT CTCGCGATTT CTTGAGTCTA ACCCCGTGAT GATTGACGCC

2551 AAAGAAGTGT CTGCTGCACA CAGGGCCCGT TACTTCTGGG GTAACCTTCC

2601 TGGCATGAAC AGGCCTTTGG CATCCACTGT GAATGATAAG CTGGAGCTGC

2651 AAGAGTGTCT GGAGCACGGC AGAATAGCCA AGTTCAGCAA AGTGAGGACC

2701 ATTACCACCA GGTCAAACTC TATAAAGCAG GGCAAAGACC AGCATTTCCC

2751 CGTCTTCATG AACGAGAAGG AGGACATCCT GTGGTGCACT GAAATGGAAA

2801 GGGTGTTTGG CTTCCCCGTC CACTACACAG ACGTCTCCAA CATGAGCCGC

2851 TTGGCGAGGC AGAGACTGCT GGGCCGATCG TGGAGCCTGC CGGTCATCCG

2901 CCACCTCTTC GCTCCGCTGA AGGAATATTT TGCTTGTGTG TAAGGGACAT

2951 GGGGGCAAAC TGAAGTAGTG ATGATAAAAA AGTTAAACAA ACAAACAAAC

3001 AAAAAACAAA ACAAAACAAT AAAACACCAA GAACGAGAGG ACGGAGAAAA

3051 GTTCAGCACC CAGAAGAGAA AAAGGAATTT AAAGCAAACC ACAGAGGAGG

3101 AAAACGCCGG AGGGCTTGGC CTTGCAAAAG GGTTGGACAT CATCTCCTGA

3151 GTTTTCAATG TTAACCTTCA GTCCTATCTA AAAAGCAAAA TAGGCCCCTC

3201 CCCTTCTTCC CCTCCGGTCC TAGGAGGCGA ACTTTTTGTT TTCTACTCTT

3251 TTTCAGAGGG GTTTTCTGTT TGTTTGGGTT TTTGTTTCTT GCTGTGACTG

3301 AAACAAGAGA GTTATTGCAG CAAAATCAGT AACAACAAAA AGTAGAAATG

3351 CCTTGGAGAG GAAAGGGAGA GAGGGAAAAT TCTATAAAAA CTTAAAATAT

3401 TGGTTTTTTT TTTTTTTCCT TTTCTATATA TCTCTTTGGT TGTCTCTAGC

3451 CTGATCAGAT AGGAGCACAA ACAGGAAGAG AATAGAGACC CTCGGAGGCA

3501 GAGTCTCCTC TCCCACCCCC CGAGCAGTCT CAACAGCACC ATTCCTGGTC

FIG. 1A-3

3551 ATGCAAAACA GAACCCAACT AGCAGCAGGG CGCTGAGAGA ACACCACACC

3601 AGACACTTTC TACAGTATTT CAGGTGCCTA CCACACAGGA AACCTTGAAG

3651 AAAACCAGTT TCTAGAAGCC GCTGTTACCT CTTGTTTACA GTTTATATAT

3701 ATATGATAGA TATGAGATAT ATATATATAA AAGGTACTGT TAACTACTGT

3751 ACATCCCGAC TTCATAATGG TGCTTTCAAA ACAGCGAGAT GAGCAAAGAC

3801 ATCAGCTTCC GCCTGGCCCT CTGTGCAAAG GGTTTCAGCC CAGGATGGGG

3851 AGAGGGGAGC AGCTGGAGGG GGTTTTAACA AACTGAAGGA TGACCCATAT

3901 CACCCCCCAC CCCTGCCCCA TGCCTAGCTT CACCTGCCAA AAAGGGGCTC

3951 AGCTGAGGTG GTCGGACCCT GGGGAAGCTG AGTGTGGAAT TTATCCAGAC

4001 TCGCGTGCAA TAACCTTAGA ATATGAATCT AAAATGACTG CCTCAGAAAA

4051 ATGGCTTGAG AAAACATTGT CCCTGATTTT GAATTCGTCA GCCACGTTGA

4101 AGGCCCCTTG TGGATCAGA AATATTCCAG AGTGAGGGAA AGTGACCCGC

4151 CATTAACCCC NCCTGGAGCA AATAAAAAAA CATACAAAAT GT

FIG. 1A-4

Mouse Dnmt3b1 DNA Sequence

```
   1  GAATTCCGGG CGCCGGGGTT AAGCGGCCCA AGTAAACGTA GCGCAGCGAT
  51  CGGCGCCGGA GATTCGCGAA CCCGACACTC CGCGCCGCCC GCCGGCCAGG
 101  ACCCGCGGCG CGATCGCGGC GCCGCGCTAC AGCCAGCCTC ACGACAGGCC
 151  CGCTGAGGCT TGTGCCAGAC CTTGGAAACC TCAGGTATAT ACCTTTCCAG
 201  ACGCGGGATC TCCCCTCCCC CATCCATAGT GCCTTGGGAC CAAATCCAGG
 251  GCCTTCTTTC AGGAAACAAT GAAGGGAGAC AGCAGACATC TGAATGAAGA
 301  AGAGGGTGCC AGCGGGTATG AGGAGTGCAT TATCGTTAAT GGGAACTTCA
 351  GTGACCAGTC CTCAGACACG AAGGATGCTC CCTCACCCCC AGTCTTGGAG
 401  GCAATCTGCA CAGAGCCAGT CTGCACACCA GAGACCAGAG GCCGCAGGTC
 451  AAGCTCCCGG CTGTCTAAGA GGGAGGTCTC CAGCCTTCTG AATTACACGC
 501  AGGACATGAC AGGAGATGGA GACAGAGATG ATGAACTAGA TGATGGGAAT
 551  GGCTCTGATA TTCTAATGCC AAAGCTCACC CGTGAGACCA AGGACACCAG
 601  GACGCGCTCT GAAAGCCCGG CTGTCCGAAC CCGACATAGC AATGGGACCT
 651  CCAGCTTGGA GAGGCAAAGA GCCTCCCCCA GAATCACCCG AGGTCGGCAG
 701  GGCCGCCACC ATGTGCAGGA GTACCCTGTG GAGTTTCCGG CTACCAGGTC
 751  TCGGAGACGT CGAGCATCGT CTTCAGCAAG CACGCCATGG TCATCCCCTG
 801  CCAGCGTCGA CTTCATGGAA GAAGTGACAC CTAAGAGCGT CAGTACCCCA
 851  TCAGTTGACT TGAGCCAGGA TGGAGATCAG GAGGGTATGG ATACCACACA
 901  GGTGGATGCA GACAGCAGAG ATGGAGACAG CACAGAGTAT CAGGATGATA
 951  AAGAGTTTGG AATAGGTGAC CTCGTGTGGG GAAAGATCAA GGGCTTCTCC
1001  TGGTGGCCTG CCATGGTGGT GTCCTGGAAA GCCACCTCCA AGCGACAGGC
```

FIG. 1B-1

```
1051  CATGCCCGGA ATGCGCTGGG TACAGTGGTT TGGTGATGGC AAGTTTTCTG
1101  AGATCTCTGC TGACAAACTG GTGGCTCTGG GGCTGTTCAG CCAGCACTTT
1151  AATCTGGCTA CCTTCAATAA GCTGGTTTCT TATAGGAAGG CCATGTACCA
1201  CACTCTGGAG AAAGCCAGGG TTCGAGCTGG CAAGACCTTC TCCAGCAGTC
1251  CTGGAGAGTC ACTGGAGGAC CAGCTGAAGC CATGCTGGA GTGGGCCCAC
1301  GGTGGCTTCA AGCCTACTGG GATCGAGGGC CTCAAACCCA ACAAGAAGCA
1351  ACCAGTGGTT AATAAGTCGA AGGTGCGTCG TTCAGACAGT AGGAACTTAG
1401  AACCCAGGAG ACGCGAGAAC AAAAGTCGAA GACGCACAAC CAATGACTCT
1451  GCTGCTTCTG AGTCCCCCCC ACCCAAGCGC CTCAAGACAA ATAGCTATGG
1501  CGGGAAGGAC CGAGGGGAGG ATGAGGAGAG CCGAGAACGG ATGGCTTCTG
1551  AAGTCACCAA CAACAAGGGC AATCTGGAAG ACCGCTGTTT GTCCTGTGGA
1601  AAGAAGAACC CTGTGTCCTT CCACCCCCTC TTTGAGGGTG GGCTCTGTCA
1651  GAGTTGCCGG GATCGCTTCC TAGAGCTCTT CTACATGTAT GATGAGGACG
1701  GCTATCAGTC CTACTGCACC GTGTGCTGTG AGGGCCGTGA ACTGCTGCTG
1751  TGCAGTAACA CAAGCTGCTG CAGATGCTTC TGTGTGGAGT GTCTGCAGGT
1801  GCTGGTGGGC GCAGGCACAG CTGAGGATGC CAAGCTGCAG GAACCCTGGA
1851  GCTGCTATAT GTGCCTCCCT CAGCGCTGCC ATGGGGTCCT CCGACGCAGG
1901  AAAGATTGGA ACATGCGCCT GCAAGACTTC TTCACTACTG ATCCTGACCT
1951  GGAAGAATTT GAGCCACCCA AGTTGTACCC AGCAATTCCT GCAGCCAAAA
2001  GGAGGCCCAT TAGAGTCCTG TCTCTGTTTG ATGGAATTGC AACGGGGTAC
2051  TTGGTGCTCA AGGAGTTGGG TATTAAAGTG GAAAAGTACA TTGCCTCCGA
2101  AGTCTGTGCA GAGTCCATCG CTGTGGGAAC TGTTAAGCAT GAAGGCCAGA
2151  TCAAATATGT CAATGACGTC CGGAAAATCA CCAAGAAAAA TATTGAAGAG
2201  TGGGGCCCGT TCGACTTGGT GATTGGTGGA AGCCCATGCA ATGATCTCTC
```

FIG. 1B-2

```
2251  TAACGTCAAT CCTGCCCGCA AAGGTTTATA TGAGGGCACA GGAAGGCTCT
2301  TCTTCGAGTT TTACCACTTG CTGAATTATA CCCGCCCCAA GGAGGGCGAC
2351  AACCGTCCAT TCTTCTGGAT GTTCGAGAAT GTTGTGGCCA TGAAAGTGAA
2401  TGACAAGAAA GACATCTCAA GATTCCTGGC ATGTAACCCA GTGATGATCG
2451  ATGCCATCAA GGTGTCTGCT GCTCACAGGG CCCGGTACTT CTGGGGTAAC
2501  CTACCCGGAA TGAACAGGCC CGTGATGGCT TCAAAGAATG ATAAGCTCGA
2551  GCTGCAGGAC TGCCTGGAGT TCAGTAGGAC AGCAAAGTTA AGAAAGTGC
2601  AGACAATAAC CACCAAGTCG AACTCCATCA GACAGGGCAA AAACCAGCTT
2651  TTCCCTGTAG TCATGAATGG CAAGGACGAC GTTTTGTGGT GCACTGAGCT
2701  CGAAAGGATC TTCGGCTTCC CTGCTCACTA CACGGACGTG TCCAACATGG
2751  GCCGCGGCGC CCGTCAGAAG CTGCTGGGCA GGTCCTGGAG TGTACCGGTC
2801  ATCAGACACC TGTTTGCCCC CTTGAAGGAC TACTTTGCCT GTGAATAGTT
2851  CTACCCAGGA CTGGGGAGCT CTCGGTCAGA GCCAGTGCCC AGAGTCACCC
2901  CTCCCTGAAG GCACCTCACC TGTCCCCTTT TTAGCTCACC TGTGTGGGGC
2951  CTCACATCAC TGTACCTCAG CTTTCTCCTG CTCAGTGGGA GCAGAGCCTC
3001  CTGGCCCTTG CAGGGGAGCC CCGGTGCTCC CTCCGTGTGC ACAGCTCAGA
3051  CCTGGCTGCT TAGAGTAGCC CGGCATGGTG CTCATGTTCT CTTACCCTGA
3101  AACTTTAAAA CTTGAAGTAG GTAGTAAGAT GGCTTTCTTT TACCCTCCTG
3151  AGTTTATCAC TCAGAAGTGA TGGCTAAGAT ACCAAAAAAA CAAACAAAAA
3201  CAGAAACAAA AAACAAAAAA AAACCTCAAC AGCTCTCTTA GTACTCAGGT
3251  TCATGCTGCA AAATCACTTG AGATTTTGTT TTTAAGTAAC CCGTGCTCCA
3301  CATTTGCTGG AGGATGCTAT TGTGAATGTG GGCTCAGATG AGCAAGGTCA
3351  AGGGGCCAAA AAAAATTCCC CCTCTCCCCC CAGGAGTATT TGAAGATGAT
3401  GTTTATGGTT TAAGTCTTCC TGGCACCTTC CCCTTGCTTT GGTACAAGGG
```

FIG. 1B-3

```
3451  CTGAAGTCCT GTTGGTCTTG TAGCATTTCC CAGGATGATG ATGTCAGCAG

3501  GGATGACATC ACCACCTTTA GGGCTTTTCC CTGGCAGGGG CCCATGTGGC

3551  TAGTCCTCAC GAAGACTGGA GTAGAATGTT TGGAGCTCAG GAAGGGTGGG

3601  TGGAGTGGCC CTCTTCCAGG TGTGAGGGAT ACGAAGGAGG AAGCTTAGGG

3651  AAATCCATTC CCCACTCCCT CTTGCCAAAT GAGGGGCCCA GTCCCCAACA

3701  GCTCAGGTCC CCAGAACCCC CTAGTTCCTC ATGAGAAGCT AGGACCAGAA

3751  GCACATCGTT CCCCTTATCT GAGCAGTGTT TGGGAACTA CAGTGAAAAC

3801  CTTCTGGAGA TGTTAAAAGC TTTTACCCC ACGATAGATT GTGTTTTAA

3851  GGGGTGCTTT TTTTAGGGGC ATCACTGGAG ATAAGAAAGC TGCATTTCAG

3901  AAATGCCATC GTAATGGTTT TTAAACACCT TTACCTAAT TACAGGTGCT

3951  ATTTTATAGA AGCAGACAAC ACTTCTTTTT ATGACTCTCA GACTTCTATT

4001  TTCATGTTAC CATTTTTTTT GTAACTCGCA AGGTGTGGGC TTTTGTAACT

4051  TCACAGGTGT GGGGAGAGAC TGCCTTGTTT CAACAGTTTG TCTCCACTGG

4101  TTTCTAATTT TTAGGTGCAA AGATGACAGA TGCCCAGAGT TTACCTTTCT

4151  GGTTGATTAA AGTTGTATTT CTCTAAAAAA AAAAAAAAAA AAAAA
```

FIG. 1B-4

Human DNMT3A DNA Sequence

```
   1                          GCCGCGG CACCAGGGCG CGCAGCCGGG
  28  CCGGCCCGAC CCCACCGGCC ATACGGTGGA GCCATCGAAG CCCCCACCCA
  78  CAGGCTGACA GAGGCACCGT TCACCAGAGG GCTCAACACC GGGATCTATG
 128  TTTAAGTTTT AACTCTCGCC TCCAAAGACC ACGATAATTC CTTCCCCAAA
 178  GCCCAGCAGC CCCCCAGCCC CGCGCAGCCC CAGCCTGCCT CCCGGCGCCC
 228  AGATGCCCGC CATGCCCTCC AGCCGCCCCG GGACACCAG CAGCTCTGCT
 278  GCGGAGCGGG AGGAGGACCG AAAGGACGGA GAGGAGCAGG AGGAGCCGCG
 328  TGGCAAGGAG GAGCGCCAAG AGCCCAGCAC CACGGCACGG AAGGTGGGGC
 378  GGCCTGGGAG GAAGCGCAAG CACCCCCCGG TGGAAAGCGG TGACACGCCA
 428  AAGGACCCTG CGGTGATCTC CAAGTCCCCA TCCATGGCCC AGGACTCAGG
 478  CGCCTCAGAG CTATTACCCA ATGGGGACTT GGAGAAGCGG AGTGAGCCCC
 528  AGCCAGAGGA GGGGAGCCCT GCTGGGGGGC AGAAGGGCGG GGCCCCAGCA
 578  GAGGGAGAGG GTGCAGCTGA GACCCTGCCT GAAGCCTCAA GAGCAGTGGA
 628  AAATGGCTGC TGCACCCCCA AGGAGGGCCG AGGAGCCCCT GCAGAAGCGG
 678  GCAAAGAACA GAAGGAGACC AACATCGAAT CCATGAAAAT GGAGGGCTCC
 728  CGGGGCCGGC TGCGGGGTGG CTTGGGCTGG GAGTCCAGCC TCCGTCAGCG
 778  GCCCATGCCG AGGCTCACCT TCCAGGCGGG GGACCCCTAC TACATCAGCA
 828  AGCGCAAGCG GGACGAGTGG CTGGCACGCT GGAAAAGGGA GGCTGAGAAG
 878  AAAGCCAAGG TCAGTGCAGG AATGAATGCT GTGGAAGAAA ACCAGGGGCC
 928  CGGGGAGTCT CAGAAGCTGG AGGAGGCCAG CCCTCCTGCT GTGCAGCAGC
 978  CCACTGACCC CGCATCCCCC ACTGTGGCTA CCACGCCTGA GCCCGTGGGG
1028  TCCGATGCTG GGACAAGAA TGCCACCAAA GCAGGCGATG ACGAGCCAGA
```

FIG. 1C-1

```
1078  GTACGAGGAC GGCCGGGGCT TTGGCATTGG GGAGCTGGTG TGGGGGAAAC
1128  TGCGGGGCTT CTCCTGGTGG CCAGGCCGCA TTGTGTCTTG GTGGATGACG
1178  GGCCGGAGCC GAGCAGCTGA AGGCACCCGC TGGGTCATGT GGTTCGGAGA
1228  CGGCAAATTC TCAGTGGTGT GTGTTGAGAA GCTGATGCCG CTGAGCTCGT
1278  TTTGCAGTGC GTTCCACCAG GCCACGTACA ACAAGCAGCC CATGTACCGC
1328  AAAGCCATCT ACGAGGTCCT GCAGGTGGCC AGCAGCCGCG CGGGGAAGCT
1378  GTTCCCGGTG TGCCACGACA GCGATGAGAG TGACACTGCC AAGGCCGTCG
1428  AGGTGCAGAA CAAGCCCATG ATTGAATGGG CCCTGGGGGG CTTCCAGCCT
1478  TCTGGCCCTA AGGGCCTGGA GCCACCAGAA GAAGAGAAGA ATCCCTACAA
1528  AGAAGTGTAC ACGGACATGT GGGTGGAACC TGAGGCAGCT GCCTACGCAC
1578  CACCTCCACC AGCCAAAAAG CCCCGGAAGA GCACAGCGGA GAAGCCCAAG
1628  GTCAAGGAGA TTATTGATGA GCGCACAAGA GAGCGGCTGG TGTACGAGGT
1678  GCGGCAGAAG TGCCGGAACA TTGAGGACAT CTGCATCTCC TGTGGGAGCC
1728  TCAATGTTAC CCTGGAACAC CCCCTCTTCG TTGGAGGAAT GTGCCAAAAC
1778  TGCAAGAACT GCTTTCTGGA GTGTGCGTAC CAGTACGACG ACGACGGCTA
1828  CCAGTCCTAC TGCACCATCT GCTGTGGGGG CCGTGAGGTG CTCATGTGCG
1878  GAAACAACAA CTGCTGCAGG TGCTTTTGCG TGGAGTGTGT GGACCTCTTG
1928  GTGGGGCCGG GGGCTGCCCA GGCAGCCATT AAGGAAGACC CCTGGAACTG
1978  CTACATGTGC GGGCACAAGG GTACCTACGG GCTGCTGCGG CGGCGAGAGG
2028  ACTGGCCCTC CCGGCTCCAG ATGTTCTTCG CTAATAACCA CGACCAGGAA
2078  TTTGACCCTC CAAAGGTTTA CCCACCTGTC CCAGCTGAGA AGAGGAAGCC
2128  CATCCGGGTG CTGTCTCTCT TTGATGGAAT CGCTACAGGG CTCCTGGTGC
2178  TGAAGGACTT GGGCATTCAG GTGGACCGCT ACATTGCCTC GGAGGTGTGT
```

```
2228  GAGGACTCCA TCACGGTGGG CATGGTGCGG CACCAGGGGA AGATCATGTA
2278  CGTCGGGAC GTCCGCAGCG TCACACAGAA GCATATCCAG GAGTGGGGCC
2328  CATTCGATCT GGTGATTGGG GGCAGTCCCT GCAATGACCT CTCCATCGTC
2378  AACCCTGCTC GCAAGGGCCT CTACGAGGGC ACTGGCCGGC TCTTCTTTGA
2428  GTTCTACCGC CTCCTGCATG ATGCGCGGCC CAAGGAGGGA GATGATCGCC
2478  CCTTCTTCTG GCTCTTTGAG AATGTGGTGG CCATGGGCGT TAGTGACAAG
2528  AGGGACATCT CGCGATTTCT CGAGTCCAAC CCTGTGATGA TTGATGCCAA
2578  AGAAGTGTCA GCTGCACACA GGGCCCGCTA CTTCTGGGGT AACCTTCCCG
2628  GTATGAACAG GCCGTTGGCA TCCACTGTGA ATGATAAGCT GGAGCTGCAG
2678  GAGTGTCTGG AGCATGGCAG GATAGCCAAG TTCAGCAAAG TGAGGACCAT
2728  TACTACGAGG TCAAACTCCA TAAAGCAGGG CAAAGACCAG CATTTTCCTG
2778  TCTTCATGAA TGAGAAAGAG GACATCTTAT GGTGCACTGA AATGGAAAGG
2828  GTATTTGGTT TCCCAGTCCA CTATACTGAC GTCTCCAACA TGAGCCGCTT
2878  GGCGAGGCAG AGACTGCTGG GCCGGTCATG GAGCGTGCCA GTCATCCGCC
2928  ACCTCTTCGC TCCGCTGAAG GAGTATTTTG CGTGTGTGTA AGGGACATGG
2978  GGGCAAACTG AGGTAGCGAC ACAAAGTTAA ACAAACAAAC AAAAAACACA
3028  AAACATAATA AAACACCAAG AACATGAGGA TGGAGAGAAG TATCAGCACC
3078  CAGAAGAGAA AAAGGAATTT AAAACAAAAA CCACAGAGGC GGAAATACCG
3128  GAGGGCTTTG CCTTGCGAAA AGGGTTGGAC ATCATCTCCT GATTTTTCAA
3178  TGTTATTCTT CAGTCCTATT TAAAAACAAA ACCAAGCTCC CTTCCCTTCC
3228  TCCCCCTTCC CTTTTTTTTC GGTCAGACCT TTTATTTTCT ACTCTTTTCA
3278  GAGGGGTTTT CTGTTTGTTT GGGTTTTGTT TCTTGCTGTG ACTGAAACAA
3328  GAAGGTTATT GCAGCAAAAA TCAGTAACAA AAAATAGTAA CAATACCTTG
3378  CAGAGGAAAG GTGGGAGGAG AGGAAAAAAG GGAAATTTTT AAAGAAATCT
```

3428 ATATATTGGG TTGTTTTTTT TTTTGTTTTT TGTTTTTTTT TTTTGGGTTT

3478 TTTTTTTTTA CTATATATCT TTTTTTTGTT GTCTCTAGCC TGATCAGATA

3528 GGAGCACAAG CAGGGGACGG AAAGAGAGAG ACACTCAGGC GGCAGCATTC

3578 CCTCCCAGCC ACTGAGCTGT CGTGCCAGCA CCATTCCTGG TCACGCAAAA

3628 CAGAACCCAG TTAGCAGCAG GGAGACGAGA ACACCACACA AGACATTTTT

3678 CTACAGTATT TCAGGTGCCT ACCACACAGG AAACCTTGAA GAAAATCAGT

3728 TTCTAGAAGC CGCTGTTACC TCTTGTTTAC AGTTTATATA TATATGATAG

3778 ATATGAGATA TATATATAAA AGGTACTGTT AACTACTGTA CAACCCGACT

3828 TCATAATGGT GCTTTCAAAC AGCGAGATGA GTAAAAACAT CAGCTTCCAC

3878 GTTGCCTTCT GCGCAAAGGG TTTCACCAAG GATGGAGAAA GGGAGACAGC

3928 TTGCAGATGG CGCGTTCTCA CGGTGGGCTC TTCCCCTTGG TTTGTAACGA

3978 AGTGAAGGAG GAGAACTTGG GAGCCAGGTT CTCCCTGCCA AAAGGGGGC

4028 TAGATGAGGT GGTCGGGCCC GTGGACAGCT GAGAGTGGGA TTCATCCAGA

4078 CTCATGCAAT AACCCTTTGA TTGTTTTCTA AAAGGAGACT CCCTCGGCAA

4128 GATGGCAGAG GGTACGGAGT CTTCAGGCCC AGTTTCTCAC TTTAGCCAAT

4178 TCGAGGGCTC CTTGTGGTGG GATCAGAACT AATCCAGAGT GTGGGAAAGT

4228 GACAGTCAAA ACCCCACCTG GAGCAAATAA AAAAACATAC AAAACGTAAA

4278 AAAAAAAAAA AAAAAA

FIG. 1C-4

Human DNMT3B1 DNA Sequence:

```
   1  GGCCGCGAAT TCGGCACGAG CCCTGCACGG CCGCCAGCCG GCCTCCCGCC
  51  AGCCAGCCCC GACCCGCGGC TCCGCCGCCC AGCCGCGCCC CAGCCAGCCC
 101  TGCGGCAGGA AAGCATGAAG GGAGACACCA GGCATCTCAA TGGAGAGGAG
 151  GACGCCGGCG GGAGGGAAGA CTCGATCCTC GTCAACGGGG CCTGCAGCGA
 201  CCAGTCCTCC GACTCGCCCC CAATCCTGGA GGCTATCCGC ACCCCGGAGA
 251  TCAGAGGCCG AAGATCAAGC TCGCGACTCT CCAAGAGGGA GGTGTCCAGT
 301  CTGCTAAGCT ACACACAGGA CTTGACAGGC GATGGCGACG GGAAGATGG
 351  GGATGGCTCT GACACCCCAG TCATGCCAAA GCTCTTCCGG GAAACCAGGA
 401  CTCGTTCAGA AAGCCCAGCT GTCCGAACTC GAAATAACAA CAGTGTCTCC
 451  AGCCGGGAGA GGCACAGGCC TTCCCCACGT TCCACCCGAG GCCGGCAGGG
 501  CCGCAACCAT GTGGACGAGT CCCCCGTGGA GTTCCCGGCT ACCAGGTCCC
 551  TGAGACGGCG GGCAACAGCA TCGGCAGGAA CGCCATGGCC GTCCCCTCCC
 601  AGCTCTTACC TTACCATCGA CCTCACAGAC GACACAGAGG ACACACATGG
 651  GACGCCCCAG AGCAGCAGTA CCCCCTACGC CCGCCTAGCC CAGGACAGCC
 701  AGCAGGGGGG CATGGAGTCC CCGCAGGTGG AGGCAGACAG TGGAGATGGA
 751  GACAGTTCAG AGTATCAGGA TGGGAAGGAG TTTGGAATAG GGACCTCGT
 801  GTGGGGAAAG ATCAAGGGCT CTCCTGGTG GCCCGCCATG GTGGTGTCTT
 851  GGAAGGCCAC CTCCAAGCGA CAGGCTATGT CTGGCATGCC GTGGGTCCAG
 901  TGGTTTGGCG ATGGCAAGTT CTCCGAGGTC TCTGCAGACA AACTGGTGGC
 951  ACTGGGGCTG TTCAGCCAGC ACTTTAATTT GGCCACCTTC AATAAGCTCG
1001  TCTCCTATCG AAAAGCCATG TACCATGCTC TGGAGAAAGC TAGGGTGCGA
1051  GCTGGCAAGA CCTTCCCCAG CAGCCCTGGA GACTCATTGG AGGACCAGCT
1101  GAAGCCCATG TTGGAGTGGG CCCACGGGGG CTTCAAGCCC ACTGGGATCG
1151  AGGGCCTCAA ACCCAACAAC ACGCAACCAG TGGTTAATAA GTCGAAGGTG
```

FIG. 1D-1

```
1201  CGTCGTGCAG GCAGTAGGAA ATTAGAATCA AGGAAATACG AGAACAAGAC
1251  TCGAAGACGC ACAGCTGACG ACTCAGCCAC CTCTGACTAC TGCCCCGCAC
1301  CCAAGCGCCT CAAGACAAAT TGCTATAACA ACGGCAAAGA CCGAGGGGAT
1351  GAAGATCAGA GCCGAGAACA AATGGCTTCA GATGTTGCCA ACAACAAGAG
1401  CAGCCTGGAA GATGGCTGTT TGTCTTGTGG CAGGAAAAAC CCCGTGTCCT
1451  TCCACCCTCT CTTTGAGGGG GGGCTCTGTC AGACATGCCG GGATCGCTTC
1501  CTTGAGCTGT TTTACATGTA TGATGACGAT GGCTATCAGT CTTACTGCAC
1551  TGTGTGCTGC GAGGGCCGAG AGCTGCTGCT TGCAGCAAC ACGAGCTGCT
1601  GCCGGTGTTT CTGTGTGGAG TGCCTGGAGG TGCTGGTGGG CACAGGCACA
1651  GCGGCCGAGG CCAAGCTTCA GGAGCCCTGG AGCTGCTACA TGTGTCTCCC
1701  GCAGCGCTGT CATGGCGTCC TGCGGCGCCG GAAGGACTGG AACGTGCGCC
1751  TGCAGGCCTT CTTCACCAGT GACACGGGGC TTGAATACGA AGCCCCCAAG
1801  CTGTACCCTG CCATTCCCGC AGCCCGAAGG CGGCCCATTC GAGTCCTGTC
1851  ATTGTTTGAT GGCATCGCGA CAGGCTACCT AGTCCTCAAA GAGTTGGGCA
1901  TAAAGGTAGG AAAGTACGTC GCTTCTGAAG TGTGTGAGGA GTCCATTGCT
1951  GTTGGAACCG TGAAGCACGA GGGGAATATC AAATACGTGA ACGACGTGAG
2001  GAACATCACA AAGAAAAATA TTGAAGAATG GGGCCCATTT GACTTGGTGA
2051  TTGGCGGAAG CCCATGCAAC GATCTCTCAA ATGTGAATCC AGCCAGGAAA
2101  GGCCTGTATG AGGGTACAGG CCGGCTCTTC TTCGAATTTT ACCACCTGCT
2151  GAATTACTCA CGCCCCAAGG AGGGTGATGA CCGGCCGTTC TTCTGGATGT
2201  TTGAGAATGT TGTAGCCATG AAGGTTGGCG ACAAGAGGGA CATCTCACGG
2251  TTCCTGGAGT GTAATCCAGT GATGATTGAT GCCATCAAAG TTTCTGCTGC
2301  TCACAGGGCC CGATACTTCT GGGGCAACCT ACCCGGGATG AACAGGCCCG
2351  TGATAGCATC AAAGAATGAT AAACTCGAGC TGCAGGACTG CTTGGAATAC
2401  AATAGGATAG CCAAGTTAAA GAAAGTACAG ACAATAACCA CCAAGTCGAA
```

FIG. 1D-2

2451 CTCGATCAAA CAGGGGAAAA ACCAACTTTT CCCTGTTGTC ATGAATGGCA

2501 AAGAAGATGT TTTGTGGTGC ACTGAGCTCG AAAGGATCTT TGGCTTTCCT

2551 GTGCACTACA CAGACGTGTC CAACATGGGC CGTGGTGCCC GCCAGAAGCT

2601 GCTGGGAAGG TCCTGGAGCG TGCCTGTCAT CCGACACCTC TTCGCCCCTC

2651 TGAAGGACTA CTTTGCATGT GAATAGTTCC AGCCAGGCCC CAAGCCCACT

2701 GGGGTGTGTG GCAGAGCCAG GACCCAGGAG GTGTGATTCC TGAAGGCATC

2751 CCCAGGCCCT GCTCTTCCTC AGCTGTGTGG GTCATACCGT GTACCTCAGT

2801 TCCCTCTTGC TCAGTGGGGG CAGAGCCACC TGACTCTTGC AGGGGTAGCC

2851 TGAGGTGCCG CCTCCTTGTG CACAAATCAG ACCTGGCTGC TTGGAGCAGC

2901 CTAACACGGT GCTCATTTTT TCTTCTCCTA AAACTTTAAA ACTTGAAGTA

2951 GGTAGCAACG TGGCTTTTTT TTTTTCCCTT CCTGGGTCTA CCACTCAGAG

3001 AAACAATGGC TAAGATACCA AAACCACAGT GCCGACAGCT CTCCAATACT

3051 CAGGTTAATG CTGAAAAATC ATCCAAGACA GTTATTGCAA GAGTTTAATT

3101 TTTGAAAACT GGGTACTGCT ATGTGTTTAC AGACGTGTGC AGTTGTAGGC

3151 ATGTAGCTAC AGGACATTTT TAAGGGCCCA GGATCGTTTT TTCCCAGGGC

3201 AAGCAGAAGA GAAAATGTTG TATATGTCTT TTACCCGGCA CATTCCCCTT

3251 GCCTAAATAC AAGGGCTGGA GTCTGCACGG GACCTATTAG AGTATTTCC

3301 ACAATGATGA TGATTTCAGC AGGGATGACG TCATCATCAC ATTCAGGGCT

3351 ATTTTTTCCC CCACAAACCC AAGGGCAGGG GCCACTCTTA GCTAAATCCC

3401 TCCCCGTGAC TGCAATAGAA CCCTCTGGGG AGCTCAGGAA GGGGTGTGCT

3451 GAGTTCTATA ATATAAGCTG CCATATATTT TGTAGACAAG TATGGCTCCT

3501 CCATATCTCC CTCTTCCCTA GGAGAGGAGT GTGAAGCAAG GAGCTTAGAT

3551 AAGACACCCC CTCAAACCCA TTCCCTCTCC AGGAGACCTA CCCTCCACAG

3601 GCACAGGTCC CCAGATGAGA AGTCTGCTAC CCTCATTTCT CATCTTTTTA

3651 CTAAACTCAG AGGCAGTGAC AGCAGTCAGG GACAGACATA CATTTCTCAT

FIG. 1D-3

3701 ACCTTCCCCA CATCTGAGAG ATGACAGGGA AAACTGCAAA GCTCGGTGCT

3751 CCCTTTGGAG ATTTTTTAAT CCTTTTTTAT TCCATAAGAA GTCGTTTTTA

3801 GGGAGAACGG GAATTCAGAC AAGCTGCATT TCAGAAATGC TGTCATAATG

3851 GTTTTTAACA CCTTTTACTC TTCTTACTGG TGCTATTTTG TAGAATAAGG

3901 AACAACGTTG ACAAGTTTTG TGGGGCTTTT TATACACTTT TTAAAATCTC

3951 AAACTTCTAT TTTTATGTTT AACGTTTTCA TTAAAATTTT TTTGTAACTG

4001 GAGCCACGAC GTAACAAATA TGGGGAAAAA ACTGTGCCTT GTTTCAACAG

4051 TTTTTGCTAA TTTTTAGGCT GAAAGATGAC GGATGCCTAG AGTTTACCTT

4101 ATGTTTAATT AAAATCAGTA TTTGTCTAAA AAAAAAAAAA AAAAA

FIG. 1D-4

Mouse Dnmt3a Protein

```
  1  MPSSGPGDTS SSSLEREDDR KEGEEQEENR GKEERQEPSA TARKVGRPGR
 51  KRKHPPVESS DTPKDPAVTT KSQPMAQDSG PSDLLPNGDL EKRSEPQPEE
101  GSPAAGQKGG APAEGEGTET PPEASRAVEN GCCVTKEGRG ASAGEGKEQK
151  QTNIESMKME GSRGRLRGGL GWESSLRQRP MPRLTFQAGD PYYISKRKRD
201  EWLARWKREA EKKAKVIAVM NAVEENQASG ESQKVEEASP PAVQQPTDPA
251  SPTVATTPEP VGGDAGDKNA TKAADDEPEY EDGRGFGIGE LVWGKLRGFS
301  WWPGRIVSWW MTGRSRAAEG TRWVMWFGDG KFSVVCVEKL MPLSSFCSAF
351  HQATYNKQPM YRKAIYEVLQ VASSRAGKLF PACHDSDESD SGKAVEVQNK
401  QMIEWALGGF QPSGPKGLEP PEEEKNPYKE VYTDMWVEPE AAAYAPPPPA
451  KKPRKSTTEK PKVKEIIDER TRERLVYEVR QKCRNIEDIC ISCGSLNVTL
501  EHPLFIGGMC QNCKNCFLEC AYQYDDDGYQ SYCTICCGGR EVLMCGNNNC
551  CRCFCVECVD LLVGPGAAQA AIKEDPWNCY MCGHKGTYGL LRRREDWPSR
601  LQMFFANNHD QEFDPPKVYP PVPAEKRKPI RVLSLFDGIA TGLLVLKDLG
651  IQVDRYIASE VCEDSITVGM VRHQGKIMYV GDVRSVTQKH IQEWGPFDLV
701  IGGSPCNDLS IVNPARKGLY EGTGRLFFEF YRLLHDARPK EGDDRPFFWL
751  FENVVAMGVS DKRDISRFLE SNPVMIDAKE VSAAHRARYF WGNLPGMNRP
801  LASTVNDKLE LQECLEHGRI AKFSKVRTIT TRSNSIKQGK DQHFPVFMNE
851  KEDILWCTEM ERVFGFPVHY TDVSNMSRLA RQRLLGRSWS VPVIRHLFAP
901  LKEYFACV*
```

FIG. 2A

Mouse Dnmt3b1 Protein

```
  1  MKGDSRHLNE EEGASGYEEC IIVNGNFSDQ SSDTKDAPSP PVLEAICTEP
 51  VCTPETRGRR SSSRLSKREV SSLLNYTQDM TGDGDRDDEV DDGNGSDILM
101  PKLTRETKDT RTRSESPAVR TRHSNGTSSL ERQRASPRIT RGRQGRHHVQ
151  EYPVEFPATR SRRRRASSSA STPWSSPASV DFMEEVTPKS VSTPSVDLSQ
201  DGDQEGMDTT QVDAESRDGD STEYQDDKEF GIGDLVWGKI KGFSWWPAMV
251  VSWKATSKRQ AMPGMRWVQW FGDGKFSEIS ADKLVALGLF SQHFNLATFN
301  KLVSYRKAMY HTLEKARVRA GKTFSSSPGE SLEDQLKPML EWAHGGFKPT
351  GIEGLKPNKK QPVVNKSKVR RSDSRNLEPR RRENKSRRRT TNDSAASESP
401  PPKRLKTNSY GGKDRGEDEE SRERMASEVT NNKGNLEDRC LSCGKKNPVS
451  FHPLFEGGLC QSCRDRFLEL FYMYDEDGYQ SYCTVCCEGR ELLLCSNTSC
501  CRCFCVECLE VLVGAGTAED AKLQEPWSCY MCLPQRCHGV LRRRKDWNMR
551  LQDFFTTDPD LEEFEPPKLY PAIPAAKRRP IRVLSLFDGI ATGYLVLKEL
601  GIKVEKYIAS EVCAESIAVG TVKHEGQIKY VNDVRKITKK NIEEWGPFDL
651  VIGGSPCNDL SNVNPARKGL YEGTGRLFFE FYHLLNYTRP KEGDNRPFFW
701  MFENVVAMKV NDKKDISRFL ACNPVMIDAI KVSAAHRARY FWGNLPGMNR
751  PVMASKNDKL ELQDCLEFSR TAKLKKVQTI TTKSNSIRQG KNQLFPVVMN
801  GKDDVLWCTE LERIFGFPAH YTDVSNMGRG ARQKLLGRSW SVPVIRHLFA
851  PLKDYFACE*
```

FIG. 2B

Human DNMT3A Protein

```
  1  MPAMPSSGPG DTSSSAAERE EDRKDGEEQE EPRGKEERQE PSTTARKVGR
 51  PGRKRKHPPV ESGDTPKDPA VISKSPSMAQ DSGASELLPN GDLEKRSEPQ
101  PEEGSPAGGQ KGGAPAEGEG AAETLPEASR AVENGCCTPK EGRGAPAEAG
151  KEQKETNIES MKMEGSRGRL RGGLGWESSL RQRPMPRLTF QAGDPYYISK
201  RKRDEWLARW KREAEKKAKV IAGMNAVEEN QGPGESQKVE EASPPAVQQP
251  TDPASPTVAT TPEPVGSDAG DKNATKAGDD EPEYEDGRGF GIGELVWGKL
301  RGFSWWPGRI VSWWMTGRSR AAEGTRWVMW FGDGKFSVVC VEKLMPLSSF
351  CSAFHQATYN KQPMYRKAIY EVLQVASSRA GKLFPVCHDS DESDTAKAVE
401  VQNKPMIEWA LGGFQPSGPK GLEPPEEEKN PYKEVYTDMW VEPEAAAYAP
451  PPPAKKPRKS TAEKPKVKEI IDERTRERLV YEVRQKCRNI EDICISCGSL
501  NVTLEHPLFV GGMCQNCKNC FLECAYQYDD DGYQSYCTIC CGGREVLMCG
551  NNNCCRCFCV ECVDLLVGPG AAQAAIKEDP WNCYMCGHKG TYGLLRRRED
601  WPSRLQMFFA NNHDQEFDPP KVYPPVPAEK RKPIRVLSLF DGIATGLLVL
651  KDLGIQVDRY IASEVCEDSI TVGMVRHQGK IMYVGDVRSV TQKHIQEWGP
701  FDLVIGGSPC NDLSIVNPAR KGLYEGTGRL FFEFYRLLHD ARPKEGDDRP
751  FFWLFENVVA MGVSDKRDIS RFLESNPVMI DAKEVSAAHR ARYFWGNLPG
801  MNRPLASTVN DKLELQECLE HGRIAKFSKV RTITTRSNSI KQGKDQHFPV
851  FMNEKEDILW CTEMERVFGF PVHYTDVSNM SRLARQRLLG RSWSVPVIRH
901  LFAPLKEYFA CV*
```

FIG. 2C

Human DNMT3B1 Protein

```
  1  MKGDTRHLNG EEDAGGREDS ILVNGACSDQ SSDSPPILEA IRTPEIRGRR
 51  SSSRLSKREV SSLLSYTQDL TGDGDGEDGD GSDTPVMPKL FRETRTRSES
101  PAVRTRNNNS VSSRERHRPS PRSTRGRQGR NHVDESPVEF PATRSLRRRA
151  TASAGTPWPS PPSSYLTIDL TDDTEDTHGT PQSSSTPYAR LAQDSQQGGM
201  ESPQVEADSG DGDSSEYQDG KEFGIGDLVW GKIKGFSWWP AMVVSWKATS
251  KRQAMSGMRW VQWFGDGKFS EVSADKLVAL GLFSQHFNLA TFNKLVSYRK
301  AMYHALEKAR VRAGKTFPSS PGDSLEDQLK PMLEWAHGGF KPTGIEGLKP
351  NNTQPVVNKS KVRRAGSRKL ESRKYENKTR RRTADDSATS DYCPAPKRLK
401  TNCYNNGKDR GDEDQSREQM ASDVANNKSS LEDGCLSCGR KNPVSFHPLF
451  EGGLCQTCRD RFLELFYMYD DDGYQSYCTV CCEGRELLLC SNTSCCRCFC
501  VECLEVLVGT GTAAEAKLQE PWSCYMCLPQ RCHGVLRRRK DWNVRLQAFF
551  TSDTGLEYEA PKLYPAIPAA RRRPIRVLSL FDGIATGYLV LKELGIKVGK
601  YVASEVCEES IAVGTVKHEG NIKYVNDVRN ITKKNIEEWG PFDLVIGGSP
651  CNDLSNVNPA RKGLYEGTGR LFFEFYHLLN YSRPKEGDDR PFFWMFENVV
701  AMKVGDKRDI SRFLECNPVM IDAIKVSAAH RARYFWGNLP GMNRPVIASK
751  NDKLELQDCL EYNRIAKLKK VQTITTKSNS IKQGKNQLFP VVMNGKEDVL
801  WCTELERIFG FPVHYTDVSN MGRGARQKLL GRSWSVPVIR HLFAPLKDYF
851  ACE*
```

FIG. 2D

```
Dnmt3a    1 MPSSGPGDTSSSSLEREDDRKEGEEQEENRGKEERQEPSATARKVGRPGR  50

Dnmt3a   51 KRKHPPVESSDTPKDPAVTTKSQPMAQDSGPSD....LLPNGDLEKRSEP  96
              .  |. :  ::  ||     ::  ||.    .|
Dnmt3b    1 ...............MKGDSRHLNEEEGASGYEECIIVNGNFSDQSSD  33

Dnmt3a   97 QPEEGSP....AAGQKGGAPAEGEGTETPPEAS.RAVENGCCVTKE...GR 139
             :  ||    |   .    ||  .    |||  .    |.:   |
Dnmt3b   34 TKDAPSPPVLEAICTEPVCTPETRGRRSSSRLSKREVSSLLNYTQDMTGD  83

Dnmt3a  140 G.....ASAGEG......KEQKQTNIESMKMEGSRGRLRGGLGWESSLRQ 178
            |     ||      |    ::|   : |   | | | ||
Dnmt3b   84 GDRDDEVDDGNGSDILMPKLTRETKDTRTRSESPAVRTRHSNGTSSLERQ 133

Dnmt3a  179 RPMPRLTFQAGDPYYISKRKRDEWLARWKREAEKKAKVIAVMNAVEENQA 228
             |  ||:|    :::     |:   .      ::  :  .   .   .|
Dnmt3b  134 RASPRITRGRQGRHHV.....QEYPVEFPATRSRRRRASSSASTPWSSPA 178

Dnmt3a  229 SGESQKVEEASPPAVQQPTDPASPTVATTPEPVGGDAGDKNATKAADDEP 278
            |:   .||  .|  .|  |      |  ..  ||  .|       |
Dnmt3b  179 SVDF..MEEVTPKSVSTP....SVDLSQDGDQEGMDTTQVDAESRDGDST 222

Dnmt3a  279 EYEDGRGFGIGELVWGKLRGFSWWPGRIVSWWMTGRSRAAEGTRWVMWFG 328
            ||:|  :  ||||:||||||::||||||  :|||   | :  .| |||  |||
Dnmt3b  223 EYQDDKEFGIGDLVWGKIKGFSWWPAMVVSWKATSKRQAMPGMRWVQWFG 272

Dnmt3a  329 DGKFSVVCVEKLMPLSSFCSAFHQATYNKQPMYRKAIYEVLQVASSRAGK 378
            |||||  :  :||.   |    | |- ||:||    ||||.|   |:   |   ||||
Dnmt3b  273 DGKFSEISADKLVALGLFSQHFNLATFNKLVSYRKAMYHTLEKARVRAGK 322

Dnmt3a  379 LFPACHDSDESDSGKAVEVQNKQMIEWALGGFQPSGPKGLEPPEEEK..N 426
            |          |  |...| | |  |:|||   |||.|.| .||.|  ..:   |
Dnmt3b  323 TF.......SSSPGESLEDQLKPMLEWAHGGFKPTGIEGLKPNKKQPVVN 365

Dnmt3a  427 PYKEVYTDMW.VEP............EAAAYAPPPPAKKPRKSTTEKPK 462
            |   .|  .||                  :.||    |||  :    |   |:
Dnmt3b  366 KSKVRRSDSRNLEPRRRENKSRRRTTNDSAASESPPPKRLKTNSYGGKDR 415
```

FIG.3A-1

```
Dnmt3a  463  VKEIIDERTRERLVYEVRQKCRNIEDICISCGSLNVTLEHPFFIGGMCQN  512
              | |  |||:  ||       |:|| |:|||  |    || | ||:||·
Dnmt3b  416  GE...DEESRERMASEVTNNKGNLEDRCLSCGKKNPVSFHPLFEGGLCQS  462

Dnmt3a  513  CKNCFLECAYQYDDDGYQSYCTICCGGREVLMCGNNNCCRCFCVECVDLL  562
             |:· |||  |  ||:|||||||||:|| |||·|:| | ·|||||||||·:·|
Dnmt3b  463  CRDRFLELFYMYDEDGYQSYCTVCCEGRELLLCSNTSCCRCFCVECLEVL  512

Dnmt3a  563  VGPGAAQAAIKEDPWNCYMCGHKGTYGLLRRREDWPSRLQMFFANNHD.Q  611
             || |  |: |   ::||·||||        .:|·||||·|| ||| ||  · | :
Dnmt3b  513  VGAGTAEDAKLQEPWSCYMCLPQRCHGVLRRRKDWNMRLQDFFTTDPDLE  562

Dnmt3a  612  EFDPPKVYPPVPAEKRKPIRVLSLFDGIATGLLVLKDLGIQVDRYIASEV  661
             ||:|||·|| :|| ||:||||||||||||||| ||||:|||·|·::|||||
Dnmt3b  563  EFEPPKLYPAIPAAKRRPIRVLSLFDGIATGYLVLKELGIKVEKYIASEV  612

Dnmt3a  662  CEDSITVGMVRHQGKIMYVGDVRSVTQKHIQEWGPFDLVIGGSPCNDLSI  711
             | :|| || |:|:|·| || ||| :|·|·|:|||||||||||||||||||||
Dnmt3b  613  CAESIAVGTVKHEGQIKYVNDVRKITKKNIEEWGPFDLVIGGSPCNDLSN  662

Dnmt3a  712  VNPARKGLYEGTGRLFFEFYRLLHDARPKEGDDRPFFWLFENVVAMGVSD  761
             |||||||||||||||||||||·  ||||||·||||:|||||| |·|
Dnmt3b  663  VNPARKGLYEGTGRLFFEFYHLLNYTRPKEGDNRPFFWMFENVVAMKVND  712

Dnmt3a  762  KRDISRFLESNPVMIDAKEVSAAHRARYFWGNLPGMNRPLASTVNDKLEL  811
             |:|||||   ||||||| ·||||||||||||||||||||·  ||||||
Dnmt3b  713  KKDISRFLACNPVMIDAIKVSAAHRARYFWGNLPGMNRPVMASKNDKLEL  762

Dnmt3a  812  QECLEHGRIAKFSKVRTITTRSNSIKQGKDQHFPVFMNEKEDILWCTEME  861
             |:|||  | ||  ||·||||:||||:|||·|  || || |:|:|||||:|
Dnmt3b  763  QDCLEFSRTAKLKKVQTITTKSNSIRQGKNQLFPVVMNGKDDVLWCTELE  812

Dnmt3a  862  RVFGFPVHYTDVSNMSRLARQRLLGRSWSVPVIRHLFAPLKEYFACV*   909
             |:||||·||||||||·|||:|||||||||||||||||||||||:|||| |
Dnmt3b  813  RIFGFPAHYTDVSNMGRGARQKLLGRSWSVPVIRHLFAPLKDYFACE*   860
```

FIG.3A-2

```
DNMT3A    1  MPAMPSSGPGDTSSSAAEREEDRKDGEEQEEPRGKEERQEPSTTARKVGR

DNMT3A   51  PGRKRKHPPVESGDTPKDPAVISKSPSMAQDSGASELLPNGDLEKRSEPQ
                  |           |   | |.        :.  |:
DNMT3B    1  ...............MKGDTRHLNGEEDAGGREDSILVNGACSDQSSDSP

DNMT3A  101  PEEGSPAGGQKGGAPAEGEGAAETLPEASRAVENGCCTPKEGRGAPAEAG
             | .:  | |   .  .       :.         |   .:
DNMT3B   36  PILEAIRTPEIRGGWASSRLSKREVSSLLSYTQDLTGDGDGEDGDGSDTP

DNMT3A  151  KEQKETNIESMKMEGSRGRLRGGLGWESSLRQRPMPRLTFQAGDPYYISK
              :  |    ||     |    |  || ||  |              ::.
DNMT3B   86  VMPKLFRETRTRSESPAVRTRNNNSVSSRERHRPSPRSTRGRQGRNHVDE

DNMT3A  201  RKRDEWLARWKREAEKKAKVIAGMNAVEENQGPGESQKVEEASPPAVQQP
             :  | |  .   .         .|:          |
DNMT3B  136  SPVEFPATRSLRRRATASAGTPWPSPPSSYLTIDLTDDTEDTH..GTPQS

DNMT3A  251  TDPASPTVATTPEPVGSDAGDKNATKAGDDEPEYEDGRGFGIGELVWGKL
             .    .|  : |:.     |   |   ||:||:  ||||:|||||:
DNMT3B  184  SSTPYARLAQDSQQGGMESPQVEADSGDGDSSEYQDGKEFGIGDLVWGKI

DNMT3A  301  RGFSWWPGRIVSWWMTGRSRAAEGTRWVMWFGDGKFSVVCVEKLMPLSSF
             :||||||  :|||   |  .|   |  ||| |||||||| |  :||. | |
DNMT3B  234  KGFSWWPAMVVSWKATSKRQAMSGMRWVQWFGDGKFSEVSADKLVALGLF

DNMT3A  351  CSAFHQATYNKQPMYRKAIYEVLQVASSRAGKLFPVCHDSDESDTAKAVE
             |. ||:||   ||||.|  |: |    ||||  ||            ..|
DNMT3B  284  SQHFNLATFNKLVSYRKAMYHALEKARVRAGKTFP.......SSPGDSLE

DNMT3A  401  VQNKPMIEWALGGFQPSGPKGLEP....PEEEKNPYKEVYTDMWVE....
             | |||:|||  |||. | .||.|     |   |.  :
DNMT3B  327  DQLKPMLEWAHGGFKPTGIEGLKPNNTQPVVNKSKVRRAGSRKLESRKYE

DNMT3A  443  .......PEAAAYAPPPPAKKPRKSTAEKPKVKEIIDERTRERLVYEVRQ
                :|.  ||| |.         :::..||.:  :|
DNMT3B  377  NKTRRRTADDSATSDYCPAPKRLKTNCYNNGKDRGDEDQSREQMASDVAN
```

FIG.3B-1

```
DNMT3A  486  KCRNIEDICISCGSLNVTLEHPLFVGGMCQNCKNCFLECAYQYDDDGYQS
              .:|| |:|||    |||| ||:|| |:. |||   | ||||||||
DNMT3B  427  NKSSLEDGCLSCGRKNPVSFHPLFEGGLCQTCRDRFLELFYMYDDDGYQS

DNMT3A  536  YCTICCGGREVLMCGNNNCCRCFCVECVDLLVGPGAAQAAIKEDPWNCYM
             |||:|| |||.|:| | .||||||||.:.||| | |   | ::||.|||
DNMT3B  477  YCTVCCEGRELLLCSNTSCCRCFCVECLEVLVGTGTAAEAKLQEPWSCYM

DNMT3A  586  CGHKGTYGLLRRREDWPSRLQMFFANNHDQEFDPPKVYPPVPAEKRKPIR
             |  .:|.||||||| ||| || ..  |:: ||.|| :||  :|:|||
DNMT3B  527  CLPQRCHGVLRRRKDWNVRLQAFFTSDTGLEYEAPKLYPAIPAARRRPIR

DNMT3A  636  VLSLFDGIATGLLVLKDLGIQVDRYIASEVCEDSITVGMVRHQGKIMYVG
             ||||||||||| ||||:|||.| :|:||||||:|| || |:|:| | ||
DNMT3B  577  VLSLFDGIATGYLVLKELGIKVGKYVASEVCEESIAVGTVKHEGNIKYVN

DNMT3A  686  DVRSVTQKHIQEWGPFDLVIGGSPCNDLSIVNPARKGLYEGTGRLFFEFY
             |||.:|.|.|:||||||||||||||||| |||||||||||||||||||||
DNMT3B  627  DVRNITKKNIEEWGPFDLVIGGSPCNDLSNVNPARKGLYEGTGRLFFEFY

DNMT3A  736  RLLHDARPKEGDDRPFFWLFENVVAMGVSDKRDISRFLESNPVMIDAKEV
             ||. .|||||||||||||:|||||| | |||||||||| |||||||| .|
DNMT3B  677  HLLNYSRPKEGDDRPFFWMFENVVAMKVGDKRDISRFLECNPVMIDAIKV

DNMT3A  786  SAAHRARYFWGNLPGMNRPLASTVNDKLELQECLEHGRIAKFSKVRTITT
             |||||||||||||||||||.  .. ||||||||:|||: ||||  ||.||||
DNMT3B  727  SAAHRARYFWGNLPGMNRPVIASKNDKLELQDCLEYNRIAKLKKVQTITT

DNMT3A  836  RSNSIKQGKDQHFPVFMNEKEDILWCTEMERVFGFPVHYTDVSNMSRLAR
             :||||||||.| ||| || |||:|||||:||:||||||||||||| | ||
DNMT3B  777  KSNSIKQGKNQLFPVVMNGKEDVLWCTELERIFGFPVHYTDVSNMGRGAR

DNMT3A  886  QRLLGRSWSVPVIRHLFAPLKEYFACV*
             |:|||||||||||||||||||:|||||
DNMT3B  827  QKLLGRSWSVPVIRHLFAPLKDYFACE*
```

FIG.3B-2

```
Exon1  (>=90bp) CGGCAGgtgagcgcccccgggg.intron(17618bp).tggcttctcccacagGAAAGC
Exon2  ( 148bp) TCAGAGgtgctgggcagtgg.intron(   887bp).CTGTTTCCTCTACAGGCCGAA
Exon3  (  62bp) ACACAGgtatggtctctgctc.intron(  3343bp).tgtttccttataaagGACTTG
Exon4  ( 102bp) CCAGCTgtaagtagccacacc.intron(  1642bp).ctctcttgcttctagGTCCGA
Exon5  ( 125bp) ACCAGGgttgttccccagatg.intron(   602bp).tccttctgtcctcacagTCCCTG
Exon6  ( 222bp) TATCAGtatgccgagaggg.intron(  1403bp).tgggttttcttccagGATGGG
Exon7  ( 159bp) TCCGAGgtgagtccggggaag.intron(  2588bp).gtcttttctcttttagGTCTCT
Exon8  ( 108bp) CTGGAGgtaacatgggatgag.intron(   917bp).actctgcctttgcagAAAGCT
Exon9  ( 145bp) AACCAGgtgggaatgagtccc.intron(   765bp).ttttccctcaaaagTGGTTA
Exon10 (  60bp) AATACGgtatttccttcctgt.intron(  1813bp).aattaccttcacagAGAACA
Exon11 ( 126bp) GCCGAGgtgattgttgggtac.intron(   115bp).tctttttctcaatagAACAAA
Exon12 (  45bp) TGGAAGgtaacgttcctctccc.intron(  1095bp).ctgttttcttacagATGGCT
Exon13 (  80bp) TGCCCGgtgagcactgggccc.intron(   417bp).ctctctgctgccagGATCGC
Exon14 ( 113bp) CTGCCGgtgagcactgggctc.intron(  1160bp).tgccactgggtccagGTGTTT
Exon15 ( 184bp) GAATACgtaagccacaggctc.intron(   600bp).ttccttacctgcagGAAGCC
Exon16 (  85bp) CGACAGgtgagttcggggaac.intron(   824bp).ctctgcccccacagGCTACC
Exon17 ( 146bp) AAAAATgtgagggcatcttctc.intron(   536bp).gtctctctctttcagATTGAA
Exon18 (  91bp) TGTATGgtgagcagtcctctc.intron(   352bp).cttctgacacagAGGGTA
Exon19 ( 149bp) CTGGAGgtgagggaatctggg.intron(   958bp).tcttctcccacagTGTAAT
Exon20 (  86bp) GAACAGgtaacaaagggctct.intron(  2867bp).tttggctgttcccagGCCCGT
Exon21 (  70bp) GCCAAGgtaaagaaagtacag.intron(   801bp).cattttgttctccagTTAAAG
Exon22 ( 119bp) CGAAAGgtgagcaaggctgca.intron(  1434bp).ctccggtaccccagGATCTT
Exon23 (1585bp)
```

FIG.4D

|  | I | IV | VI |
|---|---|---|---|
| DNMT1 | DVFSGCGGLSEGFHQAG | DVEMLCGGPPCQGFSGMNR | YRPRFFLLENVRNFVSFKR |
| Dnmt1 | DVFSGCGGLSEGFHQAG | DVEMLCGGPPCQGFSGMNR | YRPRFFLLENVRNFVSYRR |
| MET1(Ath) | DIFAGCGGLSHGLKKAG | QVDFINGGPPCQGFSGMNR | FRPRYFLLENVRTFVSFNK |
| Masc1 | DTFCGKGGGVSLGARQAG | HVDILHLSPPCQTFSRAHT | VRPRLFTVEETDGIMDRQS |
| Masc2 | DIFAGCGGLTLGLDLSG | EVDFIYCGPPCQGFSGVNR | YKPRFVLLENVKGLITTKL |
| Dnmt2 | ELYSGIGGMHHALRESH | SFNMILMSPPCQPFTRIGL | KLPKYILLENVKGFEVSST |
| M.Spr | SLFSGIGAFEAALRNIG | EFDLLVGGSPCQSFSVAGH | KQPKFFVFENVKGLINHDK |
| DNMT3A | SLFDGIATGLLVLKDLG | PFDLVIGGSPCNDLSIVNP | DRPFFWLFENVAMGVSDK |
| Dnmt3a | SLFDGIATGYLVLKELG | PFDLVIGGSPCNDLSIVNP | DRPFFWLFENVAMGVSDK |
| DNMT3B | SLFDGIATGYLVLKELG | PFDLVIGGSPCNDLSNVNP | DRPFFWMFENVAMKVGDK |
| Dnmt3b | SLFDGIATGYLVLKELG | PFDLVIGGSPCNDLSNVNP | NRPFFWMFENVAMKVNDK |
| Zmt3 | SLFDGIATGYLVLRDLG | PFDLLIGGSPCNDLSIVNP | PQPFFWLFENVTFMQTHVK |
| consensus | --F-G--G------- | -GG--PC--------N-- | --P-F----EN- |

|  | IX | X |
|---|---|---|
| DNMT1 | RVVSVRECARSQGFP | LFGNILDKHRQVGNAVPPPLAKAIG |
| Dnmt1 | RVVSVRECARSQGFP | FFGNILDRHRQVGNAVPPPLAKAIG |
| MET1(Ath) | RILTVRECARSQGFP | FAGNINHKHRQIGNAVPPPLAFALG |
| Masc1 | RKFTVRELACIQGFP | FVGTLTDKRRIIGNAVPPPLSAAIM |
| Masc2 | RVYTVRELARAQGFP | GLGGVKKWHRNIGNAVPVPLGEQIG |
| Dnmt2 | RYFTPKEIANLQGFP | EKTTVKQRYRLLGNSLNVHVVAKLL |
| M.Spr | RRLTPLECFRLQAFD | AGISNSQLYKQTGNSITVTVLESIF |
| DNMT3A | DILWCTEMERVFGFP | SNMSRLARQRLLGRSWSVPVIRHLF |
| Dnmt3a | DILWCTEMERVFGFP | SNMSRLARQRLLGRSWSVPVIRHLF |
| DNMT3B | DVLWCTELERIFGFP | SNMGRGARQKLLGRSWSVPVIRHLF |
| Dnmt3b | DVLWCTELERIFGFP | SNMGRGARQKLLGRSWSVPVIRHLF |
| Zmt3 | DHIWITELEKIFGFP | KSMGRPORQRVLGKSWSVPVIRHLL |
| consensus | ---------E---R---GFP | ---------R--G----------P-------- |

FIG. 5A

```
DNMT3A      EDICISCG......SLNVTLEHPLFVGGMCQNCKNCFLECAYQYDDDGYQSYCT
Dnmt3a      EDICISCG......SLNVTLEHPLFVGGMCQNCKNCFLECAYQYDDDGYQSYCT
DNMT3B      EDGCLSCG......RKNPVSFHPLFEGGLCQTCRDRFLELFYMYDDDGYQSYCT
Dnmt3b      EDRCLSCG......KKNPVSFHPLFEGGLCQSCRDRFLELFYMYDEDGYQSYCT
Zmt3        EDFCLSCG......SMSVDIIHPLFEGKLCTNCKFNFTETLYRYDEDGYQSYCT
ATRX_Human  IVSCTACGQQVNHFQKDSIYRHPSLQVLICKNCFKYYMSDDISRDSDGMDEQCR
ATRX_Mouse  IVSCTACGQQVNHFQKDSIYRHPSLQVLICKNCFKYYMSDDISRDSDGMDEQCR
Consensus                                  C    C            C DNMT3A      ICCGGREVLMCGNNNCCRCFCVECVDLLVGPGAAQAAIKE.DPWNCYMCGHKGT
Dnmt3a      ICCGGREVLMCGNNNCCRCFCVECVDLLVGPGAAQAAIKE.DPWNCYMCGHKGT
DNMT3B      VCCEGRELLLCSNTSCCRCFCVECLEVLVGTGTAAEAKLQ.EPWSCYMCLPQRC
Dnmt3b      VCCEGRELLLCSNTSCCRCFCVECLEVLVGAGTAEDAKLQ.EPWSCYMCLPQRC
Zmt3        VCCSGMEVILCAHDSCCRSFCVDCLDILVCQGTFDRLKNV.DPWTCYLCAPETS
ATRX_Human  WCAEGGNLICC..DFCHNAFCKKCILRNLGRKELSTIMDENNQWYCYICHPEPL
ATRX_Mouse  WCAEGGNLICC..DFCHNAFCKKCILRNLGRKELSTIMDENNQWYCYICHPEPL
Consensus    C              C   C                           C
```

FIG. 5B

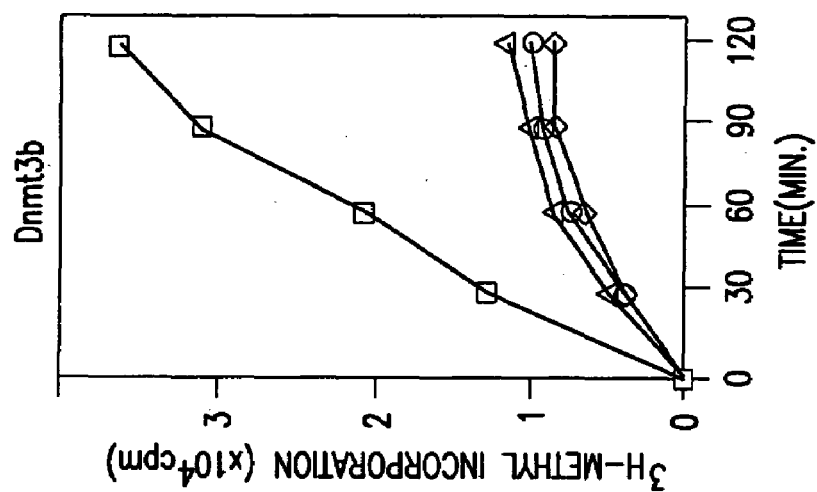
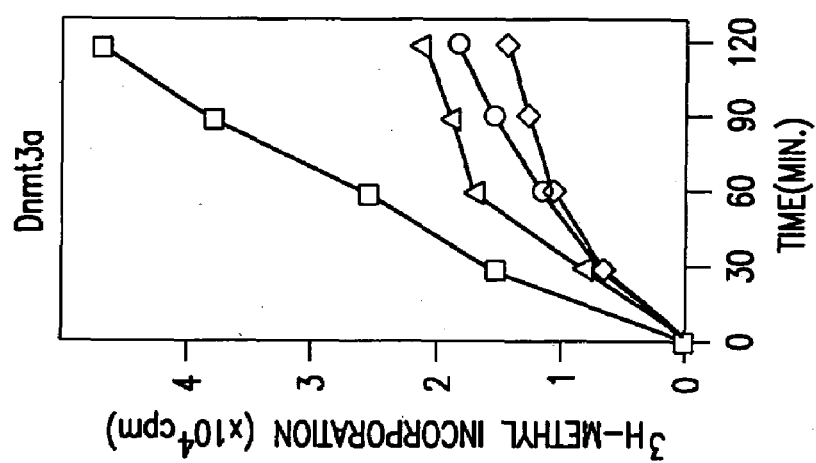
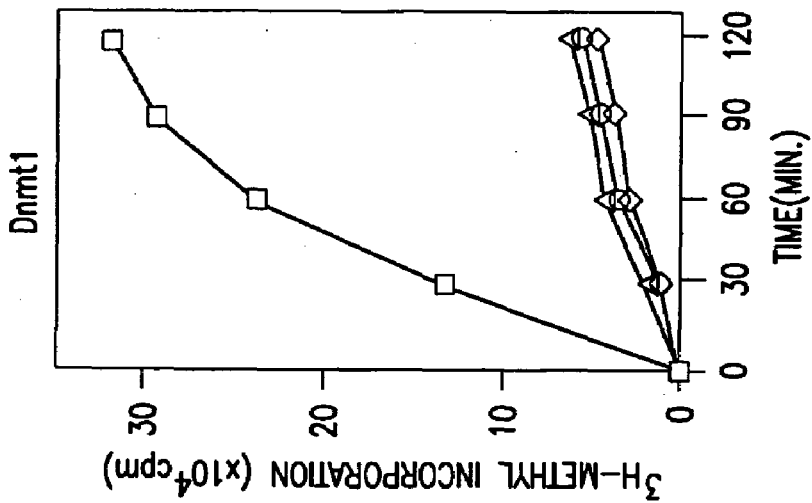
FIG. 7A
FIG. 7B
FIG. 7C

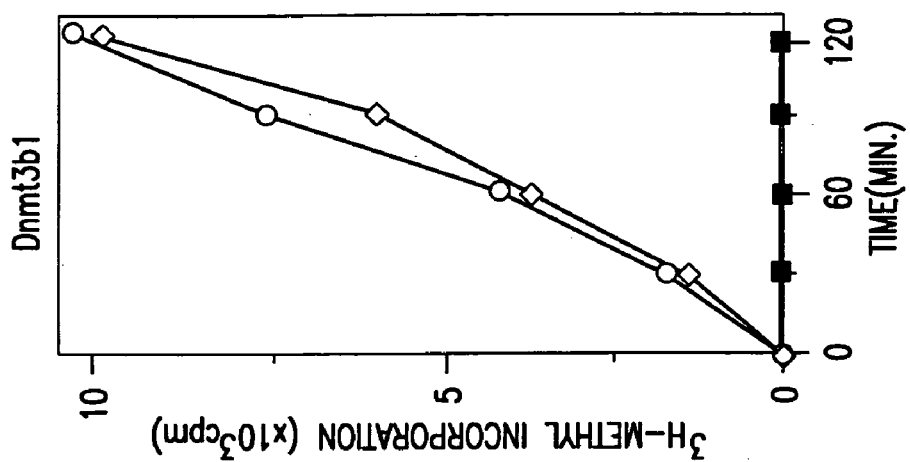
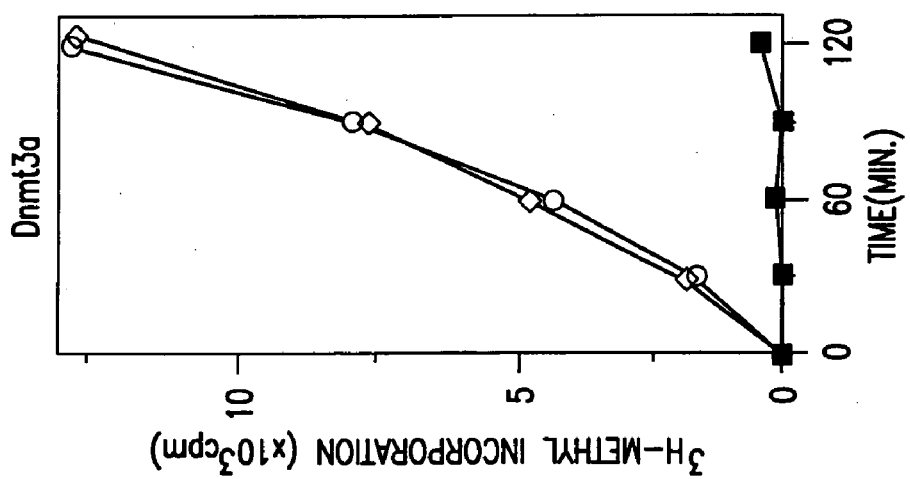
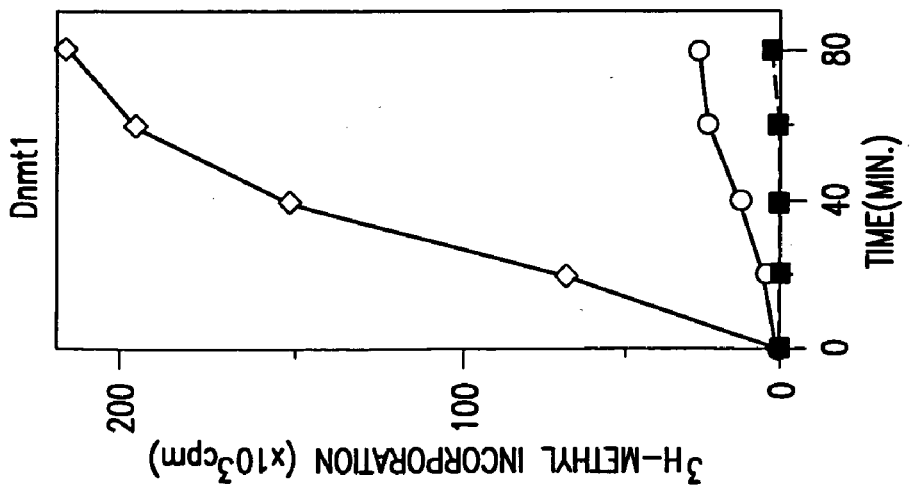
FIG. 8A
FIG. 8B
FIG. 8C

DE NOVO DNA CYTOSINE METHYLTRANSFERASE GENES, POLYPEPTIDES AND USES THEREOF

BACKGROUND OF THE INVENTION

1. Field of the Invention

The present invention relates generally to the fields of molecular biology, developmental biology, cancer biology and medical therapeutics. Specifically, the present invention relates to novel DNA cytosine methyltransferases. More specifically, isolated nucleic acid molecules are provided encoding mouse Dnmt3a and Dnmt3b and human DNMT3A and DNMT3B de novo DNA cytosine methyltransferase genes. Dnmt3a and Dnmt3b mouse and DNMT3A and DNMT3B human polypeptides are also provided, as are vectors, host cells and recombinant methods for producing the same. The invention further relates to an in vitro method for cytosine C5 methylation. Also provided is a diagnostic method for neoplastic disorders, and methods of gene therapy using the polynucleotides of the invention.

2. Related Art

Methylation at the C-5 position of cytosine predominantly in CpG dinucleotides is the major form of DNA modification in vertebrate and invertebrate animals, plants, and fungi. Two distinctive enzymatic activities have been shown to be present in these organisms. The de novo DNA cytosine methyltransferase, whose expression is tightly regulated in development, methylates unmodified CpG sites to establish tissue or gene-specific methylation patterns. The maintenance methyltransferase transfers a methyl group to cytosine in hemi-methylated CpG sites in replicated DNA, thus functioning, to maintain clonal inheritance of the existing methylation patterns.

De novo methylation of genomic DNA is a developmentally regulated process (Jähaner, D. and Jaenish, R., "DNA Methylation in Early Mammalian Development," In *DNA Methylation: Biochemistry and Biological Significance*, Razin, A. et al., eds., Springer-Verlag (1984) pp. 189-219 and Razin, A., and Cedar, H., "DNA Methylation and Embryogenesis," in *DNA Methylation: Molecular Biology and Biological Significance*, Jost., J. P. et al., eds., Birkhäuser Verlag, Basel, Switzerland (1993) pp. 343-357). It plays a pivotal role in the establishment of parental-specific methylation patterns of imprinted genes (Chaillet. J. R. et al., *Cell* 66:77-83 (1991); Stöger, R. et al, *Cell* 73:61-71 (1993); Brandeis, M. et al. *EMBO J.* 12:3669-3677 (1993); Tremblay, K. D. et al., *Nature Genet.* 9:407-413 (1995); and Tucker, K. L. et al., *Genes Dev.* 10:1008-1020 (1996)), and in the regulation of X chromosome inactivation in mammals (Brockdoff, N. "Convergent Themes in X Chromosome Inactivation and Autosomal Imprinting," in *Genomic Imprinting: Frontiers in Molecular Biology*, Reik, W. and Sorani, A. eds., IRL Press Oxford (1997) pp. 191-210; Ariel, M. et al., *Nature Genet.* 9:312-315 (1995); and Zucotti, M. and Monk, M. *Nature Genet.* 9:316-320 (1995)).

Thus, C5 methylation is a tightly regulated biological process important in the control of gene regulation. Additionally, aberrant de novo methylation can lead to undesirable consequences. For example, de novo methylation of growth regulatory genes in somatic tissues is associated with tumorigenesis in humans (Laird, P. W. and Jaenish, R. *Ann. Rev. Genet.* 30:441-464 (1996); Baylin, S. B. et al., *Adv. Cancer. Res.* 72:141-196 (1998); and Jones, P. A. and Gonzalgo, M. L. *Proc. Natl. Acad. Sci. USA* 94:2103-2105 (1997)).

The gene encoding the major maintenance methyltransferase, Dnmt1, was first cloned in mice (Bestor. T. H. et al., *J. Mol. Biol.* 203:971-983 (1988), and the homologous genes were subsequently cloned from a number of organisms, including *Arabidoposis*, sea urchin, chick, and human. Dnmt1 is expressed ubiquitously in human and mouse tissues. Targeted disruption of Dnmt1 results in a genome-wide loss of cytosine methylation and embryonic lethality (Li et al., 1992). Interestingly, Dnmt1 is dispensable for the survival and growth of the embryonic stem cells, but appears to be required for the proliferation of differentiated somatic cells (Lei et al., 1996). Although it has been shown that the enzyme encoded by Dnmt1 can methylate DNA de novo in vitro (Bestor, 1992), there is no evidence that Dnmt1 is directly involved in de novo methylation in normal development. Dnmt1 appears to function primarily as a maintenance methyltransferase because of its strong preference for hemi-methylated DNA and direct association with newly replicated DNA (Leonhardt, H. et al., *Cell* 71:865-873 (1992)). Additionally, ES cells homozygous for a null mutation of Dnmt1 can methylate newly integrated retroviral DNA, suggesting that Dnmt1 is not required for de novo methylation and an independently encoded de novo DNA cytosine methyltransferase is present in mammalian cells (Lei et al., 1996).

Various methods of disrupting Dnmt1 protein activity are known to those skilled in the art. For example, see PCT Publication No. WO92/06985, wherein mechanism based inhibitors are discussed. Applications involving antisense technology are also known; U.S. Pat. No. 5,578,716 discloses the use of antisense oligonucleotides to inhibit Dnmt1 activity, and Szyf et al., *J. Biol. Chem.* 267: 12831-12836, 1992, demonstrates that myogenic differentiation can be affected through the antisense inhibition of Dnmt1 protein activity.

Thus, while there is a significant amount of knowledge in the art regarding the maintenance C5 methyltransferase (Dnmt1), there is no information regarding nucleic acid or protein structure and expression or enzymatic properties of the de novo C5 methyltransferase in mammals.

SUMMARY OF THE INVENTION

A first aspect of the invention provides novel de novo DNA cytosine methyltransferase nucleic acids and polypeptides that are not available in the art. A second aspect of the invention relates to de novo DNA cytosine methyltransferase recombinant materials and methods for their production. A third aspect of the invention relates to the production of recombinant de novo DNA cytosine methyltransferase polypeptides. A fourth aspect of the invention relates to methods for using such de novo DNA cytosine methyltransferase polypeptides and polynucleotides. Such uses include the treatment of neoplastic disorders, among others. Yet another aspect of the invention relates to diagnostic assays for the detection of diseases associated with inappropriate de novo DNA cytosine methyltransferase activity or levels and mutations in de novo DNA cytosine methyltransferases that might lead to neoplastic disorders.

BRIEF DESCRIPTION OF THE FIGURES

FIGS. 1A-1 through 1A-4 show the nucleotide sequence of the mouse Dnmt3a gene. FIGS. 1B-1 through 1B-4 show the nucleotide sequence of the mouse Dnmt3b gene. FIGS. 1C-1 through 1C-4 show the nucleotide sequence of the human DNMT3A gene. FIGS. 1D-1 through 1D-4 show the nucleotide sequence of the human DNMT3B gene.

FIG. 2A-2D shows the deduced amino acid sequence of mouse Dnmt3a and Dnmt3b and human DNMT3A and DNMT3B genes, respectively. Sequences are presented in single letter amino acid code.

FIGS. 3A-1 and 3A-2 show a comparison of mouse Dnmt3a and Dnmt3b amino acid sequences, and FIGS. 3B-1 and 3B-2 present a comparison of the protein sequences of human DNMT3A and DNMT3B1.

FIGS. 4C and 4D present a schematic of the human DNMT3B gene organization and exon/intron junction sequences.

FIG. 5A presents a comparison of highly conserved protein structural motifs for eukaryotic and prokaryotic C5 methyltransferase. FIG. 5B presents a sequence alignment of the C-rich domain of vertebrate DNMT3 proteins and the X-lined ATRX gene.

FIG. 7A-7D demonstrates in vitro methyltransferase activities of mouse Dnmt3a and Dnmt3b proteins.

FIGS. 8A-E demonstrate in vitro analysis of de novo and maintenance activities of Dnmt3a, Dnmt3b1 and Dnmt3b2 proteins.

DETAILED DESCRIPTION OF THE PREFERRED EMBODIMENTS

Definitions

Figure 4A:
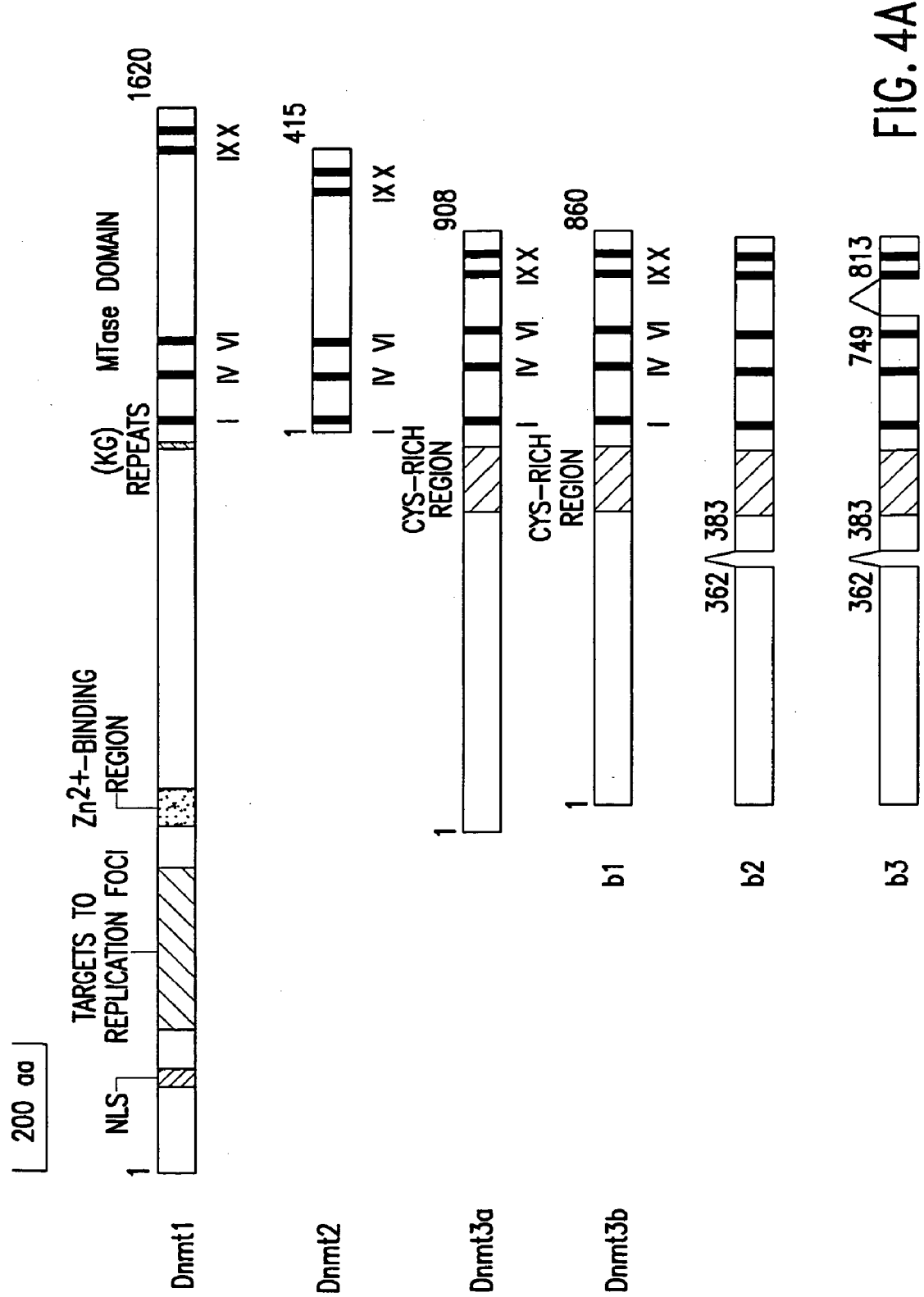
FIG. 4A presents a schematic comparison of mouse Dnmt1, Dnmt2, Dnmt3a and Dnmt3b protein structures.

In the description that follows, a number of terms used in recombinant DNA technology are utilized extensively. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Recombinant Host: According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are eukaryotic cells transformed with the DNA construct of the invention. More specifically, mammalian cells are preferred.

Recombinant vector: Any cloning vector or expression vector which contains the desired cloned gene(s).

Host Animal: Transgenic animals, all of whose germ and somatic cells contain the DNA construct of the invention. Such transgenic animals are in general vertebrates. Preferred Host Animals are mammals such as non-human primates, mice, sheep, pigs, cattle, goats, guinea pigs, rodents, e.g. rats, and the like. The term Host Animal also includes animals in all stages of development, including embryonic and fetal stages.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. According to the invention, preferred promoters are heterologous to the de novo DNA cytosine methyltransferase genes, that is, the promoters do not drive expression of the gene in a mouse or human. Such promoters include the CMV promoter (InVitrogen, San Diego, Calif.), the SV40, MMTV, and hMTIIa promoters (U.S. Pat. No. 5,457,034), the HSV-1 4/5 promoter (U.S. Pat. No. 5,501,979), and the early intermediate HCMV promoter (WO92/17581). In one emdodiment, it is preferred that the promoter is tissue-specific, that is, it is induced selectively in a specific tissue. Also, tissue-specific enhancer elements may be employed. Additionally, such promoters may include tissue and cell-specific promoters of an organism.

Gene: A DNA sequence that contains information needed for expressing a polypeptide or protein.

Structural gene: A DNA sequence that is transcribed into messenger RNA (mRNA) that is then translated into a sequence of amino acids characteristic of a specific polypeptide.

Complementary DNA (cDNA): A "complementary DNA," or "cDNA" gene includes recombinant genes synthesized by reverse transcription of mRNA and from which intervening sequences (introns) have been removed.

Expression: Expression is the process by which a polypeptide is produced from a structural gene. The process involves transcription of the gene into mRNA and the translation of such mRNA into polypeptide(s).

Homologous/Nonhomologous: Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci.* 80:726-730 (1983)). Two nucleic acid molecules are considered to be "nonhomologous" if their nucleotide sequences share a similarity of less than 40%.

Polynucleotide: This term generally refers to any polyribonucleotide or polydeoxyribonucleotide, which may be unmodified RNA or DNA or modified RNA or DNA. "Polynucleotides" include, without limitation single- and double-stranded DNA. DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

Polypeptide: This term refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties,* 2nd Ed., T. E. Creighton, W. H. Freeman and Company, New York. 1993 and Wold, F., Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors". *Methods in Enzymol.* 182:626-646 (1990) and Rattan et al. "Protein Synthesis: Posttranslational Modifications and Aging", *Ann NY cad Sci* 663:48-62 (1992).

Variant: The term used herein is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

Identity: This term refers to a measure of the identity of nucleotide sequences or amino acid sequences. In general, the sequences are aligned so that the highest order match is obtained. "Identity" per se has an art-recognized meaning and can be calculated using published techniques. (See, e.g.: *Computational Molecular Biology*, Lesk, A. M. ed., Oxford University Press, New York, 1988; *Biocomputing, Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCS program package (Devereux, J. et al., *Nucleic Acids Research* 12(1):387(1984)), BLASTP, BLASTN, FASTA (Atschul, S. F. et al., *J. Mol. Biol.* 215:403 (1990)).

Therefore, as used herein, the term "identity" represents a comparison between a test and reference polynucleotide. More specifically, reference polynucleotides are identified in this invention as SEQ ID Nos: 1, 2, 3 and 4, and a test polynucleotide is defined as any polynucleotide that is 90% or more identical to a reference polynucleotide. As used herein, the term "90% or more" refers to percent identities from 90 to 99.99 relative to the reference polynucleotide. Identity at a level of 90% or more is indicative of the fact that, assuming for exemplification purposes a test and reference polynucleotide length of 100 nucleotides, that no more than 10% (i.e., 10 out of 100) nucleotides in the test polynucleotide differ from that of the reference polynucleotide. Such differences may be represented as point mutations randomly distributed over the entire length of the sequence or they may be clustered in one or more locations of varying length up to the maximum allowable 10 nucleotide difference. Differences are defined as nucleotide substitutions, deletions or additions of sequence. These differences may be located at any position in the sequence, including but not limited to the 5' end, 3' end, coding and non coding sequences.

Fragment: A "fragment" of a molecule such as de novo DNA cytosine methyltransferases is meant to refer to any polypeptide subset of that molecule.

Functional Derivative: The term "functional derivatives" is intended to include the "variants," "analogues," or "chemical derivatives" of the molecule. A "variant" of a molecule such as de novo DNA cytosine methyltransferases is meant to refer to a naturally occurring molecule substantially similar to either the entire molecule, or a fragment thereof. An "analogue" of a molecule such as de novo DNA cytosine methyltransferases is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Protein Activity or Biological Activity of the Protein: These expressions refer to the metabolic or physiologic function of de novo DNA cytosine methyltransferase protein including similar activities or improved activities or these activities with decreased undesirable side-effects. Also included are antigenic and immunogenic activities of said de novo DNA cytosine methyltransferase protein. Among the physiological or metabolic activities of said protein is the transfer of a methyl group to the cytosine C5 position of duplex DNA. Such DNA may completely lack any methylation of may be hemimethylated. As demonstrated in Example 8, de novo DNA cytosine methyltransferases methylate C5 in cytosine moieties in nonmethylated DNA.

De novo DNA Cytosine Methyltransferases Polynucleotides: This term refers to a polynucleotide containing a nucleotide sequence which encodes a de novo DNA cytosine methyltransferase polypeptide or fragment thereof or that encodes a de novo DNA cytosine methyltransferase polypeptide or fragment wherein said nucleotide sequence has at least 90% identity to a nucleotide sequence encoding the polypeptide of SEQ ID Nos: 5, 6, 7 or 8, or a corresponding fragment thereof, or which has sufficient identity to a nucleotide sequence contained in SEQ ID NO:1, 2, 3 or 4.

De novo DNA Cytosine Methyltransferases Polypeptides: This term refers to polypeptides with amino acid sequences sufficiently similar to the de novo DNA cytosine methyltransferase protein sequence in SEQ ID NO:5, 6, 7 or 8 and that at least one biological activity of the protein is exhibited.

Antibodies: As used herein includes polyclonal and monoclonal antibodies, chimeric, single chain, and humanized antibodies, as well as Fab fragments, including the products of an Fab or other immunoglobulin expression library.

Substantially pure: As used herein means that the desired purified protein is essentially free from contaminating cellular components, said components being associated with the desired protein in nature, as evidenced by a single band following polyacrylamide-sodium dodecyl sulfate gel electrophoresis. Contaminating cellular components may include, but are not limited to, proteinaceous, carbohydrate, or lipid impurities.

The term "substantially pure" is further meant to describe a molecule which is homogeneous by one or more purity or homogeneity characteristics used by those of skill in the art. For example, a substantially pure de novo DNA cytosine methyltransferases will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds. In addition, the term is not meant to exclude de novo DNA cytosine methyltransferase fusion proteins isolated from a recombinant host.

Isolated: A term meaning altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of a de novo DNA cytosine methyltransferase polypeptide can be substantially purified by the one-step method described in Smith and Johnson, *Gene* 67.31-40 (1988).

Neoplastic disorder: This term refers to a disease state which is related to the hyperproliferation of cells. Neoplastic disorders include, but are not limited to, carcinomas, sarcomas and leukemias.

Gene Therapy: A means of therapy directed to altering the normal pattern of gene expression of an organism. Generally, a recombinant polynucleotide is introduced into cells or tissues of the organism to effect a change in gene expression.

Antisense RNA gene/Antisense RNA. In eukaryotes, mRNA is transcribed by RNA polymerase II. However, it is also known that one may construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA."

Antisense RNAs are not normally translatable due to the presence of translation stop codons in the antisense RNA sequence.

Antisense oligonucleotide: A DNA or RNA molecule or a derivative of a DNA or RNA molecule containing a nucleotide sequence which is complementary to that of a specific mRNA. An antisense oligonucleotide binds to the complementary sequence in a specific mRNA and inhibits translation of the mRNA. There are many known derivatives of such DNA and RNA molecules. See, for example, U.S. Pat. Nos. 5,602,240, 5,596,091, 5,506,212, 5,521,302, 5,541,307, 5,510,476, 5,514,787, 5,543,507, 5,512,438, 5,510,239, 5,514,577, 5,519,134, 5,554,746, 5,276,019, 5,286,717, 5,264,423, as well as WO96/35706, WO96/32474, WO96/29337 (thiono triester modified antisense oligodeoxynucleotide phosphorothioates), WO94/17093 (oligonucleotide alkylphosphonates and alkylphosphothioates), WO94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al., *Biotech.* 6:958-976 (1988); Uhlmann et al., *Chem. Rev.* 90:542-585 (1990)), WO94/02499 (oligonucleotide alkylphosphonothioates and arylphosphonothioates), and WO92/20697 (3'-end capped oligonucleotides). Particular de novo DNA cytosine methyltransferase antisense oligonucleotides of the present invention include derivatives such as S-oligonucleotides (phosphorothioate derivatives or S-oligos, see, Jack Cohen, *Oligodeoxynucleotides, Antisense Inhibitors of Gene Expression*, CRC Press (1989)). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1, 1-dioxide which is a sulfur transfer reagent. See Iyer et al., *J. Org. Chem.* 55:4693-4698 (1990); and Iyer et al., *J. Am. Chem. Soc.* 112:1253-1254 (1990).

Antisense Therapy: A method of treatment wherein antisense oligonucleotides are administered to a patient in order to inhibit the expression of the corresponding protein.

I. Deposited Material

The invention relates to polynucleotides encoding and polypeptides of novel de novo DNA cytosine methyltransferase proteins. The invention relates especially to de novo DNA cytosine methyltransferase mouse Dnmt3a and Dnmt3b cDNAs and the human DNMT3A and DNMT3B cDNAs set out in SEQ ID NOs: 1, 2, 3 and 4, respectively. The invention also relates to mouse Dnmt3a and Dnmt3b nd human DNMT3A and DNMTB e novo DNA cytosine methyltransferase polypeptides set out in SEQ ID NOs:5, 6, 7, and 8, respectively. The invention further relates to the de novo DNA cytosine methyltransferase nucleotide sequences of the mouse Dnmt3a cDNA (plasmid pMT3a) and Dnmt3b cDNA (plasmid pMT3b) and the human DNMTα cDNA (plasmid pMT3A) in ATCC Deposit Nos. 209933, 209934, and 98809, respectively, and the amino acid sequences encoded therein.

The nucleotide sequence of the human DNMT3B cDNA identified in SEQ ID NO:4 is available in a clone (ATCC Deposit No. 326637) independently deposited by the I.M.A.G.E. Consortium. The invention relates to the de novo DNA cytosine methyltransferase polypeptide encoded therein.

Clones containing mouse Dnmt3a and Dnmt3b cDNAs were deposited with the American Type Culture Collection (ATCC), Manassas, Va. 20110-2209, USA, on Jun. 16, 1998, and assigned ATCC Deposit Nos. 209933 and 209934, respectively. The human DNMT3A cDNA was deposited with the ATCC on Jul. 10, 1998, and assigned ATCC Deposit No. 98809.

While the ATCC deposits are believed to contain the de novo DNA cytosine methyltransferase cDNA sequences shown in SEQ ID NOs:1, 2, 3, and 4, the nucleotide sequences of the polynucleotide contained in the deposited material, as well as the amino acid sequence of the polypeptide encoded thereby, are controlling in the event of any conflict with any description of sequences herein.

The deposits for mouse Dnmt3a and Dnmt3b cDNAs and the human DNMT3A cDNA were made under the terms of the Budapest Treaty on the international recognition of the deposit of micro-organisms for purposes of patent procedure. The deposits are provided merely as a convenience for those of skill in the art and are not an admission that a deposit is required for enablement, such as that required under 35 U.S.C. § 112.

II. Polynucleotides of the Invention

Another aspect of the invention relates to isolated polynucleotides, and polynucleotides closely related thereto, which encode the de novo DNA cytosine methyltransferase polypeptides. As shown by the results presented in FIG. 5, sequencing of the cDNAs contained in the deposited clones encoding mouse and human de novo DNA cytosine methyltransferases confirms that the de novo DNA cytosine methyltransferase proteins of the invention are structurally related to other proteins of the DNA methyltransferase family.

The polynucleotides of the present invention encoding de novo DNA cytosine methyltransferase proteins may be obtained using standard cloning and screening procedures as described in Example 1. Polynucleotides of the invention can also be obtained from natural sources such as genomic DNA libraries or can be synthesized using well known and commercially available techniques.

Among particularly preferred embodiments of the invention are polynucleotides encoding de novo DNA cytosine methyltransferase polypeptides having the amino acid sequence set out in SEQ ID NO:5, SEQ ID NO:6, SEQ ID NO:7, or SEQ ID NO:8, and variants thereof.

A particular nucleotide sequence encoding a de novo DNA cytosine methyltransferase polypeptide may be identical over its entire length to the coding sequence in SEQ ID NOs:1, 2, or 3. Alternatively, a particular nucleotide sequence encoding a de novo DNA cytosine methyltransferase polypeptide may be an alternate form of SEQ ID NOs:1, 2, 3 and 4 due to degeneracy in the genetic code or variation in codon usage encoding the polypeptides of SEQ ID NOs:5, 6, 7, or 8. Preferably, the polynucleotides of the invention contain a nucleotide sequence that is highly identical, at least 90% identical, with a nucleotide sequence encoding a de novo DNA cytosine methyltransferase polypeptide or at least 90% identical with the encoding nucleotide sequence set forth in SEQ ID NOs:1, 2, or 3. Polynucleotides of the invention may be 90 to 99% identical to the nucleotides sequence set forth in SEQ ID NO:4.

When a polynucleotide of the invention is used for the recombinant production of a de novo DNA cytosine methyltransferase polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* 86:821-824 (1989), or it may be the HA tag, which corresponds to an epitope derived from the influenza hemagglutinin protein (Wilson, I., et al, *Cell* 37:767, 1984). The polynucleotide may also contain non-coding 5' and 3' sequences, such as transcribed, non-translated sequences, splicing and polyadenylation signals, ribosome binding sites and sequences that stabilize mRNA.

Embodiments of the invention include isolated nucleic acid molecules comprising a polynucleotide having a nucleotide sequence at least 90% identical, and more preferably at least 91%, 92%, 93%, 94%, 95%, 96%, 97%, 98% or 99% identical to (a) a nucleotide sequence encoding a de novo DNA cytosine methyltransferase polypeptide having the amino acid sequence in SEQ ID NO:1, SEQ ID NO:2, or SEQ ID NO:3; (b) a nucleotide sequence encoding a de novo DNA cytosine methyltransferase polypeptide having the amino acid sequence encoded by the cDNA clone contained in ATCC Deposit No. 209933, ATCC Deposit No. 209934, or ATCC Deposit No. 98809; or (c) a nucleotide sequence complementary to any of the nucleotide sequences in (a) or (b). Additionally, an isolated nucleic acid of the invention may be a polynucleotide at least 90% but not more than 99% identical to (a) a nucleotide sequence encoding a de novo DNA cytosine methyltransferase polypeptide having the amino acid sequence in SEQ ID NO:4; (b) a nucleotide sequence encoding a de novo DNA cytosine methyltransferase polypeptide having the amino acid sequence encoded by the cDNA clone contained in ATCC Deposit No. 326637; or (c) a nucleotide sequence complementary to any of the nucleotide sequences in (a) or (b).

Conventional means utilizing known computer programs such as the BestFit program (Wisconsin Sequence Analysis Package, Version 10 for Unix, Genetics Computer Group. University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to any one of the nucleotide sequences shown in SEQ ID NO: 1, SEQ ID NO:2, SEQ ID NO:3, or SEQ ID NO:4 or to any one of the nucleotide sequences of the deposited cDNA clones contained in ATCC Deposit No. 209933, ATCC Deposit No. 209934, ATCC Deposit No. 98809, or ATCC Deposit No. 326637.

Further preferred embodiments are polynucleotides encoding de novo DNA cytosine methyltransferases and de novo DNA cytosine methyltransferase variants that have an amino acid sequence of the de novo DNA cytosine methyltransferase protein of SEQ ID NO:5, SEQ ID NO:6, SEQ ID NO:7, or SEQ ID NO:8 in which several, 1, 1-2, 1-3, 1-5 or 5-10 amino acid residues are substituted, deleted or added, in any combination.

Further preferred embodiments of the invention are polynucleotides that are at least 90% identical over their entire length to a polynucleotide encoding a de novo DNA cytosine methyltransferase polypeptide having the amino acid sequence set out in SEQ ID NO:5, SEQ ID NO:6, SEQ ID NO:7, or SEQ ID NO:8, and polynucleotides which are complementary to such polynucleotides. Most highly preferred are polynucleotides that comprise regions that are at least 90% identical over their entire length to a polynucleotide encoding the de novo DNA cytosine methyltransferase polypeptides of the ATCC deposited human DNMT3A cDNA clone and polynucleotides complementary thereto, and 90% to 99% identical over their entire length to a polynucleotide encoding the de novo DNA cytosine methyltransferase polypeptides of the ATCC deposited human DNMT3B cDNA clone and polynucleotides complementary thereto. In this regard, polynucleotides at least 95% identical over their entire length to the same are particularly preferred, and those with at least 97% identity are especially preferred. Furthermore, those with at least 98% identity are highly preferred and with at least 99% identity being the most preferred.

In a more specific embodiment, the nucleic acid molecules of the present invention, e.g. isolated nucleic acids comprising a polynucleotide having a nucleotide sequence encoding a de novo DNA cytosine methyltransferase polypeptide or fragment thereof, are not the sequence of nucleotides, the nucleic acid molecules (e.g., clones), or the nucleic acid inserts identified in one or more of the below cited public EST or STS GenBank Accession Reports.

The following public ESTs were identified that relate to portions of SEQ ID NO:1: AA052791(SEQ ID NO:9); AA111043(SEQ ID NO:10); AA154890(SEQ ID NO:11); AA240794(SEQ ID NO:12); AA756653(SEQ ID NO:13); W58898(SEQ ID NO:14); W59299(SEQ ID NO:15); W91664(SEQ ID NO:16); W91665(SEQ ID NO:17); to portions of SEQ ID NO:2: AA116694 (SEQ ID NO:18); AA119979 (SEQ ID NO:19); AA177277 (SEQ ID NO:20); AA210568 (SEQ ID NO:21); AA399749 (SEQ ID NO:22); AA407106 (SEQ ID NO:23); AA575617 (SEQ ID NO:24); to portions of SEQ ID NO:3: AA004310 (SEQ ID NO:25); AA004399 (SEQ ID NO:26); AA312013 (SEQ ID NO:27); AA355824 (SEQ ID NO:28); AA533619 (SEQ ID NO:29); AA361360 (SEQ ID NO:30); AA364876 (SEQ ID NO:31); AA503090 (SEQ ID NO:32); AA533619 (SEQ ID NO:33); AA706672 (SEQ ID NO:34); AA774277 (SEQ ID NO:35); AA780277 (SEQ ID NO:36); H03349 (SEQ ID NO:37); H04031 (SEQ ID NO:38); H53133 (SEQ ID NO:39); H53239 (SEQ ID NO:40); H64669 (SEQ ID NO:41); N26002 (SEQ ID NO:42); N52936 (SEQ ID NO:43); N88352 (SEQ ID NO:44); N89594 (SEQ ID NO:45); R19795 (SEQ ID NO:46); R47511 (SEQ ID NO:47); T50235 (SEQ ID NO:48); T78023 (SEQ ID NO:49); T78186 (SEQ ID NO:50); W22886 (SEQ ID NO:51); W67657 (SEQ ID NO:52); W68094 (SEQ ID NO:53); W76111 (SEQ ID NO:54); Z38299 (SEQ ID NO:55); Z42012 (SEQ ID NO:56); and that relate to SEQ ID NO:4: AA206103(SEQ ID NO:57); AA206264(SEQ ID NO:58); AA216527(SEQ ID NO:59); AA216697(SEQ ID NO:60); AA305044(SEQ ID NO:61); AA477705(SEQ ID NO:62); AA477706(SEQ ID NO:63); AA565566(SEQ ID NO:64); AA599893(SEQ ID NO:65); AA729418(SEQ ID NO:66); AA887508(SEQ ID NO:67); F09856(SEQ ID NO:68); F12227(SEQ ID NO:69); N39452(SEQ ID NO:70); N48564 (SEQ ID NO:71); T66304(SEQ ID NO:72); and T66356 (SEQ ID NO:73); AA736582(SEQ ID NO:77); AA748883 (SEQ ID NO:78); AA923295(SEQ ID NO:79); AA1000396 (SEQ ID NO:80); A1332472(SEQ ID NO:81); W22473 (SEQ ID NO:82) and the I.M.A.G.E. Consortium clone ID 22089 (ATCC Deposit No. 326637)(SEQ ID NO:76). Additionally, STSs G06200(SEQ ID NO:74) and G15302(SEQ ID NO:75) were identified in a search with SEQ ID NOS.:3 and 4, respectively.

The present invention is further directed to fragments of SEQ ID NO:1, 2 or 3, or to fragments of the cDNA nucleotide sequence found in ATCC Deposit Nos. 209933, 209934, or 98809. A fragment may be defined to be at least about 15 nt, and more preferably at least about 20 nt, still more preferably at least about 30 nt, and even more preferably, at least about 40 nt in length. Such fragments are useful as diagnostic probes and primers as discussed herein. Of course larger DNA fragments are also useful according to the present invention, as are fragments corresponding to most, if not all, of the nucleotide sequence of the cDNA clones contained in the plasmids deposited as ATCC Deposit No. 209933, ATCC Deposit No. 209934 or ATCC Deposit No. 98809; or as shown in SEQ ID NO:1, SEQ ID NO:2, or SEQ ID NO:3. Generally, polynucleotide fragments of the invention may be defined algebraically in the following way: (a) for SEQ ID NO:1, as 15+N, wherein N equals zero or any positive integer up to 4176; (b) for SEQ ID NO:2, as 15+N, wherein N equals zero or any positive integer up to 4180; and (c) for SEQ ID NO:3, as 15+N, wherein N equals zero or any positive integer up to 4401. By a fragment at least 20 nt in length, for example, is intended fragments which include 20 or more contiguous bases from a nucleotide sequence of the ATCC deposited cDNAs or the nucleotide sequence as shown in SEQ ID NO:1, SEQ ID NO:2 or SEQ ID NO:3.

In another embodiment, the invention is directed to fragments of SEQ ID NO:4. Such fragments are defined as comprising the nucleotide sequence encoding the specific amino acid residues integral and immediately adjacent to the site where DNMT3B exons are spliced together. The DNMT3B sequence of SEQ ID NO:4 consists of 23 exon sequences defined accordingly: Exon 1 consists of nucleotides 1-108 of SEQ ID NO:4; Exon 2 consists of nucleotides 109-256 of SEQ ID NO:4; Exon 3 consists of nucleotides 257-318 of SEQ ID NO:4; Exon 4 consists of nucleotides 319-420 of SEQ ID NO:4; Exon 5 consists of nucleotides 421-546 of SEQ ID NO:4; Exon 6 consists of nucleotides 547-768 of SEQ ID NO:4; Exon 7 consists of nucleotides 769-927 of SEQ ID NO:4; Exon 8 consists of nucleotides 928-1035 of SEQ ID NO:4; Exon 9 consists of nucleotides 1036-1180 of SEQ ID NO:4; Exon 10 consists of nucleotides 1181-1240 of SEQ ID NO:4; Exon 11 consists of nucleotides 1241-1366 of SEQ ID NO:4; Exon 12 consists of nucleotides 1367-1411 of SEQ ID NO:4; Exon 13 consists of nucleotide 1412-1491 of SEQ ID NO:4. Exon 14 consists of nucleotides 1492-1604 of SEQ ID NO:4; Exon 15 consists of nucleotides 1605-1788 of SEQ ID NO:4; Exon 16 consists of nucleotides 1789-1873 of SEQ ID NO:4; Exon 17 consists of nucleotides 1874-2019 of SEQ ID NO:4; Exon 18 consists of nucleotides 2020-2110 of SEQ ID NO:4; Exon 19 consists of nucleotides 2111-2259 of SEQ ID NO:4; Exon 20 consists of nucleotides 2260-2345 of SEQ ID NO:4; Exon 21 consists of nucleotides 2346-2415 of SEQ ID NO:4; Exon 22 consists of nucleotides 2416-2534 of SEQ ID NO:4; and Exon 23 consists of nucleotides 2535-4145 of SEQ ID NO:4.

It should be understood by those skilled in the art that with regards to SEQ ID NO:4. Exon 1 and Exon 23 are herein defined for the purposes of the invention. The first nucleotide of Exon 1 may or may not be the transcriptional start site for the DNMT3B genomic locus, and the last nucleotide identified for Exon 23 may or may not reflect the last nucleotide transcribed in vivo.

Thus, by way of example, fragments of SEQ ID NO:4 comprise the following exon-exon junctions of 20 nucleotides in length: the exon1/exon 2 junction of nucleotides 98-118 of SEQ ID NO:4; the exon 2/exon 3 junction of nucleotides 246-266 of SEQ ID NO:4; the exon 3/exon 4 junction of nucleotides 308-328 of SEQ ID NO:4; the exon 4/exon 5 junction of nucleotides 410-430 of SEQ ID NO:4; the exon 5/exon 6 junction of nucleotides 536-556 of SEQ ID NO:4; the exon 6/exon 7 junction of nucleotides 758-778 of SEQ ID NO:4; the exon 7/exon 8 junction of nucleotides 917-937 of SEQ ID NO:4; the exon 8/exon 9 junction of nucleotides 1025-1045 of SEQ ID NO:4; the exon 9/exon 10 junction of nucleotides 1170-1190 of SEQ ID NO:4; the exon 10/exon 11 junction of nucleotides 1230-1250 of SEQ ID NO:4; the exon 11/exon 12 junction of nucleotides 1356-1376 of SEQ ID NO:4; the exon 12/exon 13 junction of nucleotides 1401-1421 of SEQ ID NO:4; the exon 13/exon 14 junction of nucleotides 1481-1501 of SEQ ID NO:4; the exon 14/exon 15 junction of nucleotides 1594-1614 of SEQ ID NO:4; the exon 15/exon 16 junction of nucleotides 1778-1798 of SEQ ID NO:4; the exon 16/exon 17 junction of nucleotides 1863-1883 of SEQ ID NO:4; the exon 17/exon 18 junction of nucleotides 2009-2029 of SEQ ID NO:4; the exon 18/exon 19 junction of nucleotides 2100-2120 of SEQ ID NO:4; the exon 19/exon 20 junction of nucleotides 2249-2269 of SEQ ID NO:4; the exon 20/exon 21 junction of nucleotides 2335-2355 of SEQ ID NO:4; the exon 21/exon 22 junction of nucleotides 2405-2425 of SEQ ID NO:4; and the exon 22/exon 23 junction of nucleotides 2524-2544 of SEQ ID NO:4.

As will be clear to those skilled in the art, other exon-exon junction fragments of SEQ ID NO:4 are possible which comprise 30, 40, 50, 60, 70, 80, 90, 100, 200, 300, 400, 500, etc., nucleotides of SEQ ID NO:4. For the purposes of constructing such fragments, the following exon-exon/junctions are identified: the exon1/exon 2 junction of nucleotides 108 and 109 of SEQ ID NO:4; the exon 2/exon 3 junction of nucleotides 256 and 257 of SEQ ID NO:4; the exon 3/exon 4 junction of nucleotides 318 and 319 of SEQ ID NO:4; the exon 4/exon 5 junction of nucleotides 420 and 421 of SEQ ID NO:4; the exon 5/exon 6 junction of nucleotides 546 and 547 of SEQ ID NO:4; the exon 6/exon 7 junction of nucleotides 768 and 769 of SEQ ID NO:4; the exon 7/exon 8 junction of nucleotides 927 and 928 of SEQ ID NO:4; the exon 8/exon 9 junction of nucleotides 1035 and 1036 of SEQ ID NO:4; the exon 9/exon 10 junction of nucleotides 1180 and 1181 of SEQ ID NO:4; the exon 10/exon 11 junction of nucleotides 1240 and 1241 of SEQ ID NO:4: the exon 11/exon 12 junction of nucleotides 1366 and 1367 of SEQ ID NO:4; the exon 12/exon 13 junction of nucleotides 1411 and 1412 of SEQ ID NO:4; the exon 13/exon 14 junction of nucleotides 1491 and 1492 of SEQ ID NO:4; the exon 14/exon 15 junction of nucleotides 1604 and 1605 of SEQ ID NO:4; the exon 15/exon 16 junction of nucleotides 1788 and 1789 of SEQ ID NO:4; the exon 16/exon 17 junction of nucleotides 1873 and 1874 of SEQ ID NO:4; the exon 17/exon 18 junction of nucleotides 2019 and 2020 of SEQ ID NO:4; the exon 18/exon 19 junction of nucleotides 2110 and 2111 of SEQ ID NO:4; the exon 19/exon 20 junction of nucleotides 2259 and 2260 of SEQ ID NO:4; the exon 20/exon 21 junction of nucleotides 2345 and 2346 of SEQ ID NO:4; the exon 20/exon 22 junction of nucleotides 2415 and 2416 of SEQ ID NO:4; and the exon 22/exon 23 junction of nucleotides 2534 and 2535 of SEQ ID NO:4. Junction nucleotides may be located at any position of the selected SEQ ID NO:4 fragment.

The present invention further relates to polynucleotides that hybridize to the above-described sequences. In this regard, the present invention especially relates to polynucleotides that hybridize under stringent conditions to the above-described polynucleotides. As herein used, the term "stringent conditions" means hybridization will occur only if there is at least 90% and preferably at least 95% identity and more preferably at least 97% identity between the sequences.

Furthermore, a major consideration associated with hybridization analysis of DNA or RNA sequences is the degree of relatedness the probe has with the sequences present in the specimen under study. This is important with a blotting technique (e.g., Southern or Northern Blot), since a moderate degree of sequence homology under nonstringent conditions of hybridization can yield a strong signal even though the probe and sequences in the sample represent non-homologous genes.

The particular hybridization technique is not essential to the invention, any technique commonly used in the art is within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5×Denhardt's (1×Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C. Additionally, if hybridization is to an immobilized nucleic acid, a washing step may be utilized wherein probe binding to polynucleotides of low homology, or nonspecific binding of the probe, may be removed. For example, a stringent wash step may involve a buffer of 0.2×SSC and 0.5% SDS at a temperature of 65° C.

Additional information related to hybridization technology and, more particularly, the stringency of hybridization and washing conditions may be found in Sambrook et al., *Molecular Cloning: A Laboratory Manual*, Second Edition, Cold Spring Harbor Laboratory, Cold Spring Harbor, N.Y. (1989), which is incorporated herein by reference.

Polynucleotides of the invention which are sufficiently identical to a nucleotide sequences contained in SEQ ID NO:1, SEQ ID NO:2, SEQ ID NO:3 or SEQ ID NO:4, or in the cDNA inserts of ATCC Deposit No. 209933, ATCC Deposit No. 209934, ATCC Deposit No. 98809 or ATCC Deposit No. 326637, may be used as hybridization probes for cDNA and genomic DNA, to isolate full-length cDNAs and genomic clones encoding de novo DNA cytosine methyltransferase proteins and to isolate cDNA and genomic clones of other genes that have a high sequence similarity to the de novo DNA cytosine methyltransferase genes. Such hybridization techniques are known to those of skill in the art. Typically, these nucleotide sequences are at least about 90% identical, preferably at least about 95% identical, more preferably at least about 97%, 98% or 99% identical to that of the reference. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

III. Vectors, Host Cells, and Recombinant Expression

The present invention also relates to vectors that comprise a polynucleotide of the present invention, host cells which are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems for polynucleotides of the invention. Introduction of polynucleotides into host cells can be effected by methods described in many standard laboratory manuals, such as Sambrook et al., *Molecular Cloning: A Laboratory Manual,* 2nd Ed., Cold Spring Harbor Laboratory Press, Cold Spring Harbor, N.Y. (1989). For example, calcium phosphate transfection, DEAE-dextran mediated transfection, transvection, microinjection, cationic lipid-mediated transfection, electroporation, transduction, scrape loading, ballistic introduction, infection or any other means known in the art may be utilized.

Representative examples of appropriate hosts include bacterial cells, such as streptococci, staphylococci. *E. coli, Streptomyces* and *Bacillus subtilis* cells; fungal cells, such as yeast cells and *Aspergillus* cells; insert cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophages, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning: A Laboratory Manual* (supra).

RNA vectors may also be utilized for the expression of the de novo DNA cytosine methyltransferases disclosed in this invention. These vectors are based on positive or negative strand RNA viruses that naturally replicate in a wide variety of eukaryotic cells (Bredenbeek, P. J. and Rice, C. M., Virology 3: 297-310, (1992)). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., TIBTECH 11: 18-22, (1993); Frolov, I., et al., *Proc. Natl. Acad. Sci.* (*USA*) 93: 11371-11377, (1996)). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

As used herein, the term "operably linked," when used in the context of a linkage between a structural gene and an expression control sequence, e.g., a promoter, refers to the position and orientation of the expression control sequence relative to the structural gene so as to permit expression of the structural gene in any host cell. For example, an operable linkage would maintain proper reading frame and would not introduce any in frame stop codons.

As used herein, the term "heterologous promoter," refers to a promoter not normally and naturally associated with the structural gene to be expressed. For example, in the context of expression of a de novo DNA cytosine methyltransferase polypeptide, a heterologous promoter would be any promoter other than an endogenous promoter associated with the de novo DNA cytosine methyltransferase gene in non-recombinant mouse or human chromosomes. In specific embodiments of this invention, the heterologous promoter is a prokaryotic or bacteriophage promoter, such as the lac promoter, T3 promoter, or T7 promoter. In other embodiments, the heterologous promoter is a eukaryotic promoter.

In other embodiments, this invention provides an isolated nucleic acid molecule comprising a de novo DNA cytosine methyltransferase structural gene operably linked to a heterologous promoter. As used herein, the term "a de novo DNA cytosine methyltransferase structural gene" refers to a nucleotide sequence at least about 90% identical to one of the following nucleotide sequences:

(a) a nucleotide sequence encoding the de novo DNA cytosine methyltransferase polypeptide having the complete amino acid sequence in SEQ ID NO:5, SEQ ID NO:6, or SEQ ID NO:7;

(b) a nucleotide sequence encoding the de novo DNA cytosine methyltransferase polypeptide having the complete amino acid sequence encoded by the cDNA insert of ATCC Deposit No. 209933, ATCC Deposit No. 209934, or ATCC Deposit No. 98809; or (c) a nucleotide sequence complementary to any of the nucleotide sequences in (a) or (b).

In preferred embodiments, the de novo DNA cytosine methyltransferase structural gene is 90%, and more preferably 91%, 92%, 93%, 94%, 95%, 97%, 98%, 99%, or 100% identical to one or more of nucleotide sequences (a), (b), or (c) supra.

In another embodiment the term "a de novo DNA cytosine methyltransferase structural gene" refers to a nucleotide sequence about 90% to 99% identical to one of the following nucleotide sequences:

(a) a nucleotide sequence encoding the de novo DNA cytosine methyltransferase polypeptide having the complete amino acid sequence in SEQ ID NO:8:

(b) a nucleotide sequence encoding the de novo DNA cytosine methyltransferase polypeptide having the complete amino acid sequence encoded by the cDNA insert of ATCC Deposit No. 326637; or (c) a nucleotide sequence complementary to any of the nucleotide sequences in (a) or (b).

In preferred embodiments, the de novo DNA cytosine methyltransferase structural gene is 90%, and more preferably 91%, 92%, 93%, 94%, 95%, 97%, 98%, or 99% identical to SEQ ID NO:8, ATCC Deposit No. 326637 or polynucleotides complementary thereto.

This invention also provides an isolated nucleic acid molecule comprising a de novo DNA cytosine methyltransferase structural gene operably linked to a heterologous promoter, wherein said isolated nucleic acid molecule does not encode a fusion protein comprising the de novo DNA cytosine methyltransferase structural gene or a fragment thereof.

This invention further provides an isolated nucleic acid molecule comprising a de novo DNA cytosine methyltransferase structural gene operably linked to a heterologous promoter, wherein said isolated nucleic acid molecule is capable of expressing a de novo DNA cytosine methyltransferase polypeptide when used to transform an appropriate host cell.

This invention also provides an isolated nucleic acid molecule comprising a polynucleotide having a nucleotide sequence at least 90%, 91%, 92%, 93%, 94%, 95%, 96%, 97%, 98%, 99%, or 100% identical to a sequence encoding a de novo DNA cytosine methyltransferase polypeptide having the amino acid sequence of SEQ ID NO:5. SEQ ID NO:6, SEQ ID NO:7 or SEQ ID NO:8, wherein said isolated nucleic acid molecule does not contain a nucleotide sequence at least 90% identical to the 3' untranslated region of SEQ ID NO:1 (nucleotides 2942-4191), SEQ ID NO:2 (nucleotides 2847-4174), SEQ ID NO:3 (nucleotides 3090-4397) or SEQ ID NO:4 (nucleotides 2677-4127), or a fragment of the 3' untranslated region greater than 25, 50, 75, 100, or 125 bp in length.

This invention further provides an isolated nucleic acid molecule comprising a polynucleotide having a nucleotide sequence at least 90%, 91%, 92%, 93%, 94%, 95%, 96%, 97%, 98%, 99%, or 100% identical to a sequence encoding a de novo DNA cytosine methyltransferase polypeptide having the amino acid sequence of SEQ ID NO:5. SEQ ID NO:6, SEQ ID NO:7 or SEQ ID NO:8, wherein said isolated nucleic acid molecule does not contain a nucleotide sequence at least 90% identical to the 5' untranslated region of SEQ ID NO:1 (nucleotides 1-216), SEQ ID NO:2 (nucleotides 1-268), SEQ ID NO:3 (nucleotides 1-352) or SEQ ID NO:4 (nucleotides 1-114), or a fragment of the 5' untranslated region greater than 25, 35, 45, 55, 65, 75, 85, or 90 bp.

Suitable known prokaryotic promoters for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), adenovirus promoter, Herpes virus promoter, and metallothionein promoters, such as the mouse metallothionein-I promoter and tissue and organ-specific promoters known in the art.

If the de novo DNA cytosine methyltransferase polypeptide is to be expressed for use in screening assays, generally, it is preferred that the polypeptide be produced at the surface of the cell. In this event, the cells may be harvested prior to use in the screening assay. If de novo DNA cytosine methyltransferase polypeptide is secreted into the medium, the medium can be recovered in order to recover and purify the polypeptide; if produced intracellularly, the cells must first be lysed before the polypeptide is recovered.

De novo DNA cytosine methyltransferase polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

IV. Polypeptides of the Invention

The de novo DNA cytosine methyltransferase polypeptides of the present invention include the polypeptide of SEQ ID NO:5, SEQ ID NO:6, SEQ ID NO:7 or SEQ ID NO:8, as well as polypeptides and fragments which have activity and have at least 90% identity to the polypeptide of SEQ ID NO:5, SEQ ID NO:6, SEQ ID NO:7 or SEQ ID NO:8, or the relevant portion and more preferably at least 96%, 97% or 98% identity to the polypeptide of SEQ ID NO:5, SEQ ID NO:6, SEQ ID NO:7 or SEQ ID NO:8, and still more preferably at least 91%, 92%, 93%, 94%, 95%, 96%, 97%, 98%, 99%, or 100% identity to the polypeptide of SEQ ID NO:5, SEQ ID NO:6, SEQ ID NO:7 or SEQ ID NO:8.

The polypeptides of the present invention are preferably provided in an isolated form.

The polypeptides of the present invention include the polypeptide encoded by the deposited cDNAs; a polypeptide comprising amino acids from about 1 to about 908 in SEQ ID NO:5; a polypeptide comprising amino acids from about 1 to about 859 in SEQ ID NO:6; a polypeptide comprising amino acids from about 1 to about 912 in SEQ ID NO:7 and a polypeptide comprising amino acids from about 1 to about 853 in SEQ ID NO:8; as well as polypeptides which are at least about 90% identical, and more preferably at least about 91%, 92%, 93%, 94%, 95%, 96%, 97%, 98%, 99%, or 100% identical to the polypeptides described above and also include portions of such polypeptides with at least 30 amino acids and more preferably at least 50 amino acids.

Polypeptides of the invention also include alternative splicing variants of the Dnmt3 sequences disclosed herein. For example, alternative variant spliced proteins of mouse Dnmt3b include but are not limited to a polypeptide wherein, except for at least one conservative amino acid substitution, said polypeptide has a sequence selected from the group consisting of: (1) amino acid residues 1 to 362 and 383 to 859 from SEQ ID NO:2; and (2) amino acid residues 1 to 362 and 383 to 749 and 813 to 859 from SEQ ID NO:2; and alternative variant spliced proteins of human DNMT3B include but are not limited to a polypeptide wherein, except for at least one conservative amino acid substitution, said polypeptide has a sequence selected from the group consisting of: (1) amino acid residues 1 to 355 and 376 to 853 from SEQ ID NO:4; and (2) amino acid residues 1 to 355 and 376 to 743 and 807 to 853 from SEQ ID NO:4.

The de novo DNA cytosine methyltransferase polypeptides may be a part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

Biologically active fragments of the de novo DNA cytosine methyltransferase polypeptides are also included in the invention. A fragment is a polypeptide having an amino acid sequence that entirely is the same as part but not all of the amino acid sequence of one of the aforementioned de novo DNA cytosine methyltransferase polypeptides. As with de novo DNA cytosine methyltransferase polypeptides, fragments may be "free-standing," or comprised within a larger polypeptide of which they form a part or region, most preferably as a single continuous region. In the context of this invention, a fragment may constitute from about 10 contiguous amino acids identified in SEQ ID NO:5, SEQ ID NO:6. SEQ ID NO:7 or SEQ ID NO:8. More specifically, polypeptide fragment lengths may be defined algebraically as follows: (a) for SEQ ID NO:5, as 10+N, wherein N equals zero or any positive integer up to 898; (b) for SEQ ID NO:6, as 10+N, wherein N equals zero or any positive integer up to 849; (c) for SEQ ID NO:7, as 10+N, wherein N equals zero or any positive integer up to 902; and (d) for SEQ ID NO:8, as 10+N, wherein N equals zero or any positive integer up to 843.

Preferred fragments include, for example, truncation polypeptides having the amino acid sequence of de novo DNA cytosine methyltransferase polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate protein activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 90% identical to that of SEQ ID NO:5, SEQ ID NO:6, SEQ ID NO:7 or SEQ ID NO:8, or fragments thereof with at least 90% identity to the corresponding fragment of SEQ ID NO:5, SEQ ID NO:6, SEQ ID NO:7 or SEQ ID NO:8, all of which retain the biological activity of the de novo DNA cytosine methyltransferase protein, including antigenic activity. Included in this group are variants of the defined sequence and fragment. Preferred variants are those that vary from the reference by conservative amino acid substitutions, i.e. those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. Particularly preferred are variants in which several, 5 to 10, 1 to 5, or 1 to 2 amino acids are substituted, deleted, or added in any combination.

The de novo DNA cytosine methyltransferase polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

V. In Vitro DNA Methylation

One preferred embodiment of the invention enables the in vitro methylation at the C5 position of cytosine in DNA. The starting substrate DNA may be hemimethylated (i.e., one strand of the duplex DNA is methylated) or may lack methylation completely. The polypeptides of the invention, being de novo DNA cytosine methyltransferases, are uniquely suited to the latter function, owing to the fact that, unlike maintenance methyltransferases, their preferred substrate is not hemimethylated DNA.

As exemplified in Examples 7 and 8, isolated polypeptides of the invention function as in vitro DNA methyltransferases when combined in an appropriately buffered solution with the appropriate cofactors and a substrate DNA. The substrate DNA may be selected from any natural source, e.g., genomic DNA, or a recombinant source such as a DNA fragment amplified by the polymerase chain reaction. The substrate DNA may be prokaryotic or eukaryotic DNA. In a preferred embodiment, the substrate DNA is mammalian DNA, and most preferredly, the substrate DNA is human DNA.

It will be well appreciated by those in the art that in vitro methylation of DNA may be used to direct or regulate the expression of said DNA in a biological system. For example, over-expression, under-expression or lack of expression of a particular native DNA sequence in a host cell or organism may be attributed to the fact that the DNA is undermethylated (hypomethylated) or not methylated. Thus, in vitro methylation of a recombinant form of said DNA, and the subsequent introduction of the methylated, recombinant DNA into the cell or organism, may effect an increase or decrease in the expression of the encoded polypeptide.

Also, it will be readily apparent to the skilled artisan that the in vitro methylation pattern will be maintained after introduction into a biological system by the action of maintenance methyltransferase polypeptides in said system.

In one embodiment of the invention, the biological system selected for the introduction of in vitro methylated DNA may be prokaryotic or eukaryotic. In a preferred embodiment, the biological system is mammalian, and the most preferred embodiment is when the biological system is human.

Methods for introducing the in vitro methylated DNA into the biological system are well known in the art, and the skilled artisan will recognize that the in vitro methylation of DNA may be a preliminary step to any system of gene therapy detailed herein.

VI. Genetic Screening and Diagnostic Assays

To map the human chromosome locations, the GenBank STS database was searched using Dnmt3a and Dnmt3b sequences as queries. The search identified markers WI-6283 (GenBank Accession number G06200) and SHGC-15969 (GenBank Accession number G15302) as matching the cDNA sequence of Dnmt3a and Dnmt3b, respectively. WI-6283 has been mapped to 2p23 between D2S171 and D2S174 (48-50 cM) on the radiation hybrid map by Whitehead Institute/MIT Center for Genome Research. The corresponding mouse chromosome location is at 4.0 cM on chromosome 12. SHGC-15969 has been mapped to 20 pl 1.2 between D20S184 and D20S106 (48-50 cM) by Stanford Human Genome Center. The corresponding mouse chromosome locus is at 84.0 cM on chromosome 2.

These data are valuable as markers to be correlated with genetic map data. Such data are found, for example, in V. McKusick, Mendelian Inheritance in Man (available on-line through Johns Hopkins, University Welch Medical Library). The relationship between genes and diseases that have been mapped to the same chromosomal region are then identified through linkage analysis (coinheritence of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

This invention also relates to the use of de novo DNA cytosine methyltransferase polynucleotides for use as diagnostic reagents. Detection of a mutated form of a de novo DNA cytosine methyltransferase gene associated with a dysfunction will provide a diagnostic tool that can add to or define a diagnosis of a disease or susceptibility to a disease which results from under-expression, over-expression or altered expression of the mutated de novo DNA cytosine methyltransferase. Individuals carrying mutations in one or more de novo DNA cytosine methyltransferase genes may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled de novo DNA cytosine methyltransferase nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers, et al., *Science* 230:1242 (1985)). Sequence changes at specific locations may also be revealed by nuclease protection assays, such as RNase and S1 protection or the chemical cleavage method (see Cotton, et al., *Proc. Natl. Acad. Sci. USA* 85:4397-4401 (1985)).

The diagnostic assays offer a process for diagnosing or determining a susceptibility to neoplastic disorders through detection of mutations in one or more de novo DNA cytosine methyltransferase genes by the methods described.

In addition, neoplastic disorders may be diagnosed by methods that determine an abnormally decreased or increased level of de novo DNA cytosine methyltransferase polypeptide or de novo DNA cytosine methyltransferase mRNA in a sample derived from a subject. Decreased or increased expression may be measured at the RNA level using any of the methods well known in the art for the quantitation of polynucleotides; for example, RT-PCR, RNase protection, Northern blotting and other hybridization methods may be utilized. Assay techniques that may be used to determine the level of a protein, such as an de novo DNA cytosine methyltransferase protein, in a sample derived from a host are well known to those of skill in the art. Such assay methods include radioimmunoassays, competitive-binding assays, Western blot analysis and ELISA assays.

Additionally, methods are provided for diagnosing or determining a susceptibility of an individual to neoplastic disorders, comprising (a) assaying the de novo DNA cytosine methyltransferase protein gene expression level in mammalian cells or body fluid; and (b) comparing said de novo DNA cytosine methyltransferase protein gene expression level with a standard de novo DNA cytosine methyltransferase protein gene expression level whereby an increase or decrease in said de novo DNA cytosine methyltransferase gene expression level over said standard is indicative of an increased or decreased susceptibility to a neoplastic disorder.

VII. De Novo DNA Cytosine Methyltransferase Antibodies

The polypeptides of the invention or their fragments or analogs thereof, or cells expressing them may also be used as immunogens to produce antibodies immunospecific for the de novo DNA cytosine methyltransferase polypeptides. By "immunospecific" is meant that the antibodies have affinities for the polypeptides of the invention that are substantially greater in their affinities for related polypeptides such as the analogous proteins of the prior art.

Antibodies generated against the de novo DNA cytosine methyltransferase polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature 256:495-497 (1975)), the trioma technique, the human B-cell hybridoma technique (Kozbor, et al. *Immunology Today* 4:72 (1983)) and the EBV-hybridoma technique (Cole, et al., *Monoclonal Antibodies and Cancer Therapy*, pp. 77-96, Alan R. Liss, Inc., (1985)).

Techniques for the production of single chain antibodies (U.S. Pat. No. 4,946,778) may also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against de novo DNA cytosine methyltransferase polypeptides may also be employed to treat neoplastic disorders, among others.

VIII. Agonist and Antagonist Screening

The de novo DNA cytosine methyltransferase polypeptides of the present invention may be employed in a screening process for compounds which bind one of the proteins and which activate (agonists) or inhibit activation of (antagonists) one of the polypeptides of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics (see Coligan, et al., *Current Protocols in Immunology* 1(2):Chapter 5 (1991)).

By "agonist" is intended naturally occurring and synthetic compounds capable of enhancing a de novo DNA cytosine methyltransferase activity (e.g., increasing the rate of DNA methylation). By "antagonist" is intended naturally occurring and synthetic compounds capable of inhibiting a de novo DNA cytosine methyltransferase activity.

DNA methylation is an important, fundamental regulatory mechanism for gene expression, and, therefore, the methylated state of a particular DNA sequence may be associated with many pathologies. Accordingly, it is desirous to find both compounds and drugs which stimulate de novo DNA cytosine methyltransferase activity and which can inhibit the function of de novo DNA cytosine methyltransferase protein. In general, agonists are employed for therapeutic and prophylactic purposes including the treatment of ceratin types of neoplastic disorders. For example, de novo methylation of growth regulatory genes in somatic tissues is associated with tumorigenesis in humans (Laird, P. W. and Jaenisch, R. *Ann. Rev. Genet.* 30:441-464 (1996); Baylin, S. B. et al., *Adv. Cancer. Res.* 72:141-196 (1998); and Jones, P. A. and Gonzalgo, M. L. *Proc. Natl. Acad. Sci. USA* 94:2103-2105 (1997)).

In general, such screening procedures involve producing appropriate cells which express the polypeptide of the present invention. Such cells include cells from mammals, yeast, *Drosophila* or *E. coli*. Cells expressing the protein (or cell membrane containing the expressed protein) are then contacted with a test compound to observe binding, stimulation or inhibition of a functional response.

Alternatively, the screening procedure may be an in vitro procedure in which the activity of isolated DNMT3 protein is tested in the presence of a potential agonist or antagonist of DNMT3 de novo DNA cytosine methyltransferase activity. Such in vitro assays are known to those skilled in the art, and by way of example are demonstrated in Example 4.

The assays may simply test binding of a candidate compound wherein adherence to the cells bearing the protein is detected by means of a label directly or indirectly associated with the candidate compound or in an assay involving competition with a labeled competitor. Further, these assays may test whether the candidate compound affects activity of the protein, using detection systems appropriate to the cells bearing the protein at their surfaces. Inhibitors of activation are generally assayed in the presence of a known agonist and the effect on activation by the agonist in the presence of the candidate compound is observed. Standard methods for conducting such screening assays are well understood in the art.

Examples of potential de novo DNA cytosine methyltransferase protein antagonists include antibodies or, in some cases, oligonucleotides or proteins which are closely related to the substrate of the de novo DNA cytosine methyltransferase protein, e.g., small molecules which bind to the protein so that the activity of the protein is prevented.

IX. Gene Therapy Applications

For overview of gene therapy, see Strachan, T. & Read A. P., Chapter 20, "Gene Therapy and Other Molecular Genetic-based Therapeutic Approaches," (and references cited therein) in *Human Molecular Genetics*, BIOS Scientific Publishers Ltd. (1996).

Initial research in the area of gene therapy focused on a few well-characterized and highly publicized disorders: cystic fibrosis (Drumm, M. L. et al, *Cell* 62:1227-1233 (1990); Gregory, R. J. et al. *Nature* 347:358-363 (1990); Rich, D. P. et al. *Nature* 347:358-363 (1990)); and Gaucher disease (Sorge, J. et al., *Proc. Natl. Acad. Sci.* (*USA*) 84:906-909 (1987); Fink, J. K. et al., *Proc. Natl. Acad. Sci.* (*USA*) 87:2334-2338 (1990)); and certain forms of hemophilia- Bontempo, F. A. et al., *Blood* 69:1721-1724 (1987); Palmer, T. D. et al., *Blood* 73:438-445 (1989); Axelrod, J. H. et al. *Proc. Natl. Acad. Sci.* (*USA*) 87:5173-5177 (1990); Armentano. D. et al., *Proc. Natl. Acad. Sci.* (*USA*) 87:6141-6145 (1990)); and muscular dystrophy (Partridge, T. A. et al., *Nature* 337:176-179 (1989); Law, P. K. et al., *Lancet* 336: 114-115 (1990); Morgan, J. E. et al., *J. Cell Biol.* 111:2437-2449 (1990)).

More recently, the application of gene therapy in the treatment of a wider variety of disorders is progressing, for example: cancer (Runnebaum, I. B., *Anticancer Res.* 17(4B): 2887-2890, (1997)), heart disease (Rader, D. J., *Int. J. Clin. Lab. Res.* 27(1): 35-43, (1997); Malosky, S., *Curr. Opin. Cardiol.* 11(4): 361-368, (1996)), central nervous system disorders and injuries (Yang, K., et al., *Neurotrauma J.* 14(5): 281-297, (1997); Zlokovic. B. V. et al. *Neurosurgery* 40(4): 789-803, (1997); Zlokovic, B. V., et al. *Neurosurgery* 40(4): 805-812, (1997)), vascular diseases (Clowes, A. W., *Thromb. Haemost.* 78(1): 605-610, 1997), muscle disorders (Douglas. J. T., et al., *Neuromuscul. Disord.* 7(5):

284-298, (1997); Huard, J., et al., *Neuromuscul. Disord* 7(5): 299-313, (1997)), rheumatoid arthritis (Evans, C. H., et al., *Curr. Opin. Rheumatol.* 8(3): 230-234, (1996)) and epithelial tissue disorders (Greenhalgh, D. A., et al., *Invest Dermatol. J.* 103(5 Suppl.): 63S-93S, (1994)).

In a preferred approach, one or more isolated nucleic acid molecules of the invention are introduced into or administered to the animal. Such isolated nucleic acid molecules may be incorporated into a vector or virion suitable for introducing the nucleic acid molecules into the cells or tissues of the animal to be treated, to form a transfection vector. Techniques for the formation of vectors or virions comprising the de novo DNA cytosine methyltransferase-encoding nucleic acid molecules are well known in the art and are generally described in "Working Toward Human Gene Therapy," Chapter 28 *in Recombinant DNA,* 2nd Ed., Watson, J. D. et al., eds., New York: Scientific American Books, pp. 567-581 (1992). An overview of suitable vectors or virions is provided in an article by Wilson, J. M. (*Clin. Exp. Immunol.* 107(Suppl. 1): 31-32, (1997)). Such vectors are derived from viruses that contain RNA (Vile, R. G., et al., *Br. Med Bull.* 51(1): 12-30, (1995)) or DNA (Ali M. et al. *Gene Ther.* 1(6): 367-384, (1994)). Example vector systems utilized in the art include the following: retroviruses (Vile, R. G. supra.), adenoviruses (Brody. S. L. et al., *Ann. N.Y. Acad. Sci.* 716: 90-101, (1994)), adenoviral/retroviral chimeras (Bilbao, G., et al., *FASEB J.* 11 (8): 624-634, (1997)), adeno-associated viruses (Flotte, T. R. and Carter, B. J., *Gene Ther.* 2(6): 357-362, (1995)), herpes simplex virus (Latchman, D. S., *Mol. Biotechnol.* 2(2): 179-195, (1994)), Parvovirus (Shaughnessy, E., et al., *Semin Oncol.* 23(1): 159-171. (1996)) and reticuloendotheliosis virus (Donburg, R., *Gene Therap.* 2(5): 301-310, (1995)). Also of interest in the art, the development of extrachromosomal replicating vectors for gene therapy (Calos, M. P., *Trends Genet.* 12(11): 463-466, (1996)).

Other, nonviral methods for gene transfer known in the art (Abdallah, B. et al., *Biol. Cell* 85(1): 1-7, (1995)) might be utilized for the introduction of de novo DNA cytosine methyltransferase polynucleotides into target cells; for example, receptor-mediated DNA delivery (Philips, S. C., *Biologicals* 23(1): 13-16, (1995)) and lipidic vector systems (Lee, R. J. and Huang, L., *Crit. Rev. Ther. Drug Carrier Syst.* 14(2): 173-206, (1997)) are promising alternatives to viral-based delivery systems.

General methods for construction of gene therapy vectors and the introduction thereof into affected animals for therapeutic purposes may be obtained in the above-referenced publications, the disclosures of which are specifically incorporated herein by reference in their entirety. In one such general method, vectors comprising the isolated polynucleotides of the present invention are directly introduced into target cells or tissues of the affected animal, preferably by injection, inhalation, ingestion or introduction into a mucous membrane via solution; such an approach is generally referred to as "in vivo" gene therapy. Alternatively, cells, tissues or organs may be removed from the affected animal and placed into culture according to methods that are well-known to one of ordinary skill in the art; the vectors comprising the de novo DNA cytosine methyltransferase polynucleotides may then be introduced into these cells or tissues by any of the methods described generally above for introducing isolated polynucleotides into a cell or tissue, and, after a sufficient amount of time to allow incorporation of the de novo DNA cytosine methyltransferase polynucleotides, the cells or tissues may then be re-inserted into the affected animal. Since the introduction of a De novo DNA cytosine methyltransferase gene is performed outside of the body of the affected animal, this approach is generally referred to as "ex vivo" gene therapy.

For both in vivo and ex vivo gene therapy, the isolated de novo DNA cytosine methyltransferase polynucleotides of the invention may alternatively be operatively linked to a regulatory DNA sequence, which may be a de novo DNA cytosine methyltransferase promoter or an enhancer, or a heterologous regulatory DNA sequence such as a promoter or enhancer derived from a different gene, cell or organism, to form a genetic construct as described above. This genetic construct may then be inserted into a vector, which is then used in a gene therapy protocol. The need for transcriptionally targeted and regulatable vectors providing cell-type specific and inducible promoters is well recognized in the art (Miller, N. and Whelan, J., *Hum. Gene Therap.* 8(7): 803-815, (1997); and Walther, W. and Stein, U., *Mol. Med. J,* 74(7): 379-392, (1996)), and for the purposes of de novo DNA cytosine methyltransferase gene therapy, is incorporated herein by reference.

The construct/vector may be introduced into the animal by an in vivo gene therapy approach, e.g., by direct injection into the target tissue, or into the cells or tissues of the affected animal in an ex vivo approach. In another preferred embodiment, the genetic construct of the invention may be introduced into the cells or tissues of the animal, either in vivo or ex vivo, in a molecular conjugate with a virus (e.g., an adenovirus or an adeno-associated virus) or viral components (e.g., viral capsid proteins; see WO 93/07283). Alternatively, transfected host cells, which may be homologous or heterologous, may be encapsulated within a semipermeable barrier device and implanted into the affected animal, allowing passage of de novo DNA cytosine methyltransferase polypeptides into the tissues and circulation of the animal but preventing contact between the animal's immune system and the transfected cells (see WO 93/09222). These approaches result in increased production of de novo DNA cytosine methyltransferase by the treated animal via (a) random insertion of the de novo DNA cytosine methyltransferase gene into the host cell genome; or (b) incorporation of the de novo DNA cytosine methyltransferase gene into the nucleus of the cells where it may exist as an extrachromosomal genetic element. General descriptions of such methods and approaches to gene therapy may be found, for example, in U.S. Pat. No. 5,578, 461, WO 94/12650 and WO 93/09222.

Antisense oligonucleotides have been described as naturally occurring biological inhibitors of gene expression in both prokaryotes (Mizuno et al., *Proc. Natl. Acad. Sci. USA* 81:1966-1970 (1984)) and eukaryotes (Heywood, *Nucleic Acids Res.* 14:6771-6772 (1986)), and these sequences presumably function by hybridizing to complementary mRNA sequences, resulting in hybridization arrest of translation (Paterson, et al., *Proc. Natl. Acad. Sci. USA,* 74:4370-4374 (1987)).

Thus, another gene therapy approach utilizes antisense technology. Antisense oligonucleotides are short synthetic DNA or RNA nucleotide molecules formulated to be complementary to a specific gene or RNA message. Through the binding of these oligomers to a target DNA or mRNA sequence, transcription or translation of the gene can be selectively blocked and the disease process generated by that gene can be halted (see, for example, Jack Cohen, *Oligodeoxynucleotides, Antisense Inhibitors of Gene Expression,* CRC Press (1989)). The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, et al, *J. Natl. Cancer Inst.* 81:1539-1544 (1989)).

Antisense therapy is the administration of exogenous oligonucleotides which bind to a target polynucleotide located within the cells. For example, antisense oligonucleotides may be administered systemically for anticancer therapy (Smith, International Application Publication No. WO 90/09180).

The antisense oligonucleotides of the present invention include derivatives such as S-oligonucleotides (phosphorothioate derivatives or S-oligos, see, Jack Cohen, supra). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., *J. Org. Chem.* 55:4693-4698 (1990); and Iyer et al., *J. Am. Chem. Soc.* 112:1253-1254 (1990), the disclosures of which are fully incorporated by reference herein.

As described herein, sequence analysis of SEQ ID NO:1, SEQ ID NO:2, SEQ ID NO:3 or the SEQ ID NO:4 cDNA clone shows that sequence that is nonhomologous to known DNA methyltransferase sequences may be identified (see FIGS. 1 and 4). Thus, the antisense oligonucleotides of the present invention may be RNA or DNA that is complementary to and stably hybridize with such sequences that are specific for a de novo DNA cytosine methyltransferase gene of the invention. Use of an oligonucleotide complementary to such regions allows for selective hybridization to a de novo DNA cytosine methyltransferase mRNA and not to an mRNA encoding a maintenance methyltransferase protein.

Preferably, the antisense oligonucleotides of the present invention are a 15 to 30-mer fragment of the antisense DNA molecule coding for unique sequences of the de novo DNA cytosine methyltransferase cDNAs. Preferred antisense oligonucleotides bind to the 5'-end of the de novo DNA cytosine methyltransferase mRNAs. Such antisense oligonucleotides may be used to down regulate or inhibit expression of the gene.

Other criteria that are known in the art may be used to select the antisense oligonucleotides, varying the length or the annealing position in the targeted sequence.

Included as well in the present invention are pharmaceutical compositions comprising an effective amount of at least one of the antisense oligonucleotides of the invention in combination with a pharmaceutically acceptable carrier. In one embodiment, a single antisense oligonucleotide is utilized.

In another embodiment, two antisense oligonucleotides are utilized which are complementary to adjacent regions of the genome. Administration of two antisense oligonucleotides that are complementary to adjacent regions of the genome or corresponding mRNA may allow for more efficient inhibition of genomic transcription or mRNA translation, resulting in more effective inhibition of protein or mRNA production.

Preferably, the antisense oligonucleotide is coadministered with an agent which enhances the uptake of the antisense molecule by the cells. For example, the antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety (see also U.S. Pat. Nos. 4,235,871, 4,231,877, 4,224,179, 4,753,788, 4,673,567, 4,247,411, and 4,814,270 for general methods of preparing liposomes comprising biological materials).

Alternatively, the antisense oligonucleotide may be combined with a lipophilic carrier such as any one of a number of sterols including cholesterol, cholate and deoxycholic acid. A preferred sterol is cholesterol.

In addition, the antisense oligonucleotide may be conjugated to a peptide that is ingested by cells. Examples of useful peptides include peptide hormones, antigens or antibodies, and peptide toxins. By choosing a peptide that is selectively taken up by the targeted tissue or cells, specific delivery of the antisense agent may be effected. The antisense oligonucleotide may be covalently bound via the 5'OH group by formation of an activated aminoalkyl derivative. The peptide of choice may then be covalently attached to the activated antisense oligonucleotide via an amino and sulfhydryl reactive hetero bifunctional reagent. The latter is bound to a cysteine residue present in the peptide. Upon exposure of cells to the antisense oligonucleotide bound to the peptide, the peptidyl antisense agent is endocytosed and the antisense oligonucleotide binds to the target mRNA to inhibit translation (Haralambid et al., WO 8903849 and Lebleu et al., EP 0263740).

The antisense oligonucleotides and the pharmaceutical compositions of the present invention may be administered by any means that achieve their intended purpose. For example, administration may be by parenteral, subcutaneous, intravenous, intramuscular, intraperitoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the antisense oligonucleotide is contained in an amount effective to achieve the desired effect, for example, inhibition of proliferation and/or stimulation of differentiation of the subject cancer cells. While individual needs vary, determination of optimal ranges of effective amounts of each component is with the skill of the art.

Alternatively, antisense oligonucleotides can be prepared which are designed to interfere with transcription of the gene by binding transcribed regions of duplex DNA (including introns, exons, or both) and forming triple helices (e.g., see Froehler et al. WO 91/06626 or Toole, WO 92/10590). Preferred oligonucleotides for triple helix formation are oligonucleotides which have inverted polarities for at least two regions of the oligonucleotide (Id.). Such oligonucleotides comprise tandem sequences of opposite polarity such as 3' - - - 5'-L-5' - - - 3', or 5' - - - 3'-L-3' - - - 5', wherein L represents a 0-10 base oligonucleotide linkage between oligonucleotides. The inverted polarity form stabilizes single-stranded oligonucleotides to exonuclease degradation (Froehler et al., supra). The criteria for selecting such inverted polarity oligonucleotides is known in the art, and such preferred triple helix-forming oligonucleotides of the invention are based upon SEQ ID NO:1, SEQ ID NO:2, SEQ ID NO:3 or SEQ ID NO:4.

In therapeutic application, the triple helix-forming oligonucleotides can be formulated in pharmaceutical preparations for a variety of modes of administration, including systemic or localized administration, as described above.

The antisense oligonucleotides of the present invention may be prepared according to any of the methods that are well known to those of ordinary skill in the art, as described above.

Ribozymes provide an alternative method to inhibit mRNA function. Ribozymes may be RNA enzymes, self-splicing RNAs, and self-cleaving RNAs (Cech et al., *Journal of Biological Chemistry* 267:17479-17482 (1992)). It is possible to construct de novo ribozymes which have an endonuclease activity directed in trans to a certain target sequence. Since these ribozymes can act on various sequences, ribozymes can be designed for virtually any RNA substrate. Thus, ribozymes are very flexible tools for inhibiting the expression of specific genes and provide an alternative to antisense constructs.

A ribozyme against chloramphenicol acetyltransferase mRNA has been successfully constructed (Haseloffet al., *Nature* 334:585-591 (1988); Uhlenbeck et al., *Nature* 328:596-600 (1987)). The ribozyme contains three structural domains: 1) a highly conserved region of nucleotides which flank the cleavage site in the 5' direction; 2) the highly conserved sequences contained in naturally occurring cleavage domains of ribozymes, forming a base-paired stem; and 3) the regions which flank the cleavage site on both sides and ensure the exact arrangement of the ribozyme in relation to the cleavage site and the cohesion of the substrate and enzyme. RNA enzymes constructed according to this model have already proved suitable in vitro for the specific cleaving of RNA sequences (Haseloff et al., supra).

Alternatively, hairpin ribozymes may be used in which the active site is derived from the minus strand of the satellite RNA of tobacco ring spot virus (Hampel et al., *Biochemistry* 28:4929-4933 (1989)). Recently, a hairpin ribozyme was designed which cleaves human immunodeficiency virus type 1 RNA (Ojwang et al. *Proc. Natl. Acad. Sci. USA* 89:10802-10806 (1992)). Other self-cleaving RNA activities are associated with hepatitis delta virus (Kuo et al., J. Virol. 62:4429-4444 (1988)).

As discussed above, preferred targets for ribozymes are the de novo DNA cytosine methyltransferase nucleotide sequences that are not homologous with maintenance methyltransferase sequences such as Dnmt 1 or Dnmt 2. Preferably, the ribozyme molecule of the present invention is designed based upon the chloramphenicol acetyltransferase ribozyme or hairpin ribozymes, described above. Alternatively, ribozyme molecules are designed as described by Eckstein et al. (International Publication No. WO 92/07065) who disclose catalytically active ribozyme constructions which have increased stability against chemical and enzymatic degradation, and thus are useful as therapeutic agents.

In an alternative approach, an external guide sequence (EGS) can be constructed for directing the endogenous ribozyme, RNase P, to intracellular mRNA, which is subsequently cleaved by the cellular ribozyme (Altman et al., U.S. Pat. No. 5,168,053). Preferably, the EGS comprises a ten to fifteen nucleotide sequence complementary to an mRNA and a 3'-NCCA nucleotide sequence, wherein N is preferably a purine (Id.). After EGS molecules are delivered to cells, as described below, the molecules bind to the targeted mRNA species by forming base pairs between the mRNA and the complementary EGS sequences, thus promoting cleavage of mRNA by RNase P at the nucleotide at the 5' side of the base-paired region (Id.).

Included as well in the present invention are pharmaceutical compositions comprising an effective amount of at least one ribozyme or EGS of the invention in combination with a pharmaceutically acceptable carrier. Preferably, the ribozyme or EGS is coadministered with an agent which enhances the uptake of the ribozyme or EGS molecule by the cells. For example, the ribozyme or EGS may be combined with a lipophilic cationic compound which may be in the form of liposomes, as described above. Alternatively, the ribozyme or EGS may be combined with a lipophilic carrier such as any one of a number of sterols including cholesterol, cholate and deoxycholic acid. A preferred sterol is cholesterol.

The ribozyme or EGS, and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired. For example, as much as 700 milligrams of antisense oligodeoxynucleotide has been administered intravenously to a patient over a course of 10 days (i.e., 0.05 mg/kg/hour) without signs of toxicity (Sterling, "Systemic Antisense Treatment Reported," *Genetic Engineering News* 12(12):1, 28 (1992)).

Compositions within the scope of this invention include all compositions wherein the ribozyme or EGS is contained in an amount which is effective to achieve inhibition of proliferation and/or stimulate differentiation of the subject cancer cells, or alleviate AD. While individual needs vary, determination of optimal ranges of effective amounts of each component is with the skill of the art.

In addition to administering the antisense oligonucleotides, ribozymes, or EGS as a raw chemical in solution, the therapeutic molecules may be administered as part of a pharmaceutical preparation containing suitable pharmaceutically acceptable carriers comprising excipients and auxiliaries which facilitate processing of the antisense oligonucleotide, ribozyme, or EGS into preparations which can be used pharmaceutically.

Suitable formulations for parenteral administration include aqueous solutions of the antisense oligonucleotides, ribozymes, EGS in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Alternatively, antisense RNA molecules, ribozymes, and EGS can be coded by DNA constructs which are administered in the form of virions, which are preferably incapable of replicating in vivo (see, for example, Taylor, WO 92/06693). For example, such DNA constructs may be administered using herpes-based viruses (Gage et al., U.S. Pat. No. 5,082,670). Alternatively, antisense RNA sequences, ribozymes, and EGS can be coded by RNA constructs which are administered in the form of virions, such as retroviruses. The preparation of retroviral vectors is well known in the art (see, for example, Brown et al., "Retroviral Vectors," in *DNA Cloning: A Practical Approach*, Volume 3, IRL Press, Washington, D.C. (1987)).

Specificity for gene expression may be conferred by using appropriate cell-specific regulatory sequences, such as cell-specific enhancers and promoters. Such regulatory elements are known in the art, and their use enables therapies designed to target specific tissues, such as liver, lung, prostate, kidney, pancreas, etc., or cell populations, such as lymphocytes, neurons, mesenchymal, epithelial, muscle, etc.

In addition to the above noted methods for inhibiting the expression of the de novo methyltransferase genes of the invention, gene therapeutic applications may be employed to provide expression of the polypeptides of the invention.

EXAMPLES

Example 1

Cloning and Sequence Analysis of the Mouse Dnmt3a and Dnmt3b and the Human DNMT3A and DNMT3B Genes and Polypeptides In search of a mammalian de novo DNA methyltransferase, two independent approaches were undertaken, based on the assumption that an unknown mammalian DNA methyltransferase must contain the highly conserved cytosine methyltransferase motifs in the catalytic domain of known methyltransferases (Lauster, R. et al., *J. Mol. Biol.* 206:305-312 (1989) and Kumar. S. et al. *Nucl. Acids Res.* 22:1-10 (1994)). Our first approach, an RT/PCR-based screening using oligonucleotide primers corresponding to the conserved motifs of the known cytosine DNA methyltransferases, failed to detect any novel methyltransferase gene from Dnmt1 null ES cells (data not shown).

The second approach was a tblastn search of the dbEST database using full length bacterial cytosine methyltransferase sequences as queries.

A search of the dbEST database was performed with the tblastn program (Altschul, S. F. et al, *J. Mol. Biol.* 215:403-410 (1990)) using bacterial cytosine methyltransferases as queries. Candidate EST sequences were used one by one as queries to search the non-redundant protein sequence database in GenBank with the blastx program. This process would eliminate EST clones corresponding to known genes (including known DNA methyltransferases) and those which show a higher similarity to other sequences than to DNA methyltransferases. Two EST clones (GenBank numbers W76111 and N88352) were found after the initial search. Two more EST sequences (fl2227 and T66356) were later found after a blastn search of dbEST with the EST sequence of W76111 as a query. Two of the EST clones (W76111 and T66356) were deposited by the I.M.A.G.E. Consortium (Lawrence Livermore National Laboratory, Livermore, Calif.) and obtained from American Type Culture Collection (Manassas, Va.). Sequencing of these two cDNA clones revealed that they were partial cDNA clones with large open reading frames corresponding to two related genes. The translated amino acid sequences revealed the presence of the highly conserved motifs characteristic of DNA cytosine methyltransferases. The EST sequences were then used as probes for screening mouse E7.5 embryo and ES cell cDNA libraries and a human heart cDNA library (Clontech, Calif.).

In a screening of the dbEST database using 35 bacterial cytosine-5 DNA methyltransferase sequences as queries, eight EST clones were found to have the highest similarity but not to be identical to the known cytosine-5-DNA methyltransferase genes. Six of the eight EST sequences were deposited by the I.M.A.G.E. Consortium (Lawrence Livermore National Laboratory, Livermore, Calif.) and obtained from TIGR/ATCC (American Type Culture Collection, Manassas, Va.). Sequencing of these 6 cDNA clones revealed that they were partial cDNA clones with large open reading frames corresponding to three novel genes. The translated amino acid sequences revealed the presence of the highly conserved motifs characteristic of DNA cytosine methyltransferases. The EST sequences were then used as probes for screening a mouse ES cell cDNA library, a mouse E11.5 embryonic cDNA library (Clontech, Calif.) and human heart cDNA library.

Human and mouse cDNA libraries were screened using EST sequences as probes. Sequencing analysis of several independent cDNA clones revealed that two homologous genes were present in both human and mouse. This was further confirmed by Southern analysis of genomic DNA, intron/exon mapping and sequencing of genomic DNA (data not shown). The full length mouse cDNAs for each gene were assembled and complete sequencing revealed that both genes contained the highly conserved cytosine methyltransferase motifs and shared overall 51% of amino acid identity (76% identity in the catalytic domain) (FIG. 3). Since these two genes showed little sequence similarities to Dnmt1 (Bestor, T. H. et al, *J. Mol. Biol.* 203:971-983 (1988) and Yen, R-W. C. et al., *Nucleic Acids Res.* 20:2287-2291 (1992)) and a recently cloned putative DNA methyltransferase gene, Dnmt2 (see Yoder, J. A. and Bestor, T. H. *Hum. Mol. Genet.* 7:279-284 (1998) and Okano, M., Xie, S. and Li, E., (submitted)), beyond the conserved methyltransferase motifs in the catalytic domain, they were named Dnmt3a and Dnmt3b.

The full length Dnmt3a and Dnmt3b genes encode 908 and 859 amino acid polypeptides, termed Dnmt3a and Dnmt3b1, respectively. Nucleotide and amino acid sequences of each are presented in FIGS. 1A, 1B, 2A, and 2B. The Dnmt3b gene also produces through alternative splicing at least two shorter isoforms of 840 and 777 amino acid residues, termed Dnmt3b2 and Dnmt3b3, respectively, (FIG. 4).

To obtain full length human cDNA, fetal heart and fetal testis cDNA libraries were screened using EST clones as probes. Sequencing analysis of several overlapping DNMT3A cDNA clones indicates that the DNMT3A gene encodes a polypeptide of 912 amino acid residues. DNMT3 B cDNA clones were not detected in the fetal heart library, but several DNMT3B cDNA clones were obtained after screening the fetal testis library. PCR screening of large cDNA clones from 24 human tissues was also performed using the Human Rapid-Screen™ cDNA Library Panels (OriGene Technologies, Md.). The largest cDNA clone contained a 4.2 kb insert from a small intestine cDNA library. Sequencing analysis of overlapping cDNA clones indicated that the deduced full length DMNT3B consists of 853 amino acid residues. Since in-frame stop codons are found upstream of the ATG of both DNMT3A and DNMT3B, it is concluded that these cDNA clones encode full-length DNMT3A and DNMT3B proteins.

The full length human DNMT3A and DNMT3B cDNAs encode 912 and 853 amino acid polypeptides, termed DNMT3A and DNMT3B1, respectively. Nucleotide and polypeptide sequences are presented in FIGS. 1C, 1D, 2C and 2D, respectively. The DNMT3B gene also produces through alternative splicing at least two shorter isoforms, termed DNMT3B2 and DNMT3B3, respectively. DNMT3B2 comprises amino acid residues 1 to 355 and 376 to 853 of SEQ ID NO:4; and DNMT3B 3 comprises amino acid residues 1 to 355 and 376 to 743 and 807 to 853 of SEQ ID NO:4.

Also identified through screening was a related zebrafish gene, termed Zmt-3, which from the EST database (GenBank number AF135438).

The GenBank STS database was used to map chromosome localization by using DNMT3A and DNMT3B sequences as queries. The results identified markers WI-6283 (GenBank Accession number G06200) and SHGC-15969 (GenBank Accession number G15302), which matched the cDNA sequence of DNMT3A and DNMT3B, respectively. WI-6283 has been mapped to 2p23 between D2S171 and D2S174 (48-50 cM) on the radiation hybrid map by Whitehead Institute/MIT Center for Genome Research. The corresponding mouse chromosome location is at 4.0 cM on chromosome 12. SHGC-15969 has been mapped to 20 pl 1.2 between D20S184 and D20S106 (48-50 cM) by Stanford Human Genome Center. The corresponding mouse chromosome locus is at 84.0 cM on chromosome 2.

Taking the advantage of the newly identified DNMT3A and DNMT3B cDNA sequences, the human genomic sequence database was searched by BLAST. While human DNMT3A cDNA did not match any related genomic sequences in the database, a DNMT3B genomic YAC clone from GenBank (AL035071) was identified when DNMT3B cDNA sequences were used as queries.

The DNMT3B cDNA and the genomic DNA GenBank (AL035071) clone were used to map all exons using BEST-FIT of the GCG program. As shown in FIG. 4C, there are total 23 exons, spanning some 48 kb genomic DNA. The putative first exon is located within a CpG island where the promoter is probably located as predicted by the GENSCAN program (Whitehead/MIT Center for Genome Research).

Sequencing of various cDNA clones indicates that the human DNMT3B gene contains three alternatively spliced exons, exons 10, 21 and 22. Similar to the mouse gene, DNMT3B1 contains all 23 exons, whereas DNMT3B2 lacks exon 10 and DNMT3B3 lacks exons 10, 21 and 22. The nucleotide sequences at the exon/intron boundaries are shown in FIG. 4D. The elucidation of human DNMT3B gene structure may facilitate analysis of DNMT3B mutations in certain cancers with characteristic hypomethylation of genomic: DNA (Narayan, A., et al., *Int. J. Cancer* 77:833-838 (1998); Qu, G., et al., *Mutan. Res.* 423:91-101 (1999)).

FIG. 3A presents an alignment of mouse Dnmt3a and Dnmt3b polypeptide sequences that was accomplished using the GCG program. The vertical lines indicate amino acid identity, while the dots and the colons indicate similarities. Dots in amino acid sequences indicate gaps introduced to maximize alignment. The conserved Cys-rich region is shaded. The full length mouse Dnmt3a and Dnmt3b genes encode 908 and 859 amino acid polypeptides. Furthermore, the analysis reveals that both genes contained the highly conserved cytosine methyltransferase motifs and share overall 51% of amino acid identity (76% identity in the catalytic domain). The Dnmt3b gene also produces at least two shorter isoforms of 840 and 777 amino acid residues, termed Dnmt3b2 and Dnmt3b3, respectively, through alternative splicing (FIG. 4).

FIG. 3B presents a GCG program alignment using the of the protein sequences of human DNMT3A and DNMT3B1. Vertical lines represent identical amino acid residues, whereas dots represent conserved changes. Dots in amino acid sequences indicate gaps introduced to maximize alignment.

In FIG. 4A, presents a schematic diagram of the overall protein structures for mouse Dnmt1, mouse Dnmt2, a putative methyltransferase, and the family of Dnmt3a and Dnmt3b(1-3) methyltransferases. Dnmt1, Dnmt3a and Dnmt3bs all have a putative N-terminal regulatory domain. The filled bars represent the five conserved methyltransferase motifs (1, IV, VI, IX, and X). The shaded boxes in Dnmt3a and Dnmt3bs represent the Cys-rich region that shows no sequence homology to the Cys-rich, $Zn^{2+}$-binding region of Dnmt1 polypeptide. Sites of alternative splicing at amino acid residues 362-383 and 749-813 in Dnmt3bs are indicated.

Figure 4B:
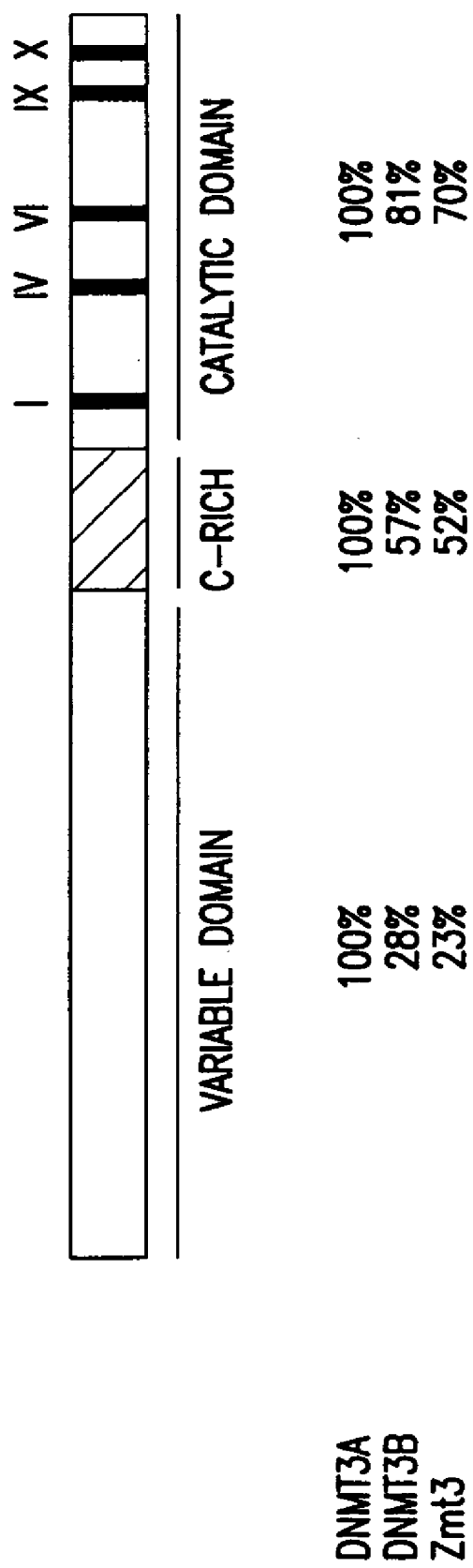
FIG. 4B presents a schematic of the DNMT3A, DNMT3B and zebrafish Zmt3 proteins.
Figure 4C:
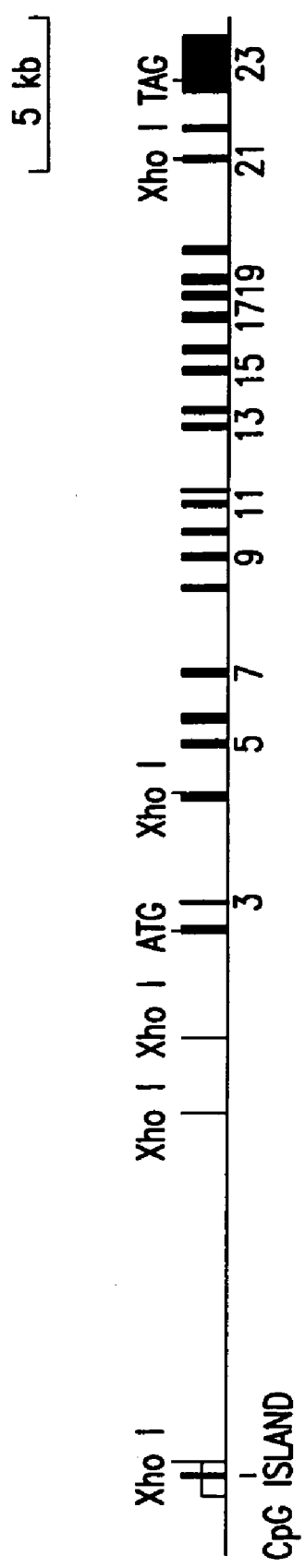

An analysis of the human DNMT3 proteins provides similar results as with the mouse Dnmt proteins. FIG. 4B presents a similar schematic of the human DNMT3 proteins and zebrafish Znmt3 protein. The homology between differences between these DNMT3 proteins is indicated by the percentage of sequence identity when compared to DNMT3A.

In addition, the genomic organization of the human DNMT3B1 locus is presented in FIG. 4C as possessing 23 exons (filled rectangles), a CpG island (dotted rectangle), a translation initiation codon (ATG) and a stop codon (TAG) in exons 2 and 23, respectively. FIG. 4D presents the size of the exons and introns as well as sequences (uppercase for exons and lowercase for introns) at exon/intron boundaries.

In FIG. 5, sequence analysis of the catalytic domain indicates that this new family of DNA methyltransferases contains conserved amino acid residues in each of the five highly conserved motifs, but significant differences are discernible when compared to the known consensus sequences.

FIG. 5A presents an alignment by ClustalW 1.7 of the amino acid sequences of the five highly conserved motifs in eukaryotic methyltransferase genes. Amino acid residues which are conserved in five or more genes are highlighted. The Dnmt3 family methyltransferases are most closely related to a bacterial DNA methyltransferase (M. Spr.). Sequence comparison of the catalytic domain of all known eukaryotic DNA methyltransferases and most of the bacterial cytosine methyltransferases used in the tblastn search indicates that this family of methyltransferases are distantly related to all the known eukaryotic DNA methyltransferases, including the Dnmt 1 polypeptide from vertebrate and plant (Bestor, T. H. et al, *J. Mol. Biol.* 203:971-983 (1988), Yen, R-W. C. et al., *Nucleic Acids Res.* 20:2287-2291 (1992) and Finnegan, E. J. and Dennis, E. S. *Nucleic Acids Res.* 21:2383-2388 (1993)); the human and mouse Dnmt 2 polypeptides (Yoder. J. A. and Bestor, T. H. *Hum. Mol. Genet.* 7:279-284 (1998), Okano, M., Xie, S. & Li, E., (submitted)); and masc1 from Ascobolus (Malagnac, F. et al., *Cell* 91:281-290 (1997)), indicating that the Dnmt3 gene family originated from a unique prokaryotic prototype DNA methyltransferase during evolution.

The cysteine-rich region located upstream of the catalytic domain was found to be conserved among all of the DNMT3 proteins (FIG. 5B). This Cysteine-rich region, however, is unrelated to the Cysteine-rich (or $Zn^{2+}$-binding) region of DNMT1 (Bestor, T. H. et al., *J. Mo. Biol.* 203:971-983 (1998); Bestor, T. H., *EMBO J.* 11:2611-2617 (1992)). Interestingly, the Cysteine-rich domain of DNMT3 proteins shares homology with a similar domain found in the X-linked ATRX gene of the SNF2/SW1 family (Picketts, D. J., et al., *Hum. Mol. Genet.* 5:1899-1907 (1996)), raising the interesting possibility that this domain may mediate protein-protein or protein-DNA interactions.

Figure 5C:
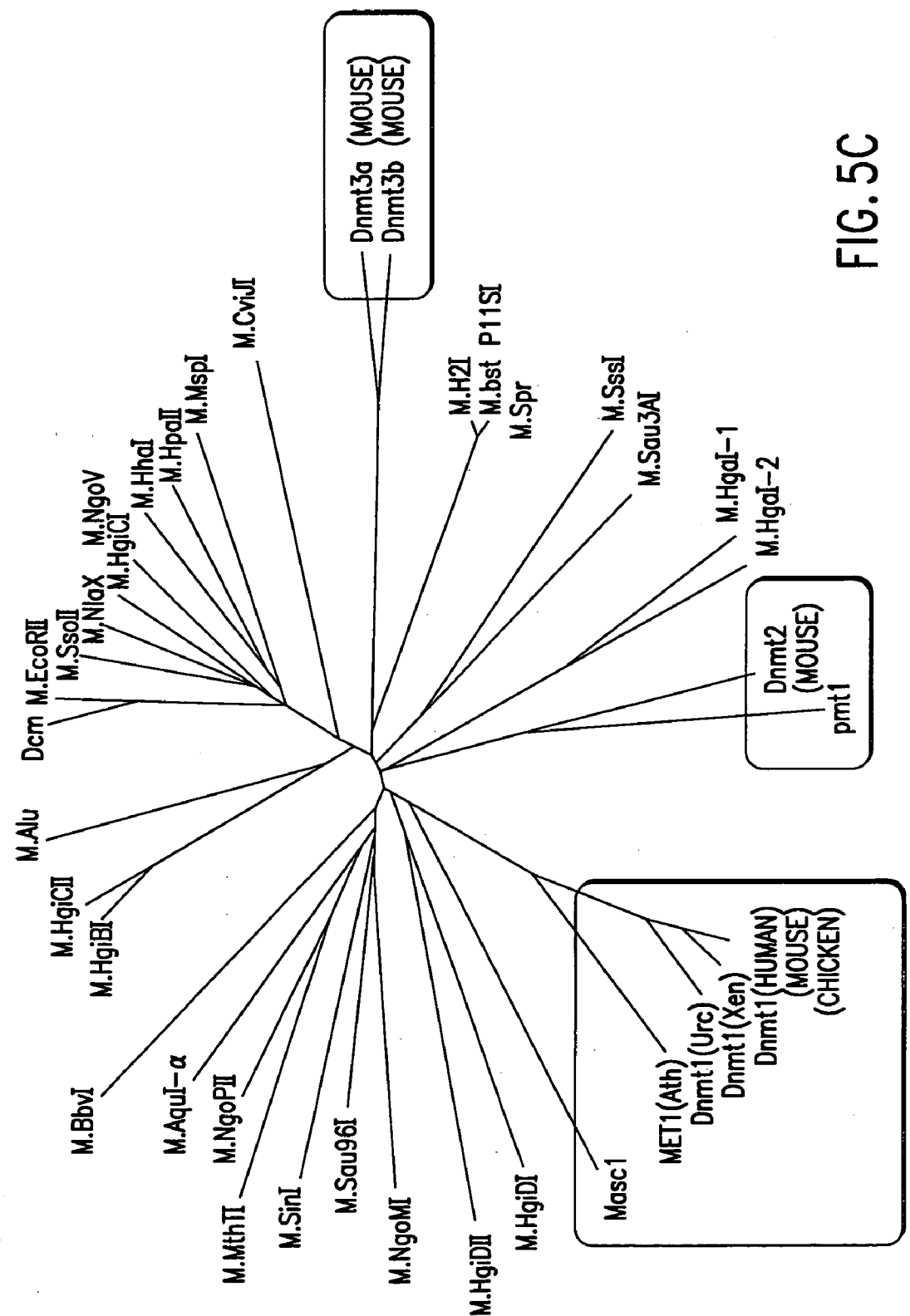
FIG. 5C presents a non-rooted phylogenic tree of methyltransferase proteins.

The evolutionary relatedness of cytosine-5 methyltransferases as shown by a non-rooted phylogenic tree is presented in FIG. 5C. Amino acid sequences from motifI to motifVI of bacterial and eukaryotic cytosine-5 methyltransferases were used for sequence alignment, and the alignment data was analyzed by ClustalW 1.7 under conditions excluding positions with gaps. Results were visualized utilizing Phlip version 3.3. Amino acid sequences from motif IX to motif X were also analyzed and provided similar results (data not shown). (Abbreviation Ath; *Arabidopsis thaliana*, Urc; sea urchin. Xen; *Xenopus laevis*).

Example 2

Baculovirus-Mediated Expression of Dnmt3a and Dnmt3b

To test whether the newly cloned Dnmt3 genes encode active DNA methyltransferases, the cDNAs of Dnmt3a, Dnmt3b1, Dnmt3b2, and Dnmt1 were overexpressed in insect cells using the baculovirus-mediated expression system (Clontech, Calif.).

To construct the Dnmt3a expression vector, pSX134, the Xma I/Eco RI fragment of Dnmt3a cDNA was first cloned into the Nco I/Eco RI sites of pET2 Id with the addition of an Xma I/Nco I adapter (SX165: 5'-CATGGGCAGCAGC-CATCATCATCATCATCATGGGAATTCCATGCCC TCCAGCGGCC and SX166: 5'-CCGGGGCCGCTG-GAGGGCATGGA ATTCCCATGATGATGATGATG-GCTGCTGCC) that produced pSX132His. pSX134 was obtained by cloning the EcoR I/Xba I fragment of pSX 132His into the EcoR I/Xba I sites of pBacPAK9. The Dnmt3b1 and Dnmt3b2 expression vectors, pSX153 and pSX154, were constructed by cloning Eco RI fragments of Dnmt3b1 and Dnmt3b2 cDNA into the Eco RI site of pBacPAK9, respectively. The Dnmt1 expression vector pSX148 was constructed by cloning the Bgl I/Sac I fragment of Dnmt1 cDNA into the Bgl II/Sac I sites of pBacPAK-His2 with the addition of a Bgl 1/Bgl II adapter (SX180: 5'-GATCTATGCCAGCGCGAACAGCTCCAGC-CCGAGTGCCTGCGCTTGC CTCCC and SX181: 5'-AG-GCAAGCGCAGGCACTCGGGCTGGAGCTGTT CGCGCTGGCATA).

pSX134 (Dnmt3a), pSX153 (Dnmt3b1), pSX153 (Dnmt3b2) and pSX148 (Dnmt1) were used to make the recombinant baculoviruses according to the procedures recommended by the manufacturer. T175 flasks were used for cell culture and virus infection. Sf621 host cells were grown in the SF-900 II SFM medium with 10% of the certified FBS (both from GIBCO, MD) and infected with the recombinant viruses 12-24 hours after the cells were split when they reached 90-95% affluence. After 3 days, the infected insect cells were harvested and frozen in the liquid nitrogen for future use.

Example 3

RNA Expression Analysis

ES cells were routinely cultured on a feeder layer of mouse embryonic fibroblasts in DMEM medium containing LIF (500 units/ml) and were differentiated as embryoid bodies in suspension culture as described (Lei, H., et al., *Development* 122:3195-3205 (1996)). Ten days after seeding, embryoid bodies were harvested for RNA preparation.

Total RNA was prepared from ES cells, ovary and testis tissue using the GTC-CsCl centrifugation method, fractionated on a formaldehyde denaturing 1% agarose gel by electrophoresis and transferred to a nylon membrane. PolyA+ RNA blots (2 µg per lane) of mouse and human tissues were obtained from Clontech, Calif. All blots were hybridized to random-primed cDNA probes in hybridization solution containing 50% formamide at 42° C. and washed with 0.2×SSC, 0.1% SDS at 65° C. and exposed to X-ray film (Kodak).

Figure 6A:
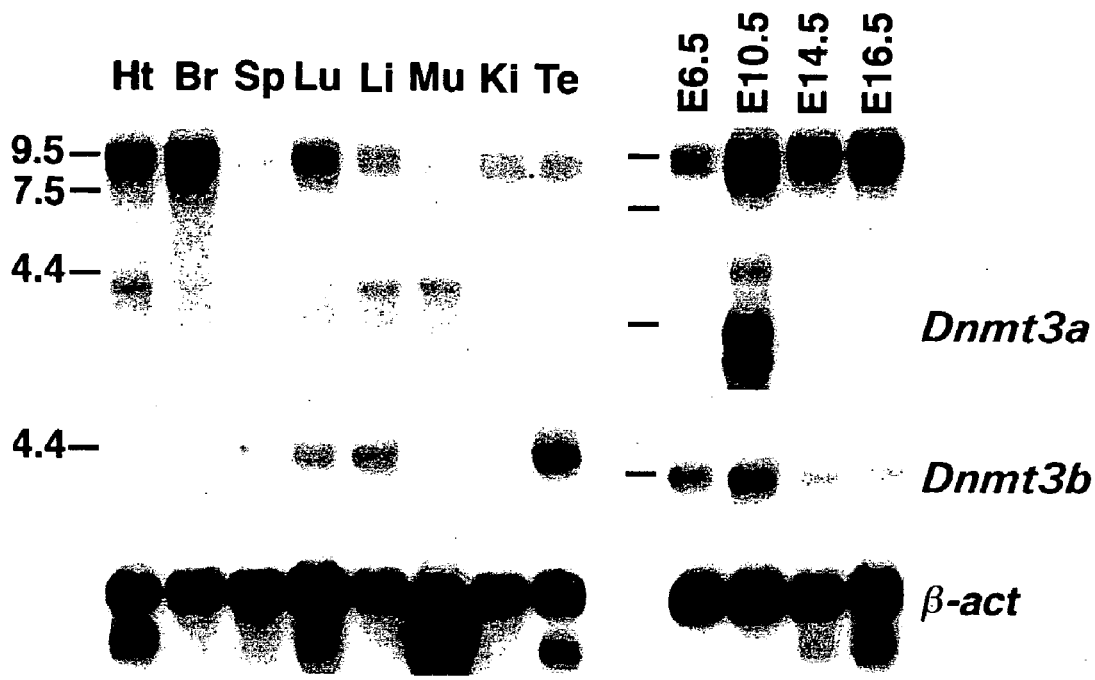
FIG. 6A-6C demonstrates the expression of Dnmt3a and Dnmt3b in mouse adult tissues, embryos, and ES cells by northern blot.
Figures 6B, 6C:
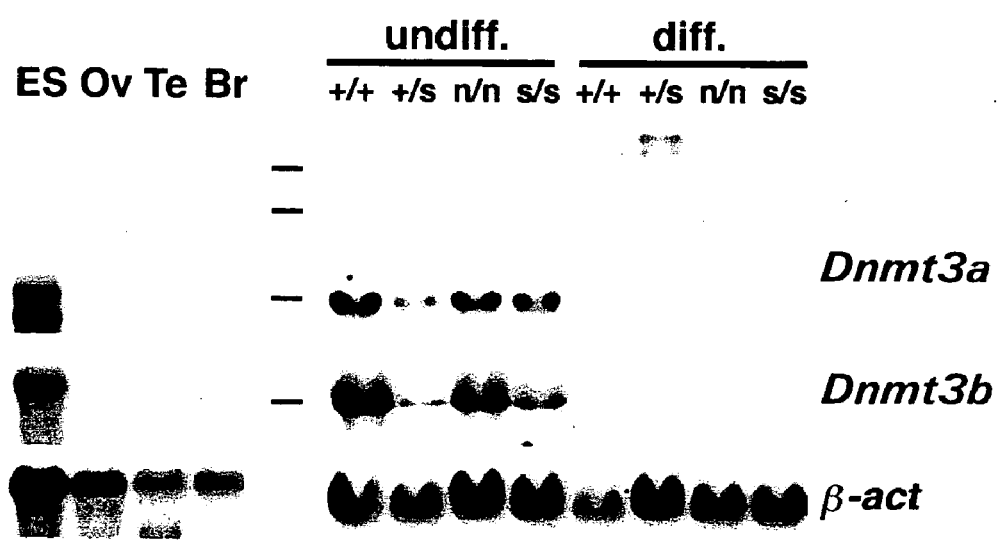

FIG. 6A presents mouse polyA+ RNA blots of adult tissues (left) and embryos (right) probed with full length Dnmt3a, Dnmt3b and a control β-actin cDNA probe. Each lane contains 2 µg of polyA+RNA. (Ht. Heart; Br. Brain; Sp, Spleen; Lu, Lung; Li, Liver; Mu, Skeletal Muscle; Ki. Kidney; Te, Testis; and embryos at gestation days 7 (E7), 11 (E11), 15 (E15), and 17 (E17). FIG. 6B is a mouse total RNA blot (10 µg per lane) of ES cell and adult organ RNA samples and FIG. 6C shows a mouse total RNA blot (20 µg per lane) of undifferentiated (Undiff.) and differentiated (Diff.) ES cells RNA hybridized to Dnmt3a, Dnmt3b or β-actin probes.

It has been shown that the maintenance methylation activity is constitutively present in proliferating cells, whereas the de novo methylation activity is highly regulated. Active de novo methylation has been shown to occur primarily in ES cells (or embryonic carcinoma cells), early postimplantation embryos and primordial germ cells (Jähaner, D. and Jaenish, R., "DNA Methylation in Early Mammalian Development," In *DNA Methylation: Biochemistry and Biological Significance*, Razin, A. et al., eds., Springer-Verlag (1984) pp. 189-219; Razin, A., and Cedar, H., "DNA Methylation and Embryogenesis," in *DNA Methylation: Molecular Biology and Biological Significance*, Jost., J. P. et al, eds. Birkhäuser Verlag, Basel, Switzerland (1993) pp. 343-357; Chaillet, J. R. et al, *Cell* 66:77-83 (1991); and Li, E. "Role of DNA Methylation in Development," in *Genomic Imprinting: Frontiers in Molecular Biology*, Reik, W. and Sorani, A. eds., IRL Press, Oxford (1997) pp. 1-20). The expression of both Dnmt3a and Dnmt3b in mouse embryos, adult tissues and ES cells was examined. The results indicate that two Dnmt3a transcripts, 9.5 kb and 4.2 kb, are present in embryonic and adult tissue RNA. The 4.2 kb transcript, corresponding to the size of the full length cDNA, was expressed at very low levels in most tissues, except for the E11.5 embryo sample (FIG. 6A). A single 4.4 kb Dnmt3b transcript is detected in embryo and adult organ RNAs, with relatively high levels in testes and E11.5 embryo samples (FIG. 6A). Interestingly, both genes are expressed at much higher levels in ES cells than in adult tissues (FIG. 6B), and their expression decreased dramatically upon differentiation of ES cells in culture (FIG. 6C). In addition, Dnmt3a and Dnmt3b expression levels are unaltered in Dnmt1-deficient ES cells (FIG. 6C), suggesting that regulation of Dnmt3a and Dnmt3b expression is independent of Dnmt1.

These results suggest that both Dnmt3a and Dnmt3b are expressed specifically in ES cells and E11.5 embryo and/or testes. The expression in the E11.5 embryo and testes may correlate with the presence of developing or mature germ cells in these tissues. Therefore, the expression pattern of Dnmt3a and Dnmt3b appears to correlate well with de novo methylation activities in development.

Figure 9:
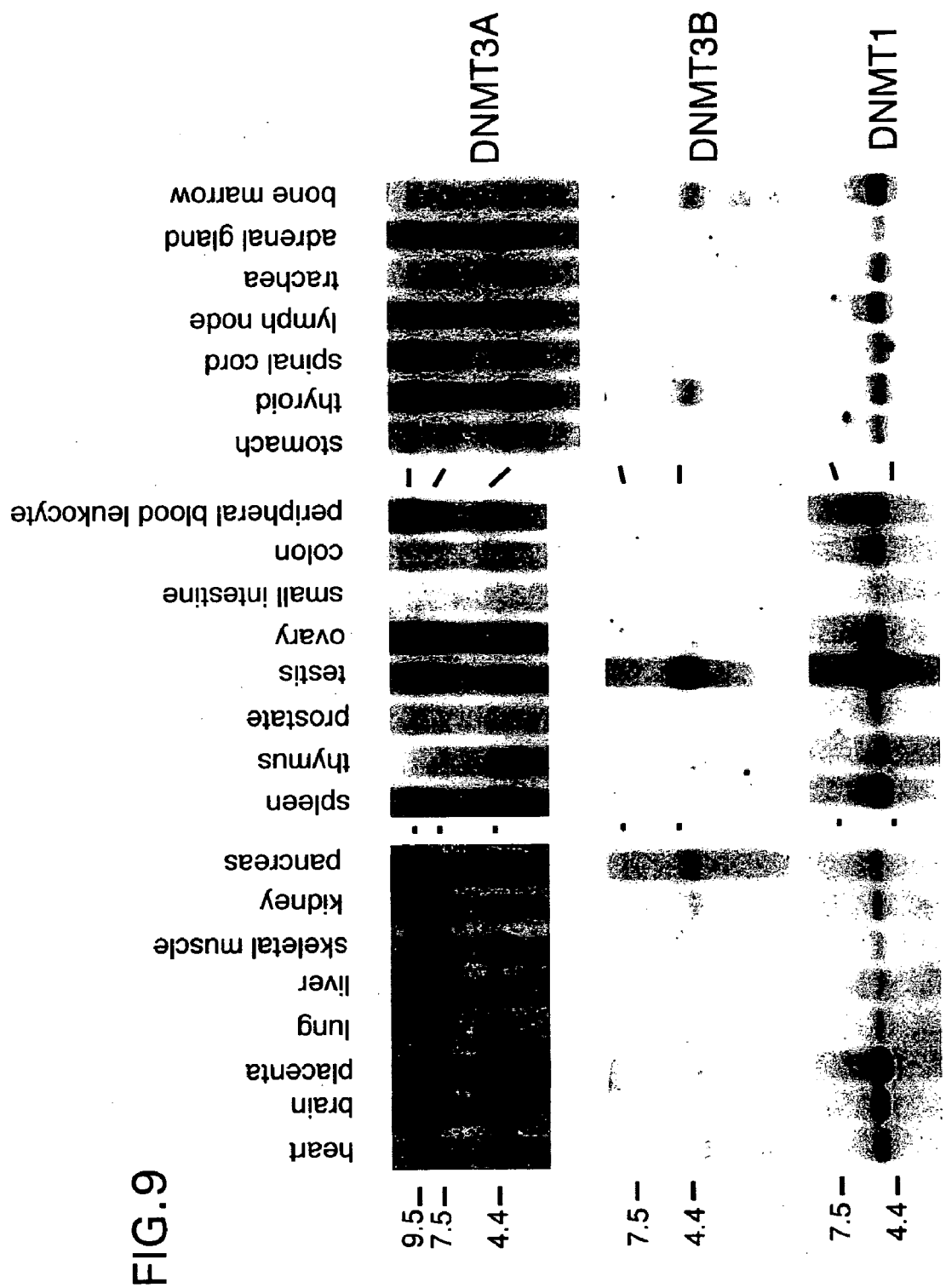
FIG. 9 presents Northern blot expression analysis of DNMT3A and DNMT3B.

For the RNA expression analysis of human DNMT3 genes, polyA+ RNA blots were hybridized using DNMT3A and DNMT3B cDNA fragments as probes. Results indicate that DNMT3A RNA was expressed ubiquitously and was readily detected in most tissues examined at levels slightly lower than DNMT1 RNA (Fig.X). Three major DNMT3A transcripts, approximately 4.0, 4.4, and 9.5 kb, were detected. The relative expression level of the transcripts appeared to vary from tissue to tissue. Transcripts of similar sizes were also detected in mouse tissues. Results utilizing DNMT3B cDNA probes indicate that transcripts of about 4.2 kb were expressed at much lower levels in most tissues, but could be readily detected in the testis, thyroid and bone marrow (FIG. 9). Sequence analyses of different cDNA clones indicate the presence of alternatively spliced transcripts, although the size differences between these transcripts are too small to be detected by Northern analysis.

Figure 10:
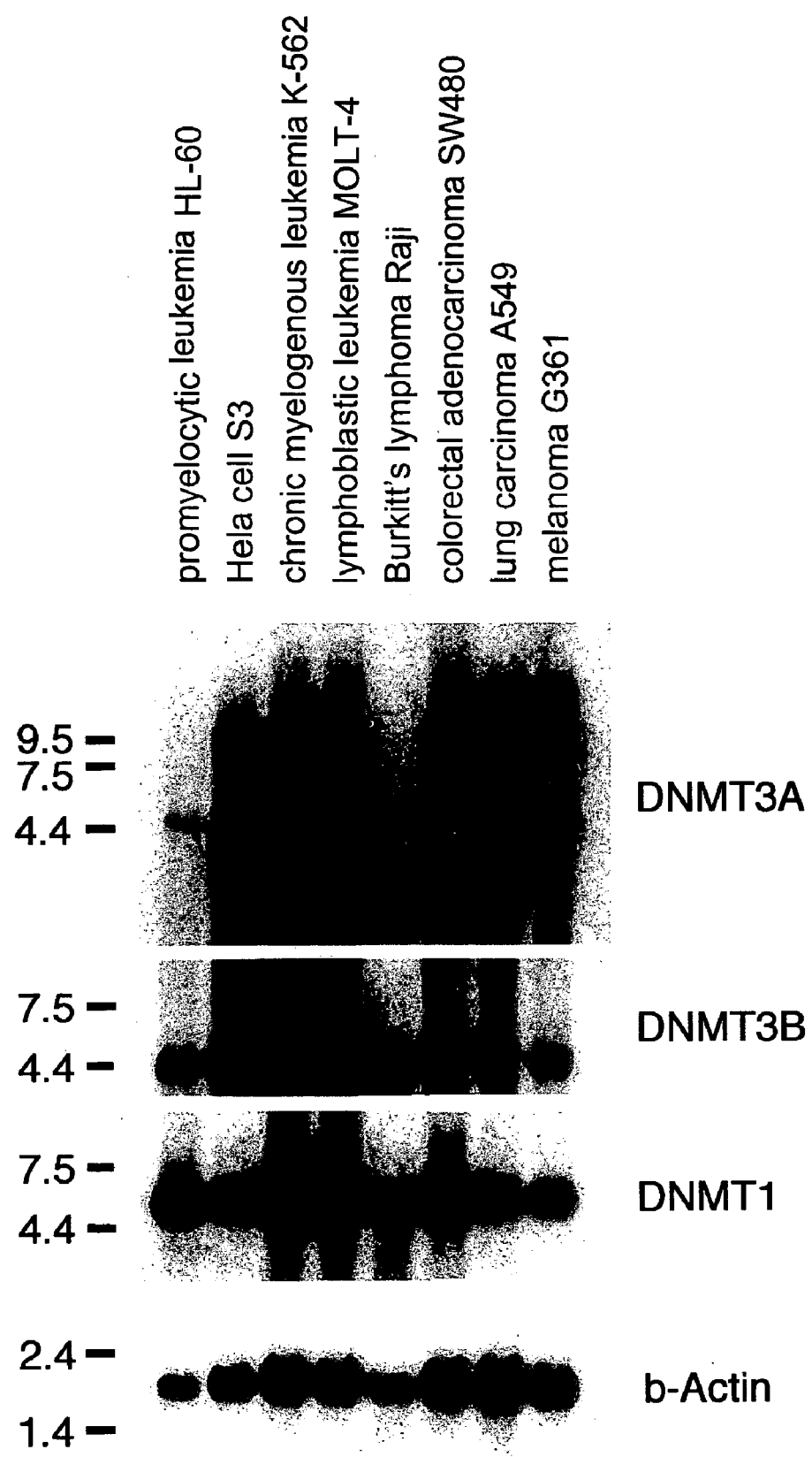
FIG. 10 presents DNMT3 Northern Blot expression analysis of DNMT3A and DNMT3B in human tumor cell lines.

Hypermethylation of tumor suppressor genes is a common epigenetic lesion found in tumor cells (Laird, P. W. & Jaenisch, R., Ann. Rev. Genet. 30:441-464 (1996); Baylin, S. B., Adv. Cancer Res. 72:141-196 (1998)). To investigate whether DNMT3A and DNMT38 am abnormally activated in tumor cells, DNMT3 RNA expression was analyzed in several tumor cell lines by Northern blot hybridization. Results demonstrated that DNMT3A was expressed at higher levels in most tumor cell lines examined. (FIG. 10). As in the normal tissues, three different size transcripts were also detected in tumor cells. The ratio of these transcripts appeared to be variable in different tumor cell lines. DNMT3B expression was dramatically elevated in most tumor cell lines examined though it was expressed at very low levels in normal adult tissues (FIG. 10). The expression levels of both DNMT3A and DNMT3B appear to be comparable and proportional to that of DNMT1.

The murine Dnmt3a and Dnmt3b genes are highly expressed in undifferentiated ES cells, consistent with their potential role in de novo methylation during early embryonic development. Additionally, both genes are highly expressed in early embryos. Differences in their expression patterns in adult tissues in both human and mice suggest that each gene may have a distinct function in somatic tissues and may methylate different genes or genomic sequences. The elevated expression of DNMT3 genes in human tumor cell lines suggests that the DNMT3 enzyme may be responsible for de novo methylation of CpG islands in tumor suppressor genes during tumor formation.

Example 4

Methyltransferase Activity Assay

In order to demonstrate DNA cytosine methyltransferase activity, the polypeptides of the invention were expressed and purified from recombinant host cells for use in in vitro assays.

Infected insect Sf21 cells and NIH3T3 cells were homogenized by ultrasonication in lysis solution (20 mM Tris-HCl, pH7.4, 10 mM EDTA, 500 mM NaCl, 10% glycerol, 1 mM DTT, 1 mM PMSF, 1 ug/ml leupeptin, 10 ug/ml TPCK, 10 ug/ml TLCK) and cleared by centrifugation at 100,000 g for 20 min.

The methyltransferase enzyme assay was carried out as described previously (Lei, H. et al., *Development* 122:3195-3205 (1996)). DNA substrates used in the assays include: poly (dI-dC), poly (dG-dC) (Pharmacia Biotech), lambda phage DNA (Sigma), pBluescriptIISK (Stratagene, Calif.), pMu3 plasmid, which contains tandem repeats of 535 bp RsaI-RsaI fragment of MMLV LTR region in pUC9, and oligonucleotides. The oligonucleotide sequences utilized include:

```
#1,   5'-AGACMGGTGCCAGMGCAGCTGAGCMGGATC-3',

#2,   5'-GATCMGGCTCAGCTGMGCTGGCACMGGTCT-3',

#3,   5'-AGACCGGTGCCAGCGCAGCTGAGCCGGATC-3',
and

#4,   5'-GATCCGGCTCAGCTGCGCTGGCACCGGTCT-3'.

(M represents 5-methylcytosine)
```

These sequences are the same as described in a previous study (Pradhan, S. et al., *Nucleic Acids Res.* 25:4666-4673 (1997)). Oligonucleotides were synthesized and purified by polyacrylamide gel electrophoresis (PAGE). To make double strand oligonucleotides, equimolar amounts of the two complimentary oligonucleotides were heated at 94° C. for 10 min., mixed, incubated at 78° C. for 1 hr and cooled down slowly at room temperature. The annealing products were quantified for the yield of double-stranded oligonucleotides (dsDNA) by PAGE and methylene blue staining. In all cases, the yield of dsDNA was higher than 95%. The dsDNA of #1 and #2 were used as 'fully' methylated substrates, dsDNA of #1 and #4 as the hemi-methylated substrates, and dsDNA of #3 and #4 as unmethylated substrates.

For Southern analysis of the methylation of retrovirus DNA, 2 ug of pMMLV8.3, an 8.3 kb Hind III fragment of Moloney murine leukemia virus cDNA in pBluescriptIISK, was methylated in vitro for 15 hrs under the same reaction conditions described above except that 160 uM of cold SAM was used instead of $^3$H-methyl SAM. Then, an equal volume of the solution containing 1% SDS, 400 mM NaCl, and 0.2 mg/ml Proteinase K was added, and the sample was incubated at 37° C. for 1 hr. After phenol/chloroform extraction, DNA was precipitated with ethanol, dried and dissolved in TE buffer. This procedure was repeated 5 times. An aliquot of DNA was purified after the first, third and fifth reaction, digested with Hpa II or Msp I in combination with Kpn I for 16 hrs, separated on 1% agarose gels, blotted and hybridized to the pMu3 probe.

Figure 7D:

In a standard methyltransferase assay, enzyme activity was detected with protein extracts from Sf21 cells overexpressing Dnmt3a and Dnmt3b polypeptides. Similar to the results obtained with the Dnmt1 polypeptide, the overexpressed Dnmt3 proteins were able to methylate various native and synthetic DNA substrates, among which poly(dI-dC) consistently gave rise to the highest initial velocity (FIG. 7a). An analysis of the methylation of Hpa II sites in retroviral DNA by these enzymes was also performed. An MMLV full length cDNA was methylated for 1-5 times by incubation with protein extract from control Sf21 cells or Sf21 cells infected with baculoviruses expressing Dnmt1, Dnmt3a or Dnmt3b polypeptides. The Hpa II/Msp I target sequence, CCGG, is resistant to the Hpa 11 restriction enzyme, but sensitive to Msp I digestion when the internal C is methylated, and the restriction site becomes resistant to Msp I digestion when the external C is methylated (Jentsch, S. et al. *Nucleic Acids Res.* 9:2753-2759 (1981)). Both Dnmt3a and Dnmt3b polypeptides could methylate multiple Hpa II sites in the 3' LTR regions of the MMLV DNA, as indicated by the presence of Hpa II-resistant fragments, though less efficiently than Dnmt1 polypeptide (FIG. 7b). Significantly, even after five consecutive rounds of in vitro methylation, the viral DNA was completely digested by Msp I. This result indicates that both Dnmt3a and Dnmt3b polypeptides methylate predominantly the internal cytosine residues, therefore, CpGs. Previously it was shown that the same region of the proviral DNA was efficiently methylated in Dnmt1 null ES cells infected by the MMLV virus (Lei. H. et al., *Development* 122:3195-3205 (1996)).

FIG. 7A shows $^3$H-methyl incorporation into different DNA substrates (poly (dI-dC), poly (dG-dC) (squares), lambda phage DNA (circles), pBluescriptIISK (triangles), and pMu3 (diamonds)) when incubated with protein extracts of Sf21 cells expressing Dnmt1, Dnmt3a, or Dnmt3b1. FIG. 7B shows Southern blot analysis of the in vitro methylation of untreated pMMLV DNA (lanes 1-3) and pMMLV DNA incubated with MT1 (lane 4-10), MT3α (lanes 11-15), MT3β (lanes 16-20) or control Sf21 (lanes 21-25) extracts that were digested with Kpn I(K), Kpn I and Msp I (K/M) or Kpn I and Hpa II (K/H). Restriction enzyme digested samples were then subjected to Southern blot analysis using the pMu3 probe.

Figure 8E:
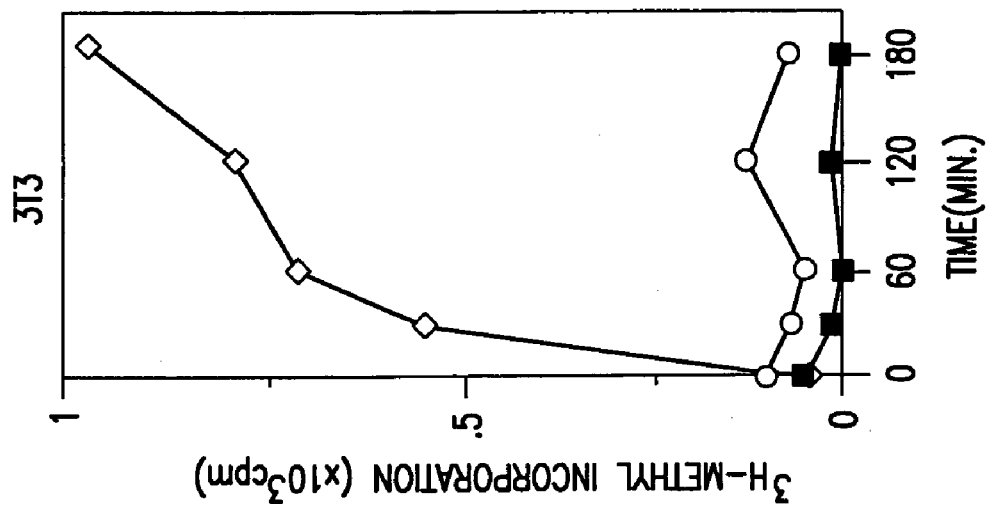
Figure 8D:
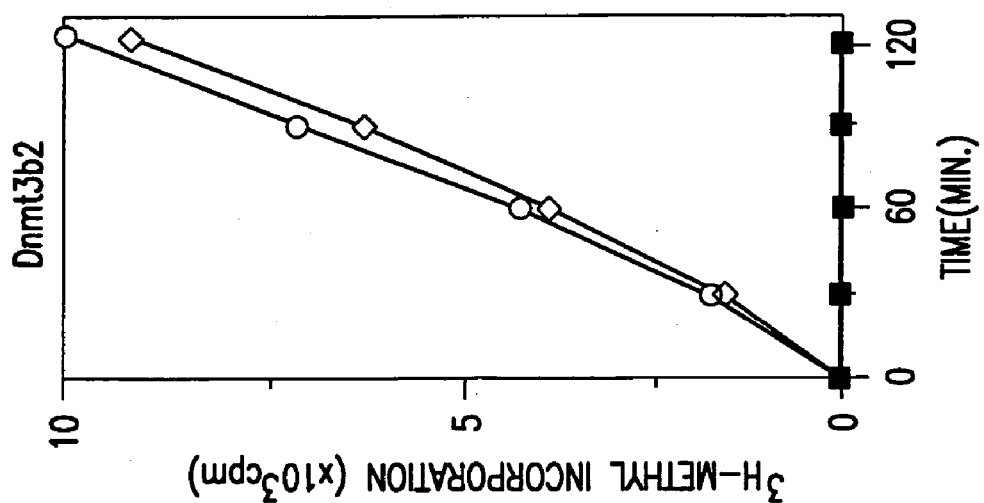

Dnmt1 protein appears to function primarily as a maintenance methyltransferase because of its strong preference for hemimethylated DNA and direct association with newly replicated DNA (Leonhardt, H. et al., *Cell* 71:865-873 (1992)). To determine whether Dnmt3a and Dnmt3b polypeptides show any preference for hemimethylated DNA over unmethylated DNA, a comparison was done to examine the methylation rate of unmethylated versus hemimethylated oligonucleotides. Gel-purified double stranded oligonucleotides were incubated with protein extracts of Sf21 cells expressing Dnmt1, Dnmt3a, Dnmt3b1, Dnmt3b2 or NIH3T3 cell extract (unmethylated substrates (open circles), hemi-methylated substrates (half black diamonds) or completely methylated substrates (closed squares)). While baculovirus-expressed Dnmt1 polypeptide or 3T3 cell extract showed much higher activities when hemimethylated DNA was used as a substrate, Dnmt3a, Dnmt3b 1 and Dnmt3b2 polypeptides showed no detectable preference for hemimethylated DNA (FIG. 8).

What is claimed is:

1. An isolated nucleic acid molecule comprising a polynucleotide selected from the group consisting of:
   a. a polynucleotide sequence encoding a polypeptide comprising amino acids from about 1 to about 908 in SEQ ID NO:5;
   b. a polynucleotide sequence encoding a polypeptide comprising amino acids from about 1 to about 859 in SEQ ID NO:6;
   c. a polynucleotide sequence encoding a polypeptide comprising amino acids from about 1 to about 912 in SEQ ID NO:7;
   d. a polynucleotide sequence encoding a polypeptide comprising amino acids from about 1 to about 853 in SEQ ID NO:8;
   e. a polynucleotide sequence that is at least 90% identical to the polynucleotide sequence of (a), (b), (c) or (d) encoding a polypeptide; and
   f. a polynucleotide sequence fully complementary to the polynucleotide sequence of (a), (b), (c), (d) or (e) encoding a polypeptide,
wherein said polypeptide methylates DNA in an in vitro, assay.

2. A method of making a recombinant vector comprising inserting an isolated nucleic acid molecule of claim 1 into a vector selected from a group consisting of:
   a. a DNA vector; and
   b. an RNA vector.

3. A recombinant vector comprising the isolated nucleic acid molecule of claim 1.

4. A method of making an isolated recombinant host cell comprising introducing the recombinant vector of claim 3 into a host cell.

5. An isolated recombinant host cell comprising the vector of claim 3.

6. A method for producing a de novo DNA cytosine methyltransferase polypeptide, comprising culturing the recombinant host cell of claim 5 under conditions such that said polypeptide is expressed and recovering said polypeptide.

7. An isolated oligonucleotide probe or primer selected from the group consisting of:
   a. at least 50 contiguous nucleotides of SEQ ID NO:1, provided that said nucleotides are not AA052791(SEQ ID NO: 9); AA111043(SEQ ID NO:10); AA154890 (SEQ ID NO:11); AA240794(SEQ ID NO:12); AA756653(SEQ ID NO:13); W58898(SEQ ID NO:14); W59299(SEQ ID NO:15); W91664(SEQ ID NO:16); W91665(SEQ ID NO:17); and
   b. a nucleotide sequence fully complementary to the nucleotide sequence in (a).

8. An isolated oligonucleotide probe or primer selected from the group consisting of:
   a. at least 30 contigudus nucleotides of SEQ ID NO:2, provided that said nucleotides are not AA116694 (SEQ ID NO:18); AA119979 (SEQ ID NO:19); AA177277 (SEQ ID NO:20); AA210568 (SEQ ID NO:21); AA399749 (SEQ ID NO:22); AA407106 (SEQ ID NO:23); AA575617 (SEQ ID NO:24); and
   b. a nucleotide sequence fully complementary to the nucleotide sequence in (a).

9. A method for in vitro de novo methylation of DNA, comprising:
   a. contacting said DNA with a de novo DNA cytosine methyltransferase polypeptide encoded by the nucleic acid molecule of any of parts (a)-(e) of claim 1;
   b. providing an appropriately buffered solution with substrate and cofactor; and
   c. purifying said DNA.

10. The nucleic acid molecule of claim 1, wherein said polynucleotide is that of part (a).

11. The nucleic acid molecule of claim 1, wherein said polynucleotide is that of part (b).

12. The nucleic acid molecule of claim 1, wherein said polynucleotide is that of part (c).

13. The nucleic acid molecule of claim 1, wherein said polynucleotide is that of part (d).

14. The nucleic acid molecule of claim 1, wherein said polynucleotide is that of part (e).

15. The nucleic acid molecule of claim 1, wherein said polynucleotide is that of part (f).

16. An isolated nucleic acid molecule comprising a polynucleotide selected from the group consisting of:
   a. a polynucleotide sequence encoding mouse Dnmt3a polypeptide contained in ATCC Deposit No. 209933;
   b. a polynucleotide sequence encoding mouse Dnmt3b polypeptide contained in ATCC Deposit No. 209934;
   c. a polynucleotide sequence encoding human DNMT3A polypeptide contained in ATCC Deposit No. 98809;
   d. a polynucleotide sequence encoding human DNMT3B polypeptide contained in ATCC Deposit No. 326637;
   e. a polynucleotide sequence at least 90% identical to the polynucleotide sequence of (a), (b), (c) or (d) encoding a polypeptide; and
   f. a polynucleotide sequence fully complementary to the polynucleotide sequence of (a), (b), (c), (d) or (e) encoding a polypeptide,
wherein said polypeptide methylates DNA in an in vitro assay.

17. The nucleic acid molecule of claim 16, wherein said polynucleotide is that of part (a).

18. The nucleic acid molecule of claim 16, wherein said polynucleotide is that of part (b).

19. The nucleic acid molecule of claim 16, wherein said polynucleotide is that of part (c).

20. The nucleic acid molecule of claim 16, wherein said polynucleotide is that of part (d).

21. The nucleic acid molecule of claim 16, wherein said polynucleotide is that of part (e).

22. The nucleic acid molecule of claim 16, wherein said polynucleotide is that of part (f).

23. An isolated nucleic acid molecule comprising a polynucleotide at least 95% identical to a polynucleotide selected from the group consisting of:

a. a polynucleotide sequence encoding a polypeptide comprising amino acids from about 1 to about 908 in SEQ ID NO:5;
b. a polynucleotide sequence encoding a polypeptide comprising amino acids from about 1 to about 859 in SEQ ID NO:6;
c. a polynucleotide sequence encoding a polypeptide comprising amino acids from about 1 to about 912 in SEQ ID NO:7;
d. a polynucleotide sequence encoding a polypeptide comprising amino acids from about 1 to about 853 in SEQ ID NO:8; and
e. a polynucleotide sequence fully complementary to the polynucleotide sequence of (a), (b), (c) or (d) encoding a polypeptide, wherein said polypeptide methylates DNA in an in vitro assay.

24. The nucleic acid molecule of claim 23, wherein said polynucleotide is that of part (a).

25. The nucleic acid molecule of claim 23, wherein said polynucleotide is that of part (b).

26. The nucleic acid molecule of claim 23, wherein said polynucleotide is that of part (c).

27. The nucleic acid molecule of claim 23, wherein said polynucleotide is that of part (d).

28. The nucleic acid molecule of claim 23, wherein said polynucleotide is that of part (e).

29. An isolated nucleic acid molecule comprising a polynucleotide selected from the group consisting of:
a. SEQ ID NO:1;
b. SEQ ID NO:2;
c. SEQ ID NO:3;
d. SEQ ID NO:4;
e. a polynucleotide sequence that is at least 90% identical to the polynucleotide sequence of (a), (b), (c) or (d); and
f. a polynucleotide sequence fully complementary to the polynucleotide sequence of (a), (b), (c), (d) or (e), wherein said polynucleotide of parts (a)-(e) encodes a polypeptide that methylates DNA in an in vitro assay.

30. The nucleic acid molecule of claim 29, wherein said polynucleotide is that of part (a).

31. The nucleic acid molecule of claim 29, wherein said polynucleotide is that of part (b).

32. The nucleic acid molecule of claim 29, wherein said polynucleotide is that of part (c).

33. The nucleic acid molecule of claim 29, wherein said polynucleotide is that of part (d).

34. The nucleic acid molecule of claim 29, wherein said polynucleotide is that of part (e).

35. The nucleic acid molecule of claim 29, wherein said polynucleotide is that of part (f).

* * * * *

SEQUENCE LISTING

<160> NUMBER OF SEQ ID NOS: 82

<210> SEQ ID NO 1
<211> LENGTH: 4192
<212> TYPE: DNA
<213> ORGANISM: Mus musculus
<220> FEATURE:
<221> NAME/KEY: Unsure
<222> LOCATION: (4161)..(4161)
<223> OTHER INFORMATION: May be any nucleic acid

<400> SEQUENCE: 1

```
gaattccggc ctgctgccgg gccgcccgac ccgccgggcc acacggcaga gccgcctgaa      60
gcccagcgct gaggctgcac ttttccgagg gcttgacatc agggtctatg tttaagtctt     120
agctcttgct tacaaagacc acggcaattc cttctctgaa gccctcgcag ccccacagcg     180
ccctcgcagc cccagcctgc cgcctactgc ccagcaatgc cctccagcgg ccccggggac     240
accagcagct cctctctgga gcgggaggat gatcgaaagg aaggagagga acaggaggag     300
aaccgtggca aggaagagcg ccaggagccc agcgccacgg cccggaaggt ggggaggcct     360
ggccggaagc gcaagcaccc accggtggaa agcagtgaca cccccaagga cccagcagtg     420
accaccaagt ctcagcccat ggcccaggac tctggcccct cagatctgct acccaatgga     480
gacttggaga gcggagtga accccaacct gaggagggga gcccagctgc agggcagaag     540
ggtgggggcc cagctgaagg agagggaact gagacccccac cagaagcctc cagagctgtg     600
gagaatggct gctgtgtgac caaggaaggc cgtggagcct ctgcaggaga gggcaaagaa     660
cagaagcaga ccaacatcga atccatgaaa atggagggct cccggggccg actgcgaggt     720
ggcttgggct gggagtccag cctccgtcag cgacccatgc caagactcac cttccaggca     780
ggggaccccc actacatcag caaacggaaa cgggatgagt ggctggcacg ttggaaaagg     840
gaggctgaga agaaagccaa ggtaattgca gtaatgaatg ctgtggaaga gaaccaggcc     900
tctggagagt ctcagaaggt ggaggaggcc agccctcctg ctgtgcagca gcccacggac     960
cctgcttctc cgactgtggc caccacccct gagccagtag gaggggatgc tggggacaag    1020
aatgctacca aagcagccga cgatgagcct gagtatgagg atggccgggg ctttggcatt    1080
ggagagctgg tgtgggggaa acttcggggc ttctcctggt ggccaggccg aattgtgtct    1140
tggtggatga caggccggag ccgagcagct gaaggcactc gctgggtcat gtggttcgga    1200
gatggcaagt tctcagtggt gtgtgtggag aagctcatgc cgctgagctc cttctgcagt    1260
gcattccacc aggccaccta caacaagcag cccatgtacc gcaaagccat ctacgaagtc    1320
ctccaggtgg ccagcagccg tgccgggaag ctgtttccag cttgccatga cagtgatgaa    1380
```

```
agtgacagtg gcaaggctgt ggaagtgcag aacaagcaga tgattgaatg ggccctcggt   1440
ggcttccagc cctcgggtcc taagggcctg gagccaccag aagaagagaa gaatccttac   1500
aaggaagttt acaccgacat gtgggtggag cctgaagcag ctgcttacgc cccacccca   1560 ccagccaaga aacccagaaa gagcacaaca gagaaaccta aggtcaagga gatcattgat   1620
gagcgcacaa gggagcggct ggtgtatgag gtgcgccaga agtgcagaaa catcgaggac   1680
atttgtatct catgtgggag cctcaatgtc accctggagc acccactctt cattggaggc   1740
atgtgccaga actgtaagaa ctgcttcttg gagtgtgctt accagtatga cgacgatggg   1800
taccagtcct attgcaccat ctgctgtggg gggcgtgaag tgctcatgtg tgggaacaac   1860
aactgctgca ggtgcttttg tgtcgagtgt gtggatctct tggtggggcc aggagctgct   1920
caggcagcca ttaaggaaga cccctggaac tgctacatgt gcgggcataa gggcacctat   1980
gggctgctgc gaagacggga agactggcct tctcgactcc agatgttctt tgccaataac   2040
catgaccagg aatttgaccc cccaaaggtt tacccacctg tgccagctga aagaggaag   2100 cccatccgcg tgctgtctct ctttgatggg attgctacag ggctcctggt gctgaaggac   2160
ctgggcatcc aagtgaccg ctacattgcc tccgaggtgt gtgaggactc catcacggtg   2220
ggcatggtgc ggcaccaggg aaagatcatg tacgtcgggg acgtccgcag cgtcacacag   2280
aagcatatcc aggagtgggg cccattcgac ctggtgattg gaggcagtcc ctgcaatgac   2340
ctctccattg tcaaccctgc ccgcaaggga ctttatgagg gtactggccg cctcttcttt   2400
gagttctacc gcctcctgca tgatgcgcgg cccaaggagg gagatgatcg ccccttcttc   2460
tggctctttg agaatgtggt ggccatgggc gttagtgaca gagggacat ctcgcgattt   2520 cttgagtcta accccgtgat gattgacgcc aaagaagtgt ctgctgcaca cagggcccgt   2580
tacttctggg gtaaccttcc tggcatgaac aggcctttgg catccactgt gaatgataag   2640
ctggagctgc aagagtgtct ggagcacggc agaatagcca agttcagcaa agtgaggacc   2700
attaccacca ggtcaaactc tataaagcag ggcaaagacc agcatttccc cgtcttcatg   2760
aacgagaagg aggacatcct gtggtgcact gaaatggaaa gggtgtttgg cttccccgtc   2820
cactacacag acgtctccaa catgagccgc ttggcgaggc agagactgct gggccgatcg   2880
tggagcgtgc cggtcatccg ccacctcttc gctccgctga aggaatattt tgcttgtgtg   2940
taagggacat gggggcaaac tgaagtagtg atgataaaaa agttaaacaa acaaacaaac   3000
aaaaaacaaa acaaaacaat aaaacaccaa gaacgagagg acggagaaaa gttcagcacc   3060
cagaagagaa aaaggaattt aaagcaaacc acagaggagg aaaacgccgg agggcttggc   3120
cttgcaaaag ggttggacat catctcctga gttttcaatg ttaaccttca gtcctatcta   3180
aaaagcaaaa taggcccctc cccttcttcc cctccggtcc taggaggcga acttttttgtt   3240 ttctactctt tttcagaggg gttttctgtt tgtttgggtt tttgtttctt gctgtgactg   3300
aaacaagaga gttattgcag caaaatcagt aacaacaaaa agtagaaatg ccttggagag   3360
gaaagggaga gagggaaaat tctataaaaa cttaaaatat tggtttttt tttttttcct   3420 tttctatata tctctttggt tgtctctagc ctgatcagat aggagcacaa acaggaagag   3480
aatagagacc ctcggaggca gagtctcctc tcccacccc cgagcagtct caacagcacc   3540
attcctggtc atgcaaaaca gaacccaact agcagcaggg cgctgagaga acaccacacc   3600
agacactttc tacagtattt caggtgccta ccacacagga aaccttgaag aaaaccagtt   3660
tctagaagcc gctgttacct cttgtttaca gtttatatat atatgataga tatgagatat   3720
atatatataa aaggtactgt taactactgt acatcccgac ttcataatgg tgctttcaaa   3780
```

```
acagcgagat gagcaaagac atcagcttcc gcctggccct ctgtgcaaag ggtttcagcc    3840
caggatgggg agaggggagc agctggaggg ggttttaaca aactgaagga tgacccatat    3900 cacccccac ccctgcccca tgcctagctt cacctgccaa aaaggggctc agctgaggtg     3960
gtcggaccct ggggaagctg agtgtggaat ttatccagac tcgcgtgcaa taaccttaga    4020
atatgaatct aaaatgactg cctcagaaaa atggcttgag aaacattgt ccctgatttt     4080 gaattcgtca gccacgttga aggccccttg tgggatcaga atattccag agtgagggaa     4140 agtgacccgc cattaacccc ncctggagca aataaaaaaa catacaaaat gt             4192
```

<210> SEQ ID NO 2
<211> LENGTH: 4195
<212> TYPE: DNA
<213> ORGANISM: Mus musculus

<400> SEQUENCE: 2

```
gaattccggg cgccggggtt aagcggccca agtaaacgta gcgcagcgat cggcgccgga      60
gattcgcgaa cccgacactc cgcgccgccc gccggccagg acccgcggcg cgatcgcggc     120
gccgcgctac agccagcctc acgacaggcc cgctgaggct tgtgccagac cttggaaacc     180
tcaggtatat accttttccag acgcgggatc tcccctcccc catccatagt gccttgggac    240
caaatccagg gccttctttc aggaaacaat gaagggagac agcagacatc tgaatgaaga     300
agagggtgcc agcgggtatg aggagtgcat tatcgttaat gggaacttca gtgaccagtc     360
ctcagacacg aaggatgctc cctcaccccc agtcttggag gcaatctgca cagagccagt     420
ctgcacacca gagaccagag gccgcaggtc aagctcccgg ctgtctaaga gggaggtctc     480
cagccttctg aattacacgc aggacatgac aggagatgga gacagagatg atgaagtaga     540
tgatgggaat ggctctgata ttctaatgcc aaagctcacc cgtgagacca aggacaccag     600
gacgcgctct gaaagcccgg ctgtccgaac ccgacatagc aatgggacct ccagcttgga     660
gaggcaaaga gcctccccca gaatcacccg aggtcggcag ggccgccacc atgtgcagga     720
gtaccctgtg gagtttccgg ctaccaggtc tcggagacgt cgagcatcgt cttcagcaag     780
cacgccatgg tcatcccctg ccagcgtcga cttcatggaa gaagtgacac ctaagagcgt     840
cagtacccca tcagttgact tgagccagga tggagatcag gagggtatgg ataccacaca     900
ggtggatgca gagagcagag atggagacag cacagagtat caggatgata aagagtttgg     960
aataggtgac ctcgtgtggg gaaagatcaa gggcttctcc tggtggcctg ccatggtggt    1020
gtcctggaaa gccacctcca agcgacaggc catgcccgga atgcgctggg tacagtggtt    1080
tggtgatggc aagttttctg agatctctgc tgacaaactg gtggctctgg ggctgttcag    1140
ccagcacttt aatctggcta ccttcaataa gctggttcct tataggaagg ccatgtacca    1200
cactctggag aaagccaggg ttcgagctgg caagaccttc tccagcagtc ctggagagtc    1260
actggaggac cagctgaagc ccatgctgga gtgggcccac ggtggcttca gcctactgg     1320 gatcgagggc tcaaacccca caagaagca accagtggtt aataagtcga aggtgcgtcg    1380
ttcagacagt aggaacttag aacccaggag acgcgagaac aaaagtcgaa gacgcacaac    1440
caatgactct gctgcttctg agtcccccc acccaagcgc tcaagacaa atagctatgg      1500 cgggaaggac cgagggagg atgaggagag ccgagaacgg atggcttctg aagtcaccaa    1560
caacaagggc aatctggaag accgctgttt gtcctgtgga aagaagaacc ctgtgtcctt    1620 ccacccccctc tttgagggtg ggctctgtca gagttgccgg gatcgcttcc tagagctctt    1680
```

```
ctacatgtat gatgaggacg gctatcagtc ctactgcacc gtgtgctgtg agggccgtga   1740
actgctgctg tgcagtaaca caagctgctg cagatgcttc tgtgtggagt gtctggaggt   1800
gctggtgggc gcaggcacag ctgaggatgc caagctgcag gaaccctgga gctgctatat   1860
gtgcctccct cagcgctgcc atgggtcct  ccgacgcagg aaagattgga acatgcgcct   1920
gcaagacttc ttcactactg atcctgacct ggaagaattt gagccaccca agttgtaccc   1980
agcaattcct gcagccaaaa ggaggcccat tagagtcctg tctctgtttg atggaattgc   2040
aacgggtac  ttggtgctca aggagttggg tattaaagtg gaaaagtaca ttgcctccga   2100
agtctgtgca gagtccatcg ctgtgggaac tgttaagcat gaaggccaga tcaaatatgt   2160
caatgacgtc cggaaaatca ccaagaaaaa tattgaagag tggggcccgt tcgacttggt   2220
gattggtgga agcccatgca atgatctctc taacgtcaat cctgcccgca aaggtttata   2280
tgagggcaca ggaaggctct tcttcgagtt ttaccacttg ctgaattata cccgccccaa   2340
ggagggcgac aaccgtccat tcttctggat gttcgagaat gttgtggcca tgaaagtgaa   2400
tgacaagaaa gacatctcaa gattcctggc atgtaaccca gtgatgatcg atgccatcaa   2460
ggtgtctgct gctcacaggg cccggtactt ctggggtaac ctacccggaa tgaacaggcc   2520
cgtgatggct tcaaagaatg ataagctcga gctgcaggac tgcctggagt tcagtaggac   2580
agcaaagtta aagaaagtgc agacaataac caccaagtcg aactccatca gacagggcaa   2640
aaaccagctt ttccctgtag tcatgaatgg caaggacgac gttttgtggt gcactgagct   2700
cgaaaggatc ttcggcttcc ctgctcacta cacggacgtg tccaacatgg gccgcggcgc   2760
ccgtcagaag ctgctgggca ggtcctggag tgtaccggtc atcagacacc tgtttgcccc   2820
cttgaaggac tactttgcct gtgaatagtt ctacccagga ctggggagct ctcggtcaga   2880
gccagtgccc agagtcaccc ctccctgaag gcacctcacc tgtccccttt ttagctcacc   2940
tgtgtggggc ctcacatcac tgtacctcag cttttctcctg ctcagtggga gcagagcctc   3000
ctggcccttg caggggagcc ccggtgctcc ctccgtgtgc acagctcaga cctggctgct   3060
tagagtagcc cggcatggtg ctcatgttct cttaccctga aactttaaaa cttgaagtag   3120
gtagtaagat ggctttcttt taccctcctg agtttatcac tcagaagtga tggctaagat   3180
accaaaaaaa caaacaaaaa cagaaacaaa aacaaaaaaa aaacctcaac agctctctta   3240
gtactcaggt tcatgctgca aaatcacttg agattttgtt tttaagtaac ccgtgctcca   3300
catttgctgg aggatgctat tgtgaatgtg ggctcagatg agcaaggtca agggccaaa   3360
aaaaattccc cctctccccc caggagtatt tgaagatgat gtttatggtt taagtcttcc   3420
tggcaccttc cccttgcttt ggtacaaggg ctgaagtcct gttggtcttg tagcatttcc   3480
caggatgatg atgtcagcag ggatgacatc accaccttta gggcttttcc ctggcagggg   3540
cccatgtggc tagtcctcac gaagactgga gtagaatgtt tggagctcag gaagggtggg   3600
tggagtggcc ctcttccagg tgtgagggat acgaaggagg aagcttaggg aaatccattc   3660
cccactccct cttgccaaat gaggggccca gtccccaaca gctcaggtcc ccagaacccc   3720
ctagttcctc atgagaagct aggaccagaa gcacatcgtt ccccttatct gagcagtgtt   3780
tggggaacta cagtgaaaac cttctggaga tgttaaaagc ttttaccccc acgatagatt   3840
gtgttttaa  ggggtgcttt ttttaggggc atcactggag ataagaaagc tgcatttcag   3900
aaatgccatc gtaatggttt ttaaacacct tttacctaat tacaggtgct attttataga   3960
agcagacaac acttcttttt atgactctca gacttctatt ttcatgttac cattttttt    4020
gtaactcgca aggtgtgggc ttttgtaact tcacaggtgt ggggagagac tgccttgttt   4080
```

| | |
|---|---|
| caacagtttg tctccactgg tttctaattt ttaggtgcaa agatgacaga tgcccagagt | 4140 |
| ttacctttct ggttgattaa agttgtattt ctctaaaaaa aaaaaaaaaa aaaaa | 4195 |

<210> SEQ ID NO 3
<211> LENGTH: 4293
<212> TYPE: DNA
<213> ORGANISM: Homo sapiens

<400> SEQUENCE: 3

| | |
|---|---|
| gccgcggcac cagggcgcgc agccgggccg gcccgacccc accggccata cggtggagcc | 60 |
| atcgaagccc ccacccacag gctgacagag gcaccgttca ccagagggct caacaccggg | 120 |
| atctatgttt aagttttaac tctcgcctcc aaagaccacg ataattcctt ccccaaagcc | 180 |
| cagcagcccc ccagcccgc gcagccccag cctgcctccc ggcgcccaga tgcccgccat | 240 |
| gccctccagc ggccccgggg acaccagcag ctctgctgcg gagcgggagg aggaccgaaa | 300 |
| ggacggagag gagcaggagg agccgcgtgg caaggaggag cgccaagagc ccagcaccac | 360 |
| ggcacgaaag gtggggcggc ctgggaggaa gcgcaagcac ccccggtgg aaagcggtga | 420 |
| cacgccaaag gaccctgcgg tgatctccaa gtccccatcc atggcccagg actcaggcgc | 480 |
| ctcagagcta ttacccaatg gggacttgga aagcggagt gagcccccagc cagaggaggg | 540 |
| gagccctgct ggggggcaga agggcgggc cccagcagag ggagagggtg cagctgagac | 600 |
| cctgcctgaa gcctcaagag cagtggaaaa tggctgctgc accccaagg agggccgagg | 660 |
| agcccctgca gaagcgggca aagaacagaa ggagaccaac atcgaatcca tgaaaatgga | 720 |
| gggctcccgg ggccggctgc ggggtggctt ggctgggag tccagcctcc gtcagcggcc | 780 |
| catgccgagg ctcaccttcc aggcggggga cccctactac atcagcaagc gcaagcggga | 840 |
| cgagtggctg gcacgctgga aaagggaggc tgagaagaaa gccaaggtca ttgcaggaat | 900 |
| gaatgctgtg aagaaaaacc aggggcccgg ggagtctcag aaggtggagg aggccagccc | 960 |
| tcctgctgtg cagcagccca ctgaccccgc atcccccact gtggctacca cgcctgagcc | 1020 |
| cgtggggtcc gatgctgggg acaagaatgc caccaaagca ggcgatgacg agccagagta | 1080 |
| cgaggacggc cggggctttg gcattgggga gctggtgtgg gggaaactgc ggggcttctc | 1140 |
| ctggtggcca ggccgcattg tgtcttggtg gatgacgggc cggagccgag cagctgaagg | 1200 |
| caccgctggg gtcatgtggt tcggagacgg caaattctca gtggtgtgtg ttgagaagct | 1260 |
| gatgccgctg agctcgtttt gcagtgcgtt ccaccaggcc acgtacaaca gcagccccat | 1320 |
| gtaccgcaaa gccatctacg aggtcctgca ggtggccagc agccgcgcgg ggaagctgtt | 1380 |
| cccggtgtgc cacgacagcg atgagagtga cactgccaag gccgtggagg tgcagaacaa | 1440 |
| gcccatgatt gaatgggccc tgggggctt ccagccttct ggccctaagg gcctggagcc | 1500 |
| accagaagaa gagaagaatc cctacaaaga agtgtacacg acatgtgggg tggaacctga | 1560 |
| ggcagctgcc tacgcaccac ctccaccagc caaaaagccc cggaagagca cagcggagaa | 1620 |
| gcccaaggtc aaggagatta ttgatgagcg cacaagagag cggctggtgt acagggtgcg | 1680 |
| gcagaagtgc cggaacattg aggacatctg catctcctgt gggagcctca atgttaccct | 1740 |
| ggaacacccc ctcttcgttg gaggaatgtg ccaaaactgc aagaactgct ttctggagtg | 1800 |
| tgcgtaccag tacgacgacg acggctacca gtcctactgc accatctgct gtggggccg | 1860 |
| tgaggtgctc atgtgcggaa acaacaactg ctgcaggtgc ttttgcgtgg agtgtgtgga | 1920 |
| cctcttggtg gggccggggg ctgcccaggc agccattaag gaagaccct ggaactgcta | 1980 |

```
catgtgcggg cacaagggta cctacgggct gctgcggcgg cgagaggact ggccctcccg   2040
gctccagatg ttcttcgcta ataaccacga ccaggaattt gaccctccaa aggtttaccc   2100
acctgtccca gctgagaaga ggaagccat ccgggtgctg tctctctttg atggaatcgc    2160
tacagggctc ctggtgctga aggacttggg cattcaggtg gaccgctaca ttgcctcgga   2220
ggtgtgtgag gactccatca cggtgggcat ggtgcggcac caggggaaga tcatgtacgt   2280
cggggacgtc cgcagcgtca cacagaagca tatccaggag tggggcccat tcgatctggt   2340
gattggggc agtccctgca atgacctctc catcgtcaac cctgctcgca agggcctcta    2400
cgagggcact ggccggctct tctttgagtt ctaccgcctc ctgcatgatg cgcggcccaa   2460
ggagggagat gatcgcccct tcttctggct ctttgagaat gtggtggcca tgggcgttag   2520
tgacaagagg gacatctcgc gatttctcga gtccaaccct gtgatgattg atgccaaaga   2580
agtgtcagct gcacacaggg cccgctactt ctggggtaac cttcccggta tgaacaggcc   2640
gttggcatcc actgtgaatg ataagctgga gctgcaggag tgtctggagc atggcaggat   2700
agccaagttc agcaaagtga ggaccattac tacgaggtca aactccataa agcagggcaa   2760
agaccagcat tttcctgtct tcatgaatga gaaagaggac atcttatggt gcactgaaat   2820
ggaaagggta tttggtttcc cagtccacta tactgacgtc tccaacatga gccgcttggc   2880
gaggcagaga ctgctgggcc ggtcatggag cgtgccagtc atccgccacc tcttcgctcc   2940
gctgaaggag tattttgcgt gtgtgtaagg gacatggggg caaactgagg tagcgacaca   3000
aagttaaaca acaaacaaa aaacacaaaa cataataaaa caccaagaac atgaggatgg    3060
agagaagtat cagcacccag aagagaaaaa ggaatttaaa acaaaaacca cagaggcgga   3120
aataccggag ggctttgcct tgcgaaaagg gttggacatc atctcctgat ttttcaatgt   3180
tattcttcag tcctatttaa aaacaaaacc aagctccctt cccttcctcc cccttccctt   3240
tttttttcggt cagaccttt attttctact cttttcagag gggttttctg tttgtttggg    3300
ttttgtttct tgctgtgact gaaacaagaa ggttattgca gcaaaaatca gtaacaaaaa   3360
atagtaacaa taccttgcag aggaaaggtg ggaggagagg aaaaaaggga aattttaaa    3420
gaaatctata tattgggttg tttttttttt tgtttttgt tttttttttt tgggtttttt    3480
tttttacta tatatctttt ttttgttgtc tctagcctga tcagatagga gcacaagcag    3540
gggacggaaa gagagagaca ctcaggcggc agcattccct cccagccact gagctgtcgt   3600
gccagcacca ttcctggtca cgcaaaacag aacccagtta gcagcaggga gacgagaaca   3660
ccacacaaga cattttctct a cagtatttca ggtgcctacc acacaggaaa ccttgaagaa  3720
aatcagtttc tagaagccgc tgttacctct tgtttacagt ttatatatat atgatagata   3780
tgagatatat atataaaagg tactgttaac tactgtacaa cccgacttca taatggtgct   3840
ttcaaacagc gagatgagta aaaacatcag cttccacgtt gccttctgcg caaagggttt   3900
caccaaggat ggagaaaggg agacagcttg cagatgcgc gttctcacgg tgggctcttc    3960
ccccttggttt gtaacgaagt gaaggaggag aacttgggag ccaggttctc cctgccaaaa   4020
agggggctag atgaggtggt cgggcccgtg gacagctgag agtgggattc atccagactc    4080
atgcaataac cctttgattg ttttctaaaa ggagactccc tcggcaagat ggcagagggt   4140
acggagtctt caggcccagt ttctcacttt agccaattcg agggctcctt gtggtgggat   4200
cagaactaat ccagagtgtg ggaaagtgac agtcaaaacc ccacctggag caaataaaaa   4260
aacatacaaa acgtaaaaaa aaaaaaaaa aaa                                  4293
```

<210> SEQ ID NO 4
<211> LENGTH: 4145
<212> TYPE: DNA
<213> ORGANISM: Homo sapiens

<400> SEQUENCE: 4

| | | | | | |
|---|---|---|---|---|---|
| ggccgcgaat | tcggcacgag | ccctgcacgg | ccgccagccg | gcctcccgcc | agccagcccc | 60 |
| gacccgcggc | tccgccgccc | agccgcgccc | cagccagccc | tgcggcagga | aagcatgaag | 120 |
| ggagacacca | ggcatctcaa | tggagaggag | gacgccggcg | ggagggaaga | ctcgatcctc | 180 |
| gtcaacgggg | cctgcagcga | ccagtcctcc | gactcgcccc | caatcctgga | ggctatccgc | 240 |
| accccggaga | tcagaggccg | aagatcaagc | tcgcgactct | ccaagaggga | ggtgtccagt | 300 |
| ctgctaagct | acacacagga | cttgacagge | gatggcgacg | gggaagatgg | ggatggctct | 360 |
| gacacccag | tcatgccaaa | gctcttccgg | gaaaccagga | ctcgttcaga | aagcccagct | 420 |
| gtccgaactc | gaaataacaa | cagtgtctcc | agccgggaga | ggcacaggcc | ttccccacgt | 480 |
| tccacccgag | gccggcaggg | ccgcaaccat | gtggacgagt | ccccgtgga | gttcccggct | 540 |
| accaggtccc | tgagacggcg | ggcaacagca | tcggcaggaa | cgccatggcc | gtcccctccc | 600 |
| agctcttacc | ttaccatcga | cctcacagac | gacacagagg | acacacatgg | gacgccccag | 660 |
| agcagcagta | cccctacgc | ccgcctagcc | caggacagcc | agcagggggg | catggagtcc | 720 |
| ccgcaggtgg | aggcagacag | tggagatgga | gacagttcag | agtatcagga | tgggaaggag | 780 |
| tttggaatag | ggaccctcgt | gtggggaaag | atcaagggct | tctcctggtg | gcccgccatg | 840 |
| gtggtgtctt | ggaaggccac | ctccaagcga | caggctatgt | ctggcatgcg | gtgggtccag | 900 |
| tggtttggcg | atggcaagtt | ctccgaggtc | tctgcagaca | aactggtggc | actggggctg | 960 |
| ttcagccagc | actttaattt | ggccaccttc | aataagctcg | tctcctatcg | aaaagccatg | 1020 |
| taccatgctc | tggagaaagc | tagggtgcga | gctggcaaga | ccttccccag | cagccctgga | 1080 |
| gactcattgg | aggaccagct | gaagcccatg | ttggagtggg | cccacggggg | cttcaagccc | 1140 |
| actgggatcg | agggcctcaa | acccaacaac | acgcaaccag | tggttaataa | gtcgaaggtg | 1200 |
| cgtcgtgcag | gcagtaggaa | attagaatca | aggaaatacg | agaacaagac | tcgaagacgc | 1260 |
| acagctgacg | actcagccac | ctctgactac | tgccccgcac | ccaagcgcct | caagacaaat | 1320 |
| tgctataaca | acggcaaaga | ccgaggggat | gaagatcaga | gccgagaaca | aatggcttca | 1380 |
| gatgttgcca | caacaagag | cagcctggaa | gatggctgtt | tgtcttgtgg | caggaaaaac | 1440 |
| cccgtgtcct | tccaccctct | ctttgagggg | gggctctgtc | agacatgccg | ggatcgcttc | 1500 |
| cttgagctgt | tttacatgta | tgatgacgat | ggctatcagt | cttactgcac | tgtgtgctgc | 1560 |
| gagggccgag | agctgctgct | tgcagcaac | acgagctgct | gccggtgttt | ctgtgtggag | 1620 |
| tgcctggagg | tgctggtggg | cacaggcaca | gcggccgagg | ccaagcttca | ggagccctgg | 1680 |
| agctgctaca | tgtgtctccc | gcagcgctgt | catggcgtcc | tgcggcgccg | gaaggactgg | 1740 |
| aacgtgcgcc | tgcaggcctt | cttcaccagt | gacacggggc | ttgaatacga | agcccccaag | 1800 |
| ctgtaccctg | ccattcccgc | agcccgaagg | cggcccattc | gagtcctgtc | attgtttgat | 1860 |
| ggcatcgcga | caggctacct | agtcctcaaa | gagttgggca | taaaggtagg | aaagtacgtc | 1920 |
| gcttctgaag | tgtgtgagga | gtccattgct | gttggaaccg | tgaagcacga | ggggaatatc | 1980 |
| aaatacgtga | acgacgtgag | gaacatcaca | aagaaaaata | ttgaagaatg | ggcccatt | 2040 |
| gacttggtga | ttggcggaag | cccatgcaac | gatctctcaa | atgtgaatcc | agccaggaaa | 2100 |
| ggcctgtatg | agggtacagg | ccggctcttc | ttcgaatttt | accacctgct | gaattactca | 2160 |

-continued

```
cgccccaagg agggtgatga ccggccgttc ttctggatgt ttgagaatgt tgtagccatg    2220
aaggttggcg acaagaggga catctcacgg ttcctggagt gtaatccagt gatgattgat    2280
gccatcaaag tttctgctgc tcacagggcc cgatacttct ggggcaacct acccgggatg    2340
aacaggcccg tgatagcatc aaagaatgat aaactcgagc tgcaggactg cttggaatac    2400
aataggatag ccaagttaaa gaaagtacag acaataacca ccaagtcgaa ctcgatcaaa    2460
caggggaaaa accaactttt ccctgttgtc atgaatggca agaagatgt tttgtggtgc     2520 actgagctcg aaaggatctt tggctttcct gtgcactaca cagacgtgtc caacatgggc    2580
cgtggtgccc gccagaagct gctgggaagg tcctggagcg tgcctgtcat ccgacacctc    2640
ttcgcccctc tgaaggacta ctttgcatgt gaatagttcc agccaggccc aagcccact    2700 ggggtgtgtg gcagagccag gacccaggag gtgtgattcc tgaaggcatc cccaggccct    2760
gctcttcctc agctgtgtgg gtcataccgt gtacctcagt tccctcttgc tcagtggggg    2820
cagagccacc tgactcttgc aggggtagcc tgaggtgccg cctccttgtg cacaaatcag    2880
acctggctgc ttggagcagc ctaacacggt gctcattttt tcttctccta aaactttaaa    2940
acttgaagta ggtagcaacg tggctttttt ttttccctt cctgggtcta ccactcagag    3000
aaacaatggc taagatacca aaaccacagt gccgacagct ctccaatact caggttaatg    3060
ctgaaaaatc atccaagaca gttattgcaa gagtttaatt tttgaaaact gggtactgct    3120
atgtgtttac agacgtgtgc agttgtaggc atgtagctac aggacatttt taagggccca    3180
ggatcgtttt ttcccagggc aagcagaaga gaaaatgttg tatatgtctt ttacccggca    3240
cattcccctt gcctaaatac aagggctgga gtctgcacgg gacctattag agtattttcc    3300
acaatgatga tgatttcagc agggatgacg tcatcatcac attcagggct attttttccc    3360
ccacaaaccc aagggcaggg gccactctta gctaaatccc tccccgtgac tgcaatagaa    3420
ccctctgggg agctcaggaa ggggtgtgct gagttctata atataagctg ccatatattt    3480
tgtagacaag tatggctcct ccatatctcc ctcttcccta ggagaggagt gtgaagcaag    3540
gagcttagat aagacacccc ctcaaaccca ttccctctcc aggagaccta ccctccacag    3600
gcacaggtcc ccagatgaga agtctgctac cctcatttct catcttttta ctaaactcag    3660
aggcagtgac agcagtcagg gacagacata catttctcat accttcccca catctgagag    3720
atgacaggga aaactgcaaa gctcggtgct ccctttggag attttttaat cctttttat    3780 tccataagaa gtcgttttta gggagaacgg gaattcagac aagctgcatt tcagaaatgc    3840
tgtcataatg gtttttaaca ccttttactc ttcttactgg tgctatttg tagaataagg    3900 aacaacgttg acaagttttg tggggctttt tatacacttt ttaaaatctc aaacttctat    3960
ttttatgttt aacgttttca ttaaaatttt tttgtaactg gagccacgac gtaacaaata    4020
tggggaaaaa actgtgcctt gtttcaacag ttttttgctaa ttttaggct gaaagatgac    4080 ggatgcctag agttaccttt atgtttaatt aaaatcagta tttgtctaaa aaaaaaaaa    4140 aaaaa                                                                4145
```

<210> SEQ ID NO 5
<211> LENGTH: 908
<212> TYPE: PRT
<213> ORGANISM: Mus musculus

<400> SEQUENCE: 5

```
Met Pro Ser Ser Gly Pro Gly Asp Thr Ser Ser Ser Ser Leu Glu Arg
 1               5                  10                  15
```

-continued

```
Glu Asp Asp Arg Lys Glu Gly Glu Gln Glu Glu Asn Arg Gly Lys
                20                  25                  30
Glu Glu Arg Gln Glu Pro Ser Ala Thr Ala Arg Lys Val Gly Arg Pro
            35                  40                  45
Gly Arg Lys Arg Lys His Pro Pro Val Glu Ser Ser Asp Thr Pro Lys
        50                  55                  60
Asp Pro Ala Val Thr Thr Lys Ser Gln Pro Met Ala Gln Asp Ser Gly
65                  70                  75                  80
Pro Ser Asp Leu Leu Pro Asn Gly Asp Leu Glu Lys Arg Ser Glu Pro
                85                  90                  95
Gln Pro Glu Glu Gly Ser Pro Ala Ala Gly Gln Lys Gly Gly Ala Pro
            100                 105                 110
Ala Glu Gly Glu Gly Thr Glu Thr Pro Pro Glu Ala Ser Arg Ala Val
        115                 120                 125
Glu Asn Gly Cys Cys Val Thr Lys Glu Gly Arg Gly Ala Ser Ala Gly
130                 135                 140
Glu Gly Lys Glu Gln Lys Gln Thr Asn Ile Glu Ser Met Lys Met Glu
145                 150                 155                 160
Gly Ser Arg Gly Arg Leu Arg Gly Gly Leu Gly Trp Glu Ser Ser Leu
                165                 170                 175
Arg Gln Arg Pro Met Pro Arg Leu Thr Phe Gln Ala Gly Asp Pro Tyr
            180                 185                 190
Tyr Ile Ser Lys Arg Lys Arg Asp Glu Trp Leu Ala Arg Trp Lys Arg
        195                 200                 205
Glu Ala Glu Lys Lys Ala Lys Val Ile Ala Val Met Asn Ala Val Glu
210                 215                 220
Glu Asn Gln Ala Ser Gly Glu Ser Gln Lys Val Glu Glu Ala Ser Pro
225                 230                 235                 240
Pro Ala Val Gln Gln Pro Thr Asp Pro Ala Ser Pro Thr Val Ala Thr
                245                 250                 255
Thr Pro Glu Pro Val Gly Gly Asp Ala Gly Asp Lys Asn Ala Thr Lys
            260                 265                 270
Ala Ala Asp Asp Glu Pro Glu Tyr Glu Asp Gly Arg Gly Phe Gly Ile
        275                 280                 285
Gly Glu Leu Val Trp Gly Lys Leu Arg Gly Phe Ser Trp Trp Pro Gly
290                 295                 300
Arg Ile Val Ser Trp Trp Met Thr Gly Arg Ser Arg Ala Ala Glu Gly
305                 310                 315                 320
Thr Arg Trp Val Met Trp Phe Gly Asp Gly Lys Phe Ser Val Val Cys
                325                 330                 335
Val Glu Lys Leu Met Pro Leu Ser Ser Phe Cys Ser Ala Phe His Gln
            340                 345                 350
Ala Thr Tyr Asn Lys Gln Pro Met Tyr Arg Lys Ala Ile Tyr Glu Val
        355                 360                 365
Leu Gln Val Ala Ser Ser Arg Ala Gly Lys Leu Phe Pro Ala Cys His
370                 375                 380
Asp Ser Asp Glu Ser Asp Ser Gly Lys Ala Val Glu Val Gln Asn Lys
385                 390                 395                 400
Gln Met Ile Glu Trp Ala Leu Gly Gly Phe Gln Pro Ser Gly Pro Lys
                405                 410                 415
Gly Leu Glu Pro Pro Glu Glu Glu Lys Asn Pro Tyr Lys Glu Val Tyr
            420                 425                 430
Thr Asp Met Trp Val Glu Pro Glu Ala Ala Ala Tyr Ala Pro Pro Pro
```

-continued

```
            435                 440                 445
Pro Ala Lys Lys Pro Arg Lys Ser Thr Thr Glu Lys Pro Lys Val Lys
450                 455                 460
Glu Ile Ile Asp Glu Arg Thr Arg Glu Arg Leu Val Tyr Glu Val Arg
465                 470                 475                 480
Gln Lys Cys Arg Asn Ile Glu Asp Ile Cys Ile Ser Cys Gly Ser Leu
                485                 490                 495
Asn Val Thr Leu Glu His Pro Leu Phe Ile Gly Met Cys Gln Asn
                500                 505                 510
Cys Lys Asn Cys Phe Leu Glu Cys Ala Tyr Gln Tyr Asp Asp Asp Gly
            515                 520                 525
Tyr Gln Ser Tyr Cys Thr Ile Cys Cys Gly Arg Glu Val Leu Met
            530                 535                 540
Cys Gly Asn Asn Cys Cys Arg Cys Phe Cys Val Glu Cys Val Asp
545                 550                 555                 560
Leu Leu Val Gly Pro Gly Ala Ala Gln Ala Ala Ile Lys Glu Asp Pro
                565                 570                 575
Trp Asn Cys Tyr Met Cys Gly His Lys Gly Thr Tyr Gly Leu Leu Arg
                580                 585                 590
Arg Arg Glu Asp Trp Pro Ser Arg Leu Gln Met Phe Phe Ala Asn Asn
            595                 600                 605
His Asp Gln Glu Phe Asp Pro Pro Lys Val Tyr Pro Pro Val Pro Ala
            610                 615                 620
Glu Lys Arg Lys Pro Ile Arg Val Leu Ser Leu Phe Asp Gly Ile Ala
625                 630                 635                 640
Thr Gly Leu Leu Val Leu Lys Asp Leu Gly Ile Gln Val Asp Arg Tyr
                645                 650                 655
Ile Ala Ser Glu Val Cys Glu Asp Ser Ile Thr Val Gly Met Val Arg
                660                 665                 670
His Gln Gly Lys Ile Met Tyr Val Gly Asp Val Arg Ser Val Thr Gln
            675                 680                 685
Lys His Ile Gln Glu Trp Gly Pro Phe Asp Leu Val Ile Gly Gly Ser
            690                 695                 700
Pro Cys Asn Asp Leu Ser Ile Val Asn Pro Ala Arg Lys Gly Leu Tyr
705                 710                 715                 720
Glu Gly Thr Gly Arg Leu Phe Phe Glu Phe Tyr Arg Leu Leu His Asp
                725                 730                 735
Ala Arg Pro Lys Glu Gly Asp Asp Arg Pro Phe Phe Trp Leu Phe Glu
                740                 745                 750
Asn Val Val Ala Met Gly Val Ser Asp Lys Arg Asp Ile Ser Arg Phe
            755                 760                 765
Leu Glu Ser Asn Pro Val Met Ile Asp Ala Lys Glu Val Ser Ala Ala
770                 775                 780
His Arg Ala Arg Tyr Phe Trp Gly Asn Leu Pro Gly Met Asn Arg Pro
785                 790                 795                 800
Leu Ala Ser Thr Val Asn Asp Lys Leu Glu Leu Gln Glu Cys Leu Glu
                805                 810                 815
His Gly Arg Ile Ala Lys Phe Ser Lys Val Arg Thr Ile Thr Thr Arg
            820                 825                 830
Ser Asn Ser Ile Lys Gln Gly Lys Asp Gln His Phe Pro Val Phe Met
            835                 840                 845
Asn Glu Lys Glu Asp Ile Leu Trp Cys Thr Glu Met Glu Arg Val Phe
850                 855                 860
```

```
Gly Phe Pro Val His Tyr Thr Asp Val Ser Asn Met Ser Arg Leu Ala
865                 870                 875                 880

Arg Gln Arg Leu Leu Gly Arg Ser Trp Ser Val Pro Val Ile Arg His
            885                 890                 895

Leu Phe Ala Pro Leu Lys Glu Tyr Phe Ala Cys Val
            900                 905

<210> SEQ ID NO 6
<211> LENGTH: 859
<212> TYPE: PRT
<213> ORGANISM: Mus musculus

<400> SEQUENCE: 6

Met Lys Gly Asp Ser Arg His Leu Asn Glu Glu Gly Ala Ser Gly
  1               5                  10                  15

Tyr Glu Glu Cys Ile Ile Val Asn Gly Asn Phe Ser Asp Gln Ser Ser
                 20                  25                  30

Asp Thr Lys Asp Ala Pro Ser Pro Val Leu Glu Ala Ile Cys Thr
             35                  40                  45

Glu Pro Val Cys Thr Pro Glu Thr Arg Gly Arg Arg Ser Ser Ser Arg
 50                  55                  60

Leu Ser Lys Arg Glu Val Ser Ser Leu Leu Asn Tyr Thr Gln Asp Met
 65                  70                  75                  80

Thr Gly Asp Gly Asp Arg Asp Asp Glu Val Asp Asp Gly Asn Gly Ser
                 85                  90                  95

Asp Ile Leu Met Pro Lys Leu Thr Arg Glu Thr Lys Asp Thr Arg Thr
                100                 105                 110

Arg Ser Glu Ser Pro Ala Val Arg Thr Arg His Ser Asn Gly Thr Ser
            115                 120                 125

Ser Leu Glu Arg Gln Arg Ala Ser Pro Arg Ile Thr Arg Gly Arg Gln
        130                 135                 140

Gly Arg His His Val Gln Glu Tyr Pro Val Glu Phe Pro Ala Thr Arg
145                 150                 155                 160

Ser Arg Arg Arg Arg Ala Ser Ser Ser Ala Ser Thr Pro Trp Ser Ser
                165                 170                 175

Pro Ala Ser Val Asp Phe Met Glu Glu Val Thr Pro Lys Ser Val Ser
                180                 185                 190

Thr Pro Ser Val Asp Leu Ser Gln Asp Gly Asp Gln Glu Gly Met Asp
            195                 200                 205

Thr Thr Gln Val Asp Ala Glu Ser Arg Asp Gly Asp Ser Thr Glu Tyr
        210                 215                 220

Gln Asp Asp Lys Glu Phe Gly Ile Gly Asp Leu Val Trp Gly Lys Ile
225                 230                 235                 240

Lys Gly Phe Ser Trp Trp Pro Ala Met Val Val Ser Trp Lys Ala Thr
                245                 250                 255

Ser Lys Arg Gln Ala Met Pro Gly Met Arg Trp Val Gln Trp Phe Gly
            260                 265                 270

Asp Gly Lys Phe Ser Glu Ile Ser Ala Asp Lys Leu Val Ala Leu Gly
        275                 280                 285

Leu Phe Ser Gln His Phe Asn Leu Ala Thr Phe Asn Lys Leu Val Ser
    290                 295                 300

Tyr Arg Lys Ala Met Tyr His Thr Leu Glu Lys Ala Arg Val Arg Ala
305                 310                 315                 320

Gly Lys Thr Phe Ser Ser Ser Pro Gly Glu Ser Leu Glu Asp Gln Leu
```

-continued

```
                325                 330                 335
Lys Pro Met Leu Glu Trp Ala His Gly Gly Phe Lys Pro Thr Gly Ile
                340                 345                 350
Glu Gly Leu Lys Pro Asn Lys Lys Gln Pro Val Val Asn Lys Ser Lys
                355                 360                 365
Val Arg Arg Ser Asp Ser Arg Asn Leu Glu Pro Arg Arg Glu Asn
        370                 375                 380
Lys Ser Arg Arg Arg Thr Thr Asn Asp Ser Ala Ala Ser Glu Ser Pro
385                 390                 395                 400
Pro Pro Lys Arg Leu Lys Thr Asn Ser Tyr Gly Gly Lys Asp Arg Gly
                405                 410                 415
Glu Asp Glu Glu Ser Arg Glu Arg Met Ala Ser Glu Val Thr Asn Asn
                420                 425                 430
Lys Gly Asn Leu Glu Asp Arg Cys Leu Ser Cys Gly Lys Lys Asn Pro
        435                 440                 445
Val Ser Phe His Pro Leu Phe Glu Gly Gly Leu Cys Gln Ser Cys Arg
        450                 455                 460
Asp Arg Phe Leu Glu Leu Phe Tyr Met Tyr Asp Glu Asp Gly Tyr Gln
465                 470                 475                 480
Ser Tyr Cys Thr Val Cys Cys Glu Gly Arg Glu Leu Leu Cys Ser
                485                 490                 495
Asn Thr Ser Cys Cys Arg Cys Phe Cys Val Glu Cys Leu Glu Val Leu
                500                 505                 510
Val Gly Ala Gly Thr Ala Glu Asp Ala Lys Leu Gln Glu Pro Trp Ser
        515                 520                 525
Cys Tyr Met Cys Leu Pro Gln Arg Cys His Gly Val Leu Arg Arg Arg
        530                 535                 540
Lys Asp Trp Asn Met Arg Leu Gln Asp Phe Phe Thr Thr Asp Pro Asp
545                 550                 555                 560
Leu Glu Glu Phe Glu Pro Pro Lys Leu Tyr Pro Ala Ile Pro Ala Ala
                565                 570                 575
Lys Arg Arg Pro Ile Arg Val Leu Ser Leu Phe Asp Gly Ile Ala Thr
        580                 585                 590
Gly Tyr Leu Val Leu Lys Glu Leu Gly Ile Lys Val Glu Lys Tyr Ile
        595                 600                 605
Ala Ser Glu Val Cys Ala Glu Ser Ile Ala Val Gly Thr Val Lys His
        610                 615                 620
Glu Gly Gln Ile Lys Tyr Val Asn Asp Val Arg Lys Ile Thr Lys Lys
625                 630                 635                 640
Asn Ile Glu Glu Trp Gly Pro Phe Asp Leu Val Ile Gly Gly Ser Pro
                645                 650                 655
Cys Asn Asp Leu Ser Asn Val Asn Pro Ala Arg Lys Gly Leu Tyr Glu
                660                 665                 670
Gly Thr Gly Arg Leu Phe Phe Glu Phe Tyr His Leu Leu Asn Tyr Thr
        675                 680                 685
Arg Pro Lys Glu Gly Asp Asn Arg Pro Phe Phe Trp Met Phe Glu Asn
        690                 695                 700
Val Val Ala Met Lys Val Asn Asp Lys Asp Ile Ser Arg Phe Leu
705                 710                 715                 720
Ala Cys Asn Pro Val Met Ile Asp Ala Ile Lys Val Ser Ala Ala His
                725                 730                 735
Arg Ala Arg Tyr Phe Trp Gly Asn Leu Pro Gly Met Asn Arg Pro Val
                740                 745                 750
```

```
Met Ala Ser Lys Asn Asp Lys Leu Glu Leu Gln Asp Cys Leu Glu Phe
        755                 760                 765

Ser Arg Thr Ala Lys Leu Lys Val Gln Thr Ile Thr Thr Lys Ser
        770                 775                 780

Asn Ser Ile Arg Gln Gly Lys Asn Gln Leu Phe Pro Val Val Met Asn
785                 790                 795                 800

Gly Lys Asp Val Leu Trp Cys Thr Glu Leu Glu Arg Ile Phe Gly
                805                 810                 815

Phe Pro Ala His Tyr Thr Asp Val Ser Asn Met Gly Arg Gly Ala Arg
                820                 825                 830

Gln Lys Leu Leu Gly Arg Ser Trp Ser Val Pro Val Ile Arg His Leu
        835                 840                 845

Phe Ala Pro Leu Lys Asp Tyr Phe Ala Cys Glu
        850                 855

<210> SEQ ID NO 7
<211> LENGTH: 912
<212> TYPE: PRT
<213> ORGANISM: Homo sapiens

<400> SEQUENCE: 7

Met Pro Ala Met Pro Ser Ser Gly Pro Gly Asp Thr Ser Ser Ser Ala
 1               5                  10                  15

Ala Glu Arg Glu Glu Asp Arg Lys Asp Gly Glu Glu Gln Glu Glu Pro
                20                  25                  30

Arg Gly Lys Glu Glu Arg Gln Glu Pro Ser Thr Thr Ala Arg Lys Val
            35                  40                  45

Gly Arg Pro Gly Arg Lys Arg Lys His Pro Pro Val Glu Ser Gly Asp
        50                  55                  60

Thr Pro Lys Asp Pro Ala Val Ile Ser Lys Ser Pro Ser Met Ala Gln
65                  70                  75                  80

Asp Ser Gly Ala Ser Glu Leu Leu Pro Asn Gly Asp Leu Glu Lys Arg
                85                  90                  95

Ser Glu Pro Gln Pro Glu Glu Gly Ser Pro Ala Gly Gly Gln Lys Gly
                100                 105                 110

Gly Ala Pro Ala Glu Gly Glu Gly Ala Ala Glu Thr Leu Pro Glu Ala
            115                 120                 125

Ser Arg Ala Val Glu Asn Gly Cys Cys Thr Pro Lys Glu Gly Arg Gly
        130                 135                 140

Ala Pro Ala Glu Ala Gly Lys Glu Gln Lys Glu Thr Asn Ile Glu Ser
145                 150                 155                 160

Met Lys Met Glu Gly Ser Arg Gly Arg Leu Arg Gly Gly Leu Gly Trp
                165                 170                 175

Glu Ser Ser Leu Arg Gln Arg Pro Met Pro Arg Leu Thr Phe Gln Ala
                180                 185                 190

Gly Asp Pro Tyr Tyr Ile Ser Lys Arg Lys Arg Asp Glu Trp Leu Ala
            195                 200                 205

Arg Trp Lys Arg Glu Ala Glu Lys Lys Ala Lys Val Ile Ala Gly Met
        210                 215                 220

Asn Ala Val Glu Glu Asn Gln Gly Pro Gly Glu Ser Gln Lys Val Glu
225                 230                 235                 240

Glu Ala Ser Pro Pro Ala Val Gln Gln Pro Thr Asp Pro Ala Ser Pro
                245                 250                 255

Thr Val Ala Thr Thr Pro Glu Pro Val Gly Ser Asp Ala Gly Asp Lys
```

-continued

```
                260                 265                 270
Asn Ala Thr Lys Ala Gly Asp Asp Glu Pro Glu Tyr Glu Asp Gly Arg
            275                 280                 285
Gly Phe Gly Ile Gly Glu Leu Val Trp Gly Lys Leu Arg Gly Phe Ser
        290                 295                 300
Trp Trp Pro Gly Arg Ile Val Ser Trp Trp Met Thr Gly Arg Ser Arg
305                 310                 315                 320
Ala Ala Glu Gly Thr Arg Trp Val Met Trp Phe Gly Asp Gly Lys Phe
                325                 330                 335
Ser Val Val Cys Val Glu Lys Leu Met Pro Leu Ser Ser Phe Cys Ser
            340                 345                 350
Ala Phe His Gln Ala Thr Tyr Asn Lys Gln Pro Met Tyr Arg Lys Ala
        355                 360                 365
Ile Tyr Glu Val Leu Gln Val Ala Ser Ser Arg Ala Gly Lys Leu Phe
    370                 375                 380
Pro Val Cys His Asp Ser Asp Glu Ser Asp Thr Ala Lys Ala Val Glu
385                 390                 395                 400
Val Gln Asn Lys Pro Met Ile Glu Trp Ala Leu Gly Gly Phe Gln Pro
                405                 410                 415
Ser Gly Pro Lys Gly Leu Glu Pro Pro Glu Glu Lys Asn Pro Tyr
            420                 425                 430
Lys Glu Val Tyr Thr Asp Met Trp Val Glu Pro Glu Ala Ala Tyr
        435                 440                 445
Ala Pro Pro Pro Ala Lys Lys Pro Arg Lys Ser Thr Ala Glu Lys
    450                 455                 460
Pro Lys Val Lys Glu Ile Ile Asp Glu Arg Thr Arg Glu Arg Leu Val
465                 470                 475                 480
Tyr Glu Val Arg Gln Lys Cys Arg Asn Ile Glu Asp Ile Cys Ile Ser
                485                 490                 495
Cys Gly Ser Leu Asn Val Thr Leu Glu His Pro Leu Phe Val Gly Gly
            500                 505                 510
Met Cys Gln Asn Cys Lys Asn Cys Phe Leu Glu Cys Ala Tyr Gln Tyr
        515                 520                 525
Asp Asp Asp Gly Tyr Gln Ser Tyr Cys Thr Ile Cys Cys Gly Gly Arg
    530                 535                 540
Glu Val Leu Met Cys Gly Asn Asn Asn Cys Cys Arg Cys Phe Cys Val
545                 550                 555                 560
Glu Cys Val Asp Leu Leu Val Gly Pro Gly Ala Ala Gln Ala Ala Ile
                565                 570                 575
Lys Glu Asp Pro Trp Asn Cys Tyr Met Cys Gly His Lys Gly Thr Tyr
            580                 585                 590
Gly Leu Leu Arg Arg Arg Glu Asp Trp Pro Ser Arg Leu Gln Met Phe
        595                 600                 605
Phe Ala Asn Asn His Asp Gln Glu Phe Asp Pro Pro Lys Val Tyr Pro
    610                 615                 620
Pro Val Pro Ala Glu Lys Arg Lys Pro Ile Arg Val Leu Ser Leu Phe
625                 630                 635                 640
Asp Gly Ile Ala Thr Gly Leu Leu Val Leu Lys Asp Leu Gly Ile Gln
                645                 650                 655
Val Asp Arg Tyr Ile Ala Ser Glu Val Cys Glu Asp Ser Ile Thr Val
            660                 665                 670
Gly Met Val Arg His Gln Gly Lys Ile Met Tyr Val Gly Asp Val Arg
        675                 680                 685
```

```
Ser Val Thr Gln Lys His Ile Gln Glu Trp Gly Pro Phe Asp Leu Val
    690                 695                 700

Ile Gly Gly Ser Pro Cys Asn Asp Leu Ser Ile Val Asn Pro Ala Arg
705                 710                 715                 720

Lys Gly Leu Tyr Glu Gly Thr Gly Arg Leu Phe Phe Glu Phe Tyr Arg
                725                 730                 735

Leu Leu His Asp Ala Arg Pro Lys Glu Gly Asp Asp Arg Pro Phe Phe
            740                 745                 750

Trp Leu Phe Glu Asn Val Val Ala Met Gly Val Ser Asp Lys Arg Asp
        755                 760                 765

Ile Ser Arg Phe Leu Glu Ser Asn Pro Val Met Ile Asp Ala Lys Glu
    770                 775                 780

Val Ser Ala Ala His Arg Ala Arg Tyr Phe Trp Gly Asn Leu Pro Gly
785                 790                 795                 800

Met Asn Arg Pro Leu Ala Ser Thr Val Asn Asp Lys Leu Glu Leu Gln
                805                 810                 815

Glu Cys Leu Glu His Gly Arg Ile Ala Lys Phe Ser Lys Val Arg Thr
            820                 825                 830

Ile Thr Thr Arg Ser Asn Ser Ile Lys Gln Gly Lys Asp Gln His Phe
        835                 840                 845

Pro Val Phe Met Asn Glu Lys Glu Asp Ile Leu Trp Cys Thr Glu Met
    850                 855                 860

Glu Arg Val Phe Gly Phe Pro Val His Tyr Thr Asp Val Ser Asn Met
865                 870                 875                 880

Ser Arg Leu Ala Arg Gln Arg Leu Leu Gly Arg Ser Trp Ser Val Pro
                885                 890                 895

Val Ile Arg His Leu Phe Ala Pro Leu Lys Glu Tyr Phe Ala Cys Val
            900                 905                 910

<210> SEQ ID NO 8
<211> LENGTH: 853
<212> TYPE: PRT
<213> ORGANISM: Homo sapiens

<400> SEQUENCE: 8

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
                20                  25                  30

Asp Ser Pro Pro Ile Leu Glu Ala Ile Arg Thr Pro Glu Ile Arg Gly
            35                  40                  45

Arg Arg Ser Ser Ser Arg Leu Ser Lys Arg Glu Val Ser Ser Leu Leu
        50                  55                  60

Ser Tyr Thr Gln Asp Leu Thr Gly Asp Gly Asp Gly Glu Asp Gly Asp
65                  70                  75                  80

Gly Ser Asp Thr Pro Val Met Pro Lys Leu Phe Arg Glu Thr Arg Thr
                85                  90                  95

Arg Ser Glu Ser Pro Ala Val Arg Thr Arg Asn Asn Asn Ser Val Ser
            100                 105                 110

Ser Arg Glu Arg His Arg Pro Ser Pro Arg Ser Thr Arg Gly Arg Gln
        115                 120                 125

Gly Arg Asn His Val Asp Glu Ser Pro Val Glu Phe Pro Ala Thr Arg
    130                 135                 140

Ser Leu Arg Arg Arg Ala Thr Ala Ser Ala Gly Thr Pro Trp Pro Ser
```

```
                145                 150                 155                 160
        Pro Pro Ser Ser Tyr Leu Thr Ile Asp Leu Thr Asp Asp Thr Glu Asp
                        165                 170                 175
        Thr His Gly Thr Pro Gln Ser Ser Thr Pro Tyr Ala Arg Leu Ala
                    180                 185                 190
        Gln Asp Ser Gln Gln Gly Gly Met Glu Ser Pro Gln Val Glu Ala Asp
                    195                 200                 205
        Ser Gly Asp Gly Asp Ser Ser Glu Tyr Gln Asp Gly Lys Glu Phe Gly
            210                 215                 220
        Ile Gly Asp Leu Val Trp Gly Lys Ile Lys Gly Phe Ser Trp Trp Pro
        225                 230                 235                 240
        Ala Met Val Val Ser Trp Lys Ala Thr Ser Lys Arg Gln Ala Met Ser
                        245                 250                 255
        Gly Met Arg Trp Val Gln Trp Phe Gly Asp Gly Lys Phe Ser Glu Val
                    260                 265                 270
        Ser Ala Asp Lys Leu Val Ala Leu Gly Leu Phe Ser Gln His Phe Asn
                    275                 280                 285
        Leu Ala Thr Phe Asn Lys Leu Val Ser Tyr Arg Lys Ala Met Tyr His
            290                 295                 300
        Ala Leu Glu Lys Ala Arg Val Arg Ala Gly Lys Thr Phe Pro Ser Ser
        305                 310                 315                 320
        Pro Gly Asp Ser Leu Glu Asp Gln Leu Lys Pro Met Leu Glu Trp Ala
                    325                 330                 335
        His Gly Gly Phe Lys Pro Thr Gly Ile Glu Gly Leu Lys Pro Asn Asn
                    340                 345                 350
        Thr Gln Pro Val Val Asn Lys Ser Lys Val Arg Arg Ala Gly Ser Arg
                    355                 360                 365
        Lys Leu Glu Ser Arg Lys Tyr Glu Asn Lys Thr Arg Arg Thr Ala
            370                 375                 380
        Asp Asp Ser Ala Thr Ser Asp Tyr Cys Pro Ala Pro Lys Arg Leu Lys
        385                 390                 395                 400
        Thr Asn Cys Tyr Asn Asn Gly Lys Asp Arg Gly Asp Glu Asp Gln Ser
                        405                 410                 415
        Arg Glu Gln Met Ala Ser Asp Val Ala Asn Asn Lys Ser Ser Leu Glu
                    420                 425                 430
        Asp Gly Cys Leu Ser Cys Gly Arg Lys Asn Pro Val Ser Phe His Pro
                    435                 440                 445
        Leu Phe Glu Gly Gly Leu Cys Gln Thr Cys Arg Asp Arg Phe Leu Glu
            450                 455                 460
        Leu Phe Tyr Met Tyr Asp Asp Asp Gly Tyr Gln Ser Tyr Cys Thr Val
        465                 470                 475                 480
        Cys Cys Glu Gly Arg Glu Leu Leu Cys Ser Asn Thr Ser Cys Cys
                        485                 490                 495
        Arg Cys Phe Cys Val Glu Cys Leu Glu Val Leu Val Gly Thr Gly
                    500                 505                 510
        Ala Ala Glu Ala Lys Leu Gln Glu Pro Trp Ser Cys Tyr Met Cys Leu
                    515                 520                 525
        Pro Gln Arg Cys His Gly Val Leu Arg Arg Lys Asp Trp Asn Val
                    530                 535                 540
        Arg Leu Gln Ala Phe Phe Thr Ser Asp Thr Gly Leu Glu Tyr Glu Ala
        545                 550                 555                 560
        Pro Lys Leu Tyr Pro Ala Ile Pro Ala Ala Arg Arg Pro Ile Arg
                    565                 570                 575
```

Val Leu Ser Leu Phe Asp Gly Ile Ala Thr Gly Tyr Leu Val Leu Lys
            580                 585                 590

Glu Leu Gly Ile Lys Val Gly Lys Tyr Val Ala Ser Glu Val Cys Glu
            595                 600                 605

Glu Ser Ile Ala Val Gly Thr Val Lys His Glu Gly Asn Ile Lys Tyr
            610                 615                 620

Val Asn Asp Val Arg Asn Ile Thr Lys Lys Asn Ile Glu Glu Trp Gly
625                 630                 635                 640

Pro Phe Asp Leu Val Ile Gly Gly Ser Pro Cys Asn Asp Leu Ser Asn
            645                 650                 655

Val Asn Pro Ala Arg Lys Gly Leu Tyr Glu Gly Thr Gly Arg Leu Phe
            660                 665                 670

Phe Glu Phe Tyr His Leu Leu Asn Tyr Ser Arg Pro Lys Glu Gly Asp
            675                 680                 685

Asp Arg Pro Phe Phe Trp Met Phe Glu Asn Val Ala Met Lys Val
            690                 695                 700

Gly Asp Lys Arg Asp Ile Ser Arg Phe Leu Glu Cys Asn Pro Val Met
705                 710                 715                 720

Ile Asp Ala Ile Lys Val Ser Ala Ala His Arg Ala Arg Tyr Phe Trp
            725                 730                 735

Gly Asn Leu Pro Gly Met Asn Arg Pro Val Ile Ala Ser Lys Asn Asp
            740                 745                 750

Lys Leu Glu Leu Gln Asp Cys Leu Glu Tyr Asn Arg Ile Ala Lys Leu
            755                 760                 765

Lys Lys Val Gln Thr Ile Thr Thr Lys Ser Asn Ser Ile Lys Gln Gly
            770                 775                 780

Lys Asn Gln Leu Phe Pro Val Val Met Asn Gly Lys Glu Asp Val Leu
785                 790                 795                 800

Trp Cys Thr Glu Leu Glu Arg Ile Phe Gly Phe Pro Val His Tyr Thr
            805                 810                 815

Asp Val Ser Asn Met Gly Arg Gly Ala Arg Gln Lys Leu Leu Gly Arg
            820                 825                 830

Ser Trp Ser Val Pro Val Ile Arg His Leu Phe Ala Pro Leu Lys Asp
            835                 840                 845

Tyr Phe Ala Cys Glu
    850

<210> SEQ ID NO 9
<211> LENGTH: 393
<212> TYPE: DNA
<213> ORGANISM: Mus musculus

<400> SEQUENCE: 9
tttctacagt atttcaggtg cctaccacac aggaaacctt gaagaaaacc agtttctaga      60
agccgctgtt acctcttgtt tacagtttat atatatatga tagatatgag atatatatat     120
ataaaaggta ctgttaacta ctgtacatcc cgacttcata atggtgcttt caaaacagcg     180
agatgagcaa agacatcagc ttccgcctgg ccctcgtgtg caaatggcgt tcatgccca      240
tggatggtgt agaggggagc agctggaggg ggtttcacaa actgaaggat gacccatatc     300
acccccacc cctgccccat gcctagcttc acctgccaaa aaggggctca gctgaggtgg     360
tcggaccctg gggaagctga gtgtggaatt tat                                 393

<210> SEQ ID NO 10

<211> LENGTH: 424
<212> TYPE: DNA
<213> ORGANISM: Mus musculus

<400> SEQUENCE: 10

```
gaagaaaacc agtttctaga agccgctgtt acctcttgtt tacagtttat atatatatga    60
tagatatgag atatatatat ataaaaggta ctgttaacta ctgtacatcc cgacttcata   120
atggtgcttt caaacagcg agatgagcaa agacatcagc ttccgcctgg ccctctgtgc    180
aaagggtttc agcccaggat ggtgagaggg gagcatctgg aggggttttt aacaaactga   240
aggatgaccc atatcacccc ccaccccctgc cccatgccta gcttcacctg ccaaaaaggg  300
gctcagctga ggtggtcgga ccctggggaa gctgagtgtg gaatttatcc agactcgcgt   360
gcaataacct tagaatatga atctaaaatg actgcctcag aaaatggct tgagaaaaca    420
ttgt                                                                424
```

<210> SEQ ID NO 11
<211> LENGTH: 461
<212> TYPE: DNA
<213> ORGANISM: Mus musculus

<400> SEQUENCE: 11

```
tttaaagcaa accacagagg aggaaaacgc cggaggcttg gccttgcaaa agggttggac    60
atcatctcct gagttttcaa tgttaacctt cagtcctatc taaaaagcaa aataggcccc   120
tccccttcgt tcccctccgg tcctaggagg cgaactttt gttttctact ctttttcaga    180
ggggttttct gtttgtttgg gttttttgttt cttgctgtga ctgaaacaag agagttattg   240
cagcaaaatc agtaacaaca aaagtagaaa atgccttgga gcggaaaggg agagagggaa   300
aattctataa aaacttaaaa tattggtttt ttttttttc cttttctata tatctctttg    360
gttgtctcta gcctgatcag ataggagcac aaacaggaag agaatagaga ccctcggagg   420
cagagtctcc tctcccaccc cccgagcagt ctcaacagca c                       461
```

<210> SEQ ID NO 12
<211> LENGTH: 465
<212> TYPE: DNA
<213> ORGANISM: Mus musculus

<400> SEQUENCE: 12

```
tcagaggggt ttctgtttg tttgggtttt tgtttcttgc tgtgactgaa acaagagagt     60
tattgcagca aaatcagtaa caacaaaaag tagaaatgcc ttggagagga agggagaga   120
gggaaaattc tataaaaact taaaatattg gttttttttt ttttccttt tctatatatc    180
tctttggttg tctctagcct gatcagatag gagcacaaac aggaagagaa tagagaccct   240
cggaggcaga gtctcctctc ccacccccg agcagtctca acagcaccat tcctggtcat    300
gcaaaacaga acccaactag cagcaggcg ctgagagaac accacaccag acactttct    360
acagtatttc aggtgcctac cacacaggaa accttgaaga aaaccagttt ctagaagccg   420
ctgttacctc ttgtttacag tttatatata tatgatagat atgag                   465
```

<210> SEQ ID NO 13
<211> LENGTH: 393
<212> TYPE: DNA
<213> ORGANISM: Mus musculus

<400> SEQUENCE: 13

```
aaaacgccgg aggcctttgc cttgcacaag ggttggacat catctcctga gttttcaatg    60
```

```
ttaaccttca gtcctatcta aaaagcaaaa taggcccctc cccttcttcc cctccggtcc    120
taggaggcga acttttttgtt ttctactctt tttcagaggg gttttctgtt tgtttgggtt    180
tttgtttctt gctgtgactg aaacaagaga gttattgcag caaatcagt aacaacaaaa     240 agtagaaatg ccttggagag gaaagggaga gagggaaaat tctataaaaa cttaaaatat    300 tggtttttt tttttttcctt ttctatatat cgctttggtt gtctctagcc tgatcagata    360
ggagcacaaa caggaagaga atagagaccc tcg                                393

<210> SEQ ID NO 14
<211> LENGTH: 309
<212> TYPE: DNA
<213> ORGANISM: Mus musculus

<400> SEQUENCE: 14
gtgatgattg acgccaaaga agtgtctgct gcacacaggg cccgttactt ctaggggtaa    60
ccttcctggc atgaacaggc ctttggatcc actgtgaatg ataagctgga gctgcaagag   120
tgtctggagc acggcagaat agccaagttc agcaaagtga ggaccattac caccaggtca   180
aactctataa agcagggcaa agaccagcat ttccccgtct tcatgaacga aaggaggac    240 atcctgtggt gcactgaaat ggaaagggtc tttggcttcc ccgtccacta cacagacgtc   300
tccaacatg                                                          309

<210> SEQ ID NO 15
<211> LENGTH: 341
<212> TYPE: DNA
<213> ORGANISM: Mus musculus

<400> SEQUENCE: 15
tgttaacctt cagtcctatc taaaaagcaa aataggcccc tccccttctt ccctccggt    60 cctaggaggc gaacttttg ttttctactc ttttcagag gggttttctg tttgtttggg    120
tttttgtttc ttgctgtgac tgaaacaaga gagttattgc agcaaaatca gtaacaacaa   180
aaagtagaaa tgccttggag aggaaaggga gagagggaaa attctataaa aacttaaaat   240
attggttttt tttttttttcc ttttctatat atctctttgg ttgtctctag cctgatcaga   300
taggagcaca acaggaagaa gaatagagac cctcggaggc a                      341

<210> SEQ ID NO 16
<211> LENGTH: 240
<212> TYPE: DNA
<213> ORGANISM: Mus musculus
<220> FEATURE:
<221> NAME/KEY: Unsure
<222> LOCATION: (32)..(32)
<223> OTHER INFORMATION: May be any nucleic acid

<400> SEQUENCE: 16 acatttttgta tgttttttta tttgctccag gnggggttaa tggcgggtca ctttccctca    60
ctctggaata tttctgatcc cacaagggc cttcaacgtg gctgacgaat tcaaaatcag    120
ggacaatgtt ttctcaagcc attttttctga ggcagtcatt ttagattcat attctaaggt   180
tattgcacgc gagtctggat aaattccaca ctcagcttcc ccagggtccg accacctcag   240

<210> SEQ ID NO 17
<211> LENGTH: 256
<212> TYPE: DNA
<213> ORGANISM: Mus musculus
<220> FEATURE:
```

```
<221> NAME/KEY: Unsure
<222> LOCATION: (75)..(75)
<223> OTHER INFORMATION: May be any nucleic acid

<400> SEQUENCE: 17
atcagcttcc gcctggccct ctgtgcaaag ggtttcagcc caggatgggg agagggagc     60 agctggaggg ggttntaaca aactgaagga tgacccatat cacccccccac ccctgcccca    120 tgcctagctt cacctgccaa aaagggctc agctgaggtg gtcggaccct ggggaagctg    180
agtgtggaat ttatccagac tcgcgtgcaa taaccttaga atatgaatct aaaatgactg    240
cctcagaaaa atggct                                                    256

<210> SEQ ID NO 18
<211> LENGTH: 435
<212> TYPE: DNA
<213> ORGANISM: Mus musculus

<400> SEQUENCE: 18
gtggaagccc atgcaatgat ctctctaacg tcaatcctgc ccgcaaaggt ttatatgagg     60
gcacaggaag gctcttcttc gagttttacc acttgctgaa ttatacccgc cccaaggagg    120
gcgacaaccg tccattcttc tggatgttcg agaatgttgt ggccatgaaa gtgaatgaca    180
agaaagacat ctcaagattc ctggcatgta acccagtgat gatcgatgcc atcaaggtgt    240
ctgctgctca cagggcccgg tacttctggg gtaacctacc cggaatgaac aggcccgtga    300
tggcttcaaa gaatgataag ctcgagctgc aggactgcct ggagttcagt aggacagcaa    360
agttaaagaa agtgcagaca ataaccacca agtcgaactc catcagacag ggcaaaaacc    420
agcttttccc tgtag                                                     435

<210> SEQ ID NO 19
<211> LENGTH: 522
<212> TYPE: DNA
<213> ORGANISM: Mus musculus

<400> SEQUENCE: 19
gatgatgtca gcagggatga catcaccacc tttagggctt ttccctggca ggggcccatg     60
tggctagtcc tcacgaagac tggagtagaa tgtttggagc tcaggaaggg tgggtggagt    120
ggagtctctt ccaggtgtga gggatacgaa ggaggaagct tagggaaatc cattccccac    180
tccctcttgc caaatgaggg gcccagtccc caacagctca ggtccccaga accccctagt    240
tcctcatgag aagctaggac cagaagcaca tcgttcccct tatctgagca gtgtttgggg    300
aactacagtg aaaaccttct ggagatgtta aaagcttttt accccacgat agattgtgtt    360 tttaagggt gctttttta ggggcatcac tggagataag aaagctgcat ttcagaaatg    420
ccatcgtaat ggttttaaa cacctttac ctaattacag gtgctatttt atagaagcag    480
acaacacttc tttttatgac tctcagactt ctattttcat gt                       522

<210> SEQ ID NO 20
<211> LENGTH: 348
<212> TYPE: DNA
<213> ORGANISM: Mus musculus

<400> SEQUENCE: 20
aaaggaggcc cattagagtc ctgtctctgt tgatggaat tgcaacgggg tacttggtgc     60
tcaaggagtt gggtattaaa gtggaaaagt acattgcctc cgaagtctgt gcagagtcca    120
tcgctgtggg aactgttaag catgaaggcc agatcaaata tgtcaatgac gtccggaaaa    180
```

```
tcaccaagaa aaatattgaa gagtggggcc cgttcgactt ggtgattggt ggaagcccat    240
gcaatgatct ctctaacgtc aatcctgccc gcaaaggttt atatgagggc acaggaaggc    300
tcttcttcga gttttaccac ttgctgaatt atacccgccc caaggagg                 348

<210> SEQ ID NO 21
<211> LENGTH: 258
<212> TYPE: DNA
<213> ORGANISM: Mus musculus

<400> SEQUENCE: 21
gtttatggtt taagtcttcc tggcaccttc cccttgcttt ggtacaaggg ctgaagtcct     60
gttggtcttg tagcatttcc caggatgatg atgtcagcag ggatgacatc atcaccttta    120
gggcttttcc ctggcagggg cccatgtggc tagtcctcac gaagactgga gtagaatgtt   180
tggagctcag gaagggtggg tggagtgtgc ctcttccagg tgtgagggat acgaaggagg   240
aagcttaggg aaatccat                                                 258

<210> SEQ ID NO 22
<211> LENGTH: 334
<212> TYPE: DNA
<213> ORGANISM: Mus musculus

<400> SEQUENCE: 22
tggggtaacc tacccggaat gaacagttaa agaaagtgca gacaataacc accaagtcga     60
actccatcag acagggcaaa aaccagcttt tccctgtagt catgaatggc aaggacgacg    120
ttttgtggtg cactgagctc gaaggatct tcggcttccc tgctcactac acggacgtgt    180
ccaacatggg ccgcggcgcc cgtcagaagc tgctgggcag gtcctggagt gtaccggtca   240
tcagacacct gtttgccccc ttgaaggact actttgcctg tgaatagttc tacccaggac   300
tggggagctc tcggtcagag ccagtgccca gagt                               334

<210> SEQ ID NO 23
<211> LENGTH: 299
<212> TYPE: DNA
<213> ORGANISM: Mus musculus
<220> FEATURE:
<221> NAME/KEY: Unsure
<222> LOCATION: (59)..(59)
<223> OTHER INFORMATION: May be any nucleic acid
<221> NAME/KEY: Unsure
<222> LOCATION: (173)..(173)
<223> OTHER INFORMATION: May be any nucleic acid

<400> SEQUENCE: 23 ctgttttgt ttgttttttt ggtatcttag ccatcacttc tgagtgataa actcaggang      60
gtaaaagaaa gccatcttac tacctacttc aagttttaaa gtttcagggt aagagaacat    120
gagcaccatg ccgggctact ctaagcagcc aggtctgagc tgtgcacacg ganggagcac   180
cggggctccc ctgcaaggcc aggaggctct gctcccactg agcaggagaa agctgaggta   240
cagtgatgtg aggccccaca caggtgagct aaaaagggga caggtgaggt gccttcagg    299

<210> SEQ ID NO 24
<211> LENGTH: 455
<212> TYPE: DNA
<213> ORGANISM: Mus musculus

<400> SEQUENCE: 24
gatcgcttcc tagagctctt ctacatgtat gatgaggacg gctatcagtc ctactgcacc     60
```

```
gtgtctgtga gggccgtgaa ctgctgctgt gcagtaacac aagctgctgc agatgcttct    120
gtgtggagtg tctggaggtg ctggtgggcg caggacagct gaggatgcca agctgcagga    180
accctggagc tgctatatgt gcctccctca gcgctgccat ggggtcctcc gacgcaggaa    240
agattggaac atgcgcctgc aagacttctt cactactgat cctgacctgg aagaatttca    300
ggagccaccc aagttgtacc cagcaattcc tgcagccaaa aggaggccca ttagagtcct    360
gtctctgttt gatggaattg caacggggta cttggtgctc aaggagttgg gtattaaagt    420
ggaaaagtac attgcctccg aagtctgtgc agagt                                455

<210> SEQ ID NO 25
<211> LENGTH: 368
<212> TYPE: DNA
<213> ORGANISM: Homo sapiens
<220> FEATURE:
<221> NAME/KEY: Unsure
<222> LOCATION: (307)..(307)
<223> OTHER INFORMATION: May be any nucleic acid
<221> NAME/KEY: Unsure
<222> LOCATION: (335)..(335)
<223> OTHER INFORMATION: May be any nucleic acid
<221> NAME/KEY: Unsure
<222> LOCATION: (353)..(353)
<223> OTHER INFORMATION: May be any nucleic acid
<221> NAME/KEY: Unsure
<222> LOCATION: (360)..(360)
<223> OTHER INFORMATION: May be any nucleic acid

<400> SEQUENCE: 25
acgttttgta tgttttttta tttgctccag gtggggtttt gactgtcact ttcccacact    60
ctggattagt tctgatccca ccacaaggag ccctcgaatt ggctaaagtg agaaactggg    120
cctgaagact ccgtaccctc tgccatcttg ccagggagt ctccttttag aaaacaatca    180
aagggttatt gcatgagtct ggatgaatcc cactctcagc ttgtccacgg gcccgaccac    240
ctcatctagc cccctttttg gcaagggaga acctggctcc caagttctcc tccttcactt    300
tcgttancaa accaaggggg aagaagccca ccgtngagaa cgcgccatct tgnaaagctn    360
ggtcttcc                                                              368

<210> SEQ ID NO 26
<211> LENGTH: 399
<212> TYPE: DNA
<213> ORGANISM: Homo sapiens
<220> FEATURE:
<221> NAME/KEY: Unsure
<222> LOCATION: (87)..(87)
<223> OTHER INFORMATION: May be any nucleic acid
<221> NAME/KEY: Unsure
<222> LOCATION: (314)..(314)
<223> OTHER INFORMATION: May be any nucleic acid
<221> NAME/KEY: Unsure
<222> LOCATION: (318)..(318)
<223> OTHER INFORMATION: May be any nucleic acid
<221> NAME/KEY: Unsure
<222> LOCATION: (370)..(370)
<223> OTHER INFORMATION: May be any nucleic acid

<400> SEQUENCE: 26
gaacatgagg atggagagaa gtatcagcac ccagaagaga aaaaggaatt taaaacaaaa    60
accacagagg cggaaatacc ggaggcnttt gcttgcgaaa agggttggac atcatctcct    120 gattttcaa tgttattctt cagtcctatt taaaaacaaa accaagctcc cttcccttcc    180
tcccccttcc cttttttttc ggtcagacct tttatttttct actcttttca gaggggtttt    240
```

```
ctgtttgttt gggttttgtt tcttgctgtg actgaaacaa gaaggttatt gcagcaaaaa      300
tcaggtaaca aaanatangt aacaataacct tgcagaggaa aggtgggagg agaggaaaaa     360
agggaaattn ctatagaaat ctatatattg gggttggtt                            399
```

```
<210> SEQ ID NO 27
<211> LENGTH: 318
<212> TYPE: DNA
<213> ORGANISM: Homo sapiens
<220> FEATURE:
<221> NAME/KEY: Unsure
<222> LOCATION: (205)..(205)
<223> OTHER INFORMATION: May be any nucleic acid
<221> NAME/KEY: Unsure
<222> LOCATION: (275)..(275)
<223> OTHER INFORMATION: May be any nucleic acid

<400> SEQUENCE: 27
gtacgaggtg cggcagaagt gccggaacat tgaggacatc tgcatctcct gtgggagcct      60
caatgttacc ctggaacacc ccctcttcgt tggaggaatg tgccaaaact gcaagaactg     120 cttttctggag tgtgcgtacc agtacgacga cgacggctac cagtcctact gcaccatctg    180 ctgtggggc cgtgaggtgc tcatntgcgg aaacaacaac tgctgcaggt gcttttgcgt      240
ggagtgtgtg gacctcttgg tggggccggg ggctncccag gcagcagtta aggaagatca     300
tgtacgtcgg ggacgtcc                                                   318
```

```
<210> SEQ ID NO 28
<211> LENGTH: 259
<212> TYPE: DNA
<213> ORGANISM: Homo sapiens
<220> FEATURE:
<221> NAME/KEY: Unsure
<222> LOCATION: (227)..(227)
<223> OTHER INFORMATION: May be any nucleic acid
<221> NAME/KEY: Unsure
<222> LOCATION: (234)..(234)
<223> OTHER INFORMATION: May be any nucleic acid

<400> SEQUENCE: 28
gagccgagca gctgaaggca cccgctgggt catgtggttc ggagacggca aattctcagt      60
ggtgtgtgtt gagaagctga tgccgctgag ctcgttttgc agtgcgttcc accaggccac     120
gtacaacaag cagcccatgt accgcaaagc catctacgag gtcctgcagg tggccagcag     180
ccgcgcgggg aagctgttcc cggtgtgcca cgacagcgat gagagtnaca ctgncaaggc     240
cgtgggaggt gcagaacaa                                                  259
```

```
<210> SEQ ID NO 29
<211> LENGTH: 483
<212> TYPE: DNA
<213> ORGANISM: Homo sapiens

<400> SEQUENCE: 29
tttttttttt ttgtatgttt ttttatttgc tccaggtggg gttttgactg tcactttccc      60
acactctgga ttagttctga tcccaccaca aggagccctc gaattggcta aagtgagaaa     120
ctgggcctga agactccgta ccctctgcca tcttgccgag ggagtctcct tttagaaaac     180
aatcaaaggg ttattgcatg agtctggatg aatcccactc tcagctgtcc acggggccga     240
ccacctcatc taggccccctt tttggcaagg agaacccggg tcccaagttc tcctccttca    300
cttcgttaca aaccagggggg aaaaagccca cgtgaaaacg cggcatctgc aaaatggttc    360 ccttttcttca tccctgggga aacctttgcg ccaaggcaac gtggaaactg atggttttac    420
```
tcaactcgct gttttgaagc gccattatga atcggggtt gtacgtaggt aaagtcccgt    480
gcc                                                                483

<210> SEQ ID NO 30
<211> LENGTH: 337
<212> TYPE: DNA
<213> ORGANISM: Homo sapiens
<220> FEATURE:
<221> NAME/KEY: Unsure
<222> LOCATION: (41)..(41)
<223> OTHER INFORMATION: May be any nucleic acid
<221> NAME/KEY: Unsure
<222> LOCATION: (45)..(45)
<223> OTHER INFORMATION: May be any nucleic acid
<221> NAME/KEY: Unsure
<222> LOCATION: (176)..(176)
<223> OTHER INFORMATION: May be any nucleic acid
<221> NAME/KEY: Unsure
<222> LOCATION: (190)..(190)
<223> OTHER INFORMATION: May be any nucleic acid
<221> NAME/KEY: Unsure
<222> LOCATION: (207)..(207)
<223> OTHER INFORMATION: May be any nucleic acid
<221> NAME/KEY: Unsure
<222> LOCATION: (265)..(265)
<223> OTHER INFORMATION: May be any nucleic acid
<221> NAME/KEY: Unsure
<222> LOCATION: (290)..(290)
<223> OTHER INFORMATION: May be any nucleic acid
<221> NAME/KEY: Unsure
<222> LOCATION: (317)..(317)
<223> OTHER INFORMATION: May be any nucleic acid
<221> NAME/KEY: Unsure
<222> LOCATION: (322)..(322)
<223> OTHER INFORMATION: May be any nucleic acid

<400> SEQUENCE: 30
gggcattcag gtggaccgct acattgcctc ggaggtgtgt naggnctcca tcacggtggg    60
catggtgcgg caccagggga agatcatgta cgtcggggac gtccgcagcg tcacacagaa   120
gcatatccag gagtgggggcc cattcgatct ggtgattggg ggcagtccct gcaatnacct   180
ctccatcgtn aaccctgctc gcaaggncct ctacgagggc actggccggc tcttctttaa   240
gttctaccgc ctcctgcatg atgcncggcc caaggagggg agatgatcgn cccttcttct   300
ggctctttaa gaatgtngtg gnccatgggc gtttagt                            337

<210> SEQ ID NO 31
<211> LENGTH: 271
<212> TYPE: DNA
<213> ORGANISM: Homo sapiens
<220> FEATURE:
<221> NAME/KEY: Unsure
<222> LOCATION: (234)..(234)
<223> OTHER INFORMATION: May be any nucleic acid

<400> SEQUENCE: 31
cttgtttaca gtttatatat atatgataga tatgagatat atatataaaa ggtactgtta    60
actactgtac aacccgactt cataatggtg ctttcaaaca gcgagatgag taaaaacatc   120
agcttccacg ttgccttctg cgcaaagggt ttcaccaagg atggagaaag ggagacagct   180
tgcagatggc gcgttctcac ggtgggctct tccccttggt ttgtaacgaa gtgnaggagg   240
agaacttggg agccaggttc tccctgccaa a                                  271

<210> SEQ ID NO 32
<211> LENGTH: 430
<212> TYPE: DNA

<213> ORGANISM: Homo sapiens

<400> SEQUENCE: 32

```
acgttttgta tgttttttta tttgctccag gtggggtttt gactgtcact ttcccacact      60
ctggattagt tctgatccca ccacaaggag ccctcgaatt ggctaaagtg agaaactggg     120
cctgaagact ccgtaccctc tgccatcttg ccgagggagt ctcctttaga aacaatcaa     180
agggttattg catgagtctg gatgaatccc actctcagct gtccacgggc ccgaccacct     240
catctagccc ccttttggc agggagaacc tggctcccaa gttctcctcc ttcacttcgt     300
tacaaaccaa ggggaagagc ccaccgtgag aacgcgccat ctgcaagctg tctccctttc     360
tccatccttg gtgaaacccc tttgcgcaga aggcaacgtg gaagctgatg ttttactca      420
tctcgctgtt                                                            430
```

<210> SEQ ID NO 33
<211> LENGTH: 483
<212> TYPE: DNA
<213> ORGANISM: Homo sapiens

<400> SEQUENCE: 33

```
tttttttttt ttgtatgttt tttatttgc tccaggtggg gttttgactg tcactttccc      60
acactctgga ttagttctga tcccaccaca aggagccctc gaattggcta agtgagaaa     120
ctgggcctga agactccgta ccctctgcca tcttgccgag ggagtctcct tttagaaaac     180
aatcaaaggg ttattgcatg agtctggatg aatcccactc tcagctgtcc acggggccga     240
ccacctcatc taggcccctt tttggcaagg agaacccggg tcccaagttc tcctccttca     300
cttcgttaca aaccaggggg aaaaagccca cgtgaaaacg cggcatctgc aaaatggttc     360
cctttcttca tccctgggga aacctttgcg ccaaggcaac gtggaaactg atggttttac     420
tcaactcgct gttttgaagc gccattatga aatcggggtt gtacgtaggt aaagtcccgt     480
gcc                                                                   483
```

<210> SEQ ID NO 34
<211> LENGTH: 411
<212> TYPE: DNA
<213> ORGANISM: Homo sapiens

<400> SEQUENCE: 34

```
ttttttttta cgttttgtat gttttttat ttgctccagg tggggttttg actgtcactt      60
tcccacactc tggattagtt ctgatcccac cacaaggagc cctcgaattg gctaaagtga     120
gaaactgggc ctgaagactc cgtaccctct gccatcttgc cgagggagtc tcctttaga     180
aaacaatcaa agggttattg catgagtctg gatgaatccc actctcagct gtccacgggc     240
ccgaccacct catctagccc ccttttggca gggagaacct ggctcccaag ttctcctcct     300
tcacttcgtt acaaaccaag gggaagagcc caccgtgaga acgcgccatc tgcaagctgt     360
ctccctttct ccatccttgg tgaaacccctt tgcgcagaag gcaacgtgga a             411
```

<210> SEQ ID NO 35
<211> LENGTH: 530
<212> TYPE: DNA
<213> ORGANISM: Homo sapiens

<400> SEQUENCE: 35

```
cgcctggacg agcccagact gctgggccgg tcatggagcg cgccagtcat ccgccacctc      60
ttcgctccgc tgaaggcgta ttttgcgtgt gtctaaggga catgggggca aactgaggta     120
```

```
gcgacacaaa gttaaacaca caaacacccc acacacaaca taatacaaca ccaagaacat    180
gaggatggag agaagtatca gccacccaga agagaacaag gaatttaaaa ccaaaaccac    240
agaggcggaa ataccggagg actttgcctt gcgaccaggg ttggacatca tctcctgatt    300
tttcaatgtt attcttcagt cctatttaaa aacaaaacca agctcccttc ccttcctgcg    360
gcttcccttt ttttcggtc agacctttta ttttctactc ttttcagagg ggttttctgt    420
ttgtttgggt tttgtttctt gctgtgactg aaacaagaag gttattgcag caaaaatcag    480
taacaaaaaa tagtaacaat accttgcaga ggaaaggtgg gagagaggaa               530
```

<210> SEQ ID NO 36
<211> LENGTH: 535
<212> TYPE: DNA
<213> ORGANISM: Homo sapiens

<400> SEQUENCE: 36

```
tttacgtttt gtatgttttt ttatttgctc caggtggggt tttgactgtc actttcccac     60
actctggatt agttctgatc ccaccacaag gagccctcga attggctaaa gtgagaaact    120
gggcctgaag actccgtacc ctctgccatc ttgccgaggg agtctccttt tagaaaacaa    180
tcaaagggtt attgcatgag tctggatgaa tcccactctc agctgtccac gggcccgacc    240
acctcatcta gcccccttt tggcagggag aacctggctc ccaagttctc ctccttcact     300
tcgttacaaa ccacggggaa gagcccaccg tgagaacgcg ccatctgcaa gctgtctccc    360
tttctccatc cttggtgaaa cccttttgcgc agaaggcaac gtggaagctg atgttttttac  420 tcatctcgct gtttgaaagc accattatga agtcgggttg tacagtagtt aacagtacct    480
tttatatata tatctcatat ctatcatata tatataaact gtaaacaaga ggtaa          535
```

<210> SEQ ID NO 37
<211> LENGTH: 428
<212> TYPE: DNA
<213> ORGANISM: Homo sapiens
<220> FEATURE:
<221> NAME/KEY: Unsure
<222> LOCATION: (12)..(12)
<223> OTHER INFORMATION: May be any nucleic acid
<221> NAME/KEY: Unsure
<222> LOCATION: (15)..(15)
<223> OTHER INFORMATION: May be any nucleic acid
<221> NAME/KEY: Unsure
<222> LOCATION: (415)..(415)
<223> OTHER INFORMATION: May be any nucleic acid
<221> NAME/KEY: Unsure
<222> LOCATION: (424)..(424)
<223> OTHER INFORMATION: May be any nucleic acid

<400> SEQUENCE: 37

```
acgttttgta tntantttta tttgctccag gtggggtttt gactgtcact ttcccacact     60
ctggattagt tctgatccca ccacaaggag ccctcgaatt ggctaaagtg agaaactggg    120
cctgaagact ccgtaccctc tgccatcttg ccagggagt ctccttttag aaaacaatca     180
aagggttatt gcatgagtct ggatgaatcc cactctcagc tgtccacggg cccgaccacc    240
tcatctagcc ccctttttgg cagggagaac ctgggctccc aagttctcct ccttcacttc    300
gttacaaacc aaggggaagg agcccaccgt gagaacggcg ccatcttgca agctgtctcc    360
ctttctccat ccttgggtga aaccctttg cgcagaaggg caacgtggga agctngatgt     420 tttntaac                                                             428
```

<210> SEQ ID NO 38
<211> LENGTH: 419
<212> TYPE: DNA
<213> ORGANISM: Homo sapiens
<220> FEATURE:
<221> NAME/KEY: Unsure
<222> LOCATION: (306)..(306)
<223> OTHER INFORMATION: May be any nucleic acid
<221> NAME/KEY: Unsure
<222> LOCATION: (325)..(325)
<223> OTHER INFORMATION: May be any nucleic acid
<221> NAME/KEY: Unsure
<222> LOCATION: (341)..(341)
<223> OTHER INFORMATION: May be any nucleic acid
<221> NAME/KEY: Unsure
<222> LOCATION: (367)..(367)
<223> OTHER INFORMATION: May be any nucleic acid
<221> NAME/KEY: Unsure
<222> LOCATION: (385)..(385)
<223> OTHER INFORMATION: May be any nucleic acid

<400> SEQUENCE: 38
atgggcgtta gtgacaagag ggacatctcg cgatttctcg agtccaaccc tgtgatgatt      60
gatgccaaag aagtgtcagc tgcacacagg gcccgctact tctggggtaa ccttcccggt     120
atgaacaggc cgttggatcc actgtgaatg ataagctgga gctgcaggag tgtctggagc     180
atggcaggat agccaagttc agcaaagtga ggaccattac tacgaggtca aactccataa     240
agcagggcaa agaccagcat tttcctgtct tcatgaatga gaaagaggac atcttatggt     300
gcactnaaat tggaaagggt atttngggtt tcccagtcca ntatactgac gtctccaaca     360
tgagccnctt tgggagggca gagantgctg gggccggttc atgggagcgt gcccagttc     419

<210> SEQ ID NO 39
<211> LENGTH: 437
<212> TYPE: DNA
<213> ORGANISM: Homo sapiens
<220> FEATURE:
<221> NAME/KEY: Unsure
<222> LOCATION: (2)..(2)
<223> OTHER INFORMATION: May be any nucleic acid
<221> NAME/KEY: Unsure
<222> LOCATION: (11)..(11)
<223> OTHER INFORMATION: May be any nucleic acid
<221> NAME/KEY: Unsure
<222> LOCATION: (23)..(23)
<223> OTHER INFORMATION: May be any nucleic acid
<221> NAME/KEY: Unsure
<222> LOCATION: (76)..(76)
<223> OTHER INFORMATION: May be any nucleic acid
<221> NAME/KEY: Unsure
<222> LOCATION: (224)..(224)
<223> OTHER INFORMATION: May be any nucleic acid
<221> NAME/KEY: Unsure
<222> LOCATION: (290)..(290)
<223> OTHER INFORMATION: May be any nucleic acid
<221> NAME/KEY: Unsure
<222> LOCATION: (362)..(362)
<223> OTHER INFORMATION: May be any nucleic acid
<221> NAME/KEY: Unsure
<222> LOCATION: (376)..(376)
<223> OTHER INFORMATION: May be any nucleic acid
<221> NAME/KEY: Unsure
<222> LOCATION: (386)..(386)
<223> OTHER INFORMATION: May be any nucleic acid
<221> NAME/KEY: Unsure
<222> LOCATION: (426)..(426)
<223> OTHER INFORMATION: May be any nucleic acid

<400> SEQUENCE: 39
tnttttgttg nctctagcct gancagatag gagcacaagc aggggacgga aagagagaga      60
cactcaggcg gcacanttcc ctcccagcca ctgagctgtc gtgccagcac cattcctggt     120

```
cacgcaaaac agaacccagt tagcagcagg gagacgagaa caccacacaa gacattttc    180 tacagtattt caggtgccta ccacacagga aaccttgaag aaantcagtt tctaggaagc    240
cgctgttacc tcttgtttac agtttatata tatatgatag atatgagatn tatatataaa    300
aggtactgtt aactactgta caacccgact tcataatggg tgctttcaaa caggcgaggt    360
gngtaaaaac atcagnttcc acgttngcct tttgcgcaaa gggtttcacc aggttgggga    420
aagggngaca gctttttt                                                  437

<210> SEQ ID NO 40
<211> LENGTH: 385
<212> TYPE: DNA
<213> ORGANISM: Homo sapiens
<220> FEATURE:
<221> NAME/KEY: Unsure
<222> LOCATION: (340)..(340)
<223> OTHER INFORMATION: May be any nucleic acid
<221> NAME/KEY: Unsure
<222> LOCATION: (365)..(365)
<223> OTHER INFORMATION: May be any nucleic acid
<221> NAME/KEY: Unsure
<222> LOCATION: (376)..(376)
<223> OTHER INFORMATION: May be any nucleic acid

<400> SEQUENCE: 40
tacgttttgt atgttttttt atttgctcca ggtgggtttt tgactgtcac tttcccacac     60
tctggattag ttctgatccc accacaagga gccctcgaat tggctaaagt gagaaactgg    120
gcctgaagac tccgtaccct ctgccatctt gccgagggag tctccttta gaaaacaatc     180 aaagggttat tgcatgagtc tggatgaatc ccactctcag ctgtccacgg gcccgaccac    240
ctcatctagc ccccttttg gcagggagaa cctgggctcc caagttctcc tccttcactt    300
cgttacaaac caaggggaag agcccaccgt gagaacgcgn catctgcaag ctgtctccct    360
ttttncatcc ttggtngaaa ccctt                                          385

<210> SEQ ID NO 41
<211> LENGTH: 294
<212> TYPE: DNA
<213> ORGANISM: Homo sapiens
<220> FEATURE:
<221> NAME/KEY: Unsure
<222> LOCATION: (66)..(66)
<223> OTHER INFORMATION: May be any nucleic acid
<221> NAME/KEY: Unsure
<222> LOCATION: (73)..(73)
<223> OTHER INFORMATION: May be any nucleic acid
<221> NAME/KEY: Unsure
<222> LOCATION: (267)..(267)
<223> OTHER INFORMATION: May be any nucleic acid

<400> SEQUENCE: 41
aaaggtggga gagggaaaa aaggaaattc tatagaaatc tatatattgg gttgtttttt      60
tttttntttt ttnttttttt tttttgggt ttttttttt tactatatat ctttttttg      120 ttgtctctag cctgatcaga taggagcaca agcaggggac ggaaagagag agacactcag    180
gcggcacatt tgccctccca gccactgagc tgtcgtgcca gcaccattcc tgggtcacgc    240
aaaacagaac ccagttagca gcagggnaga cgagaacacc acacaagaca tttt          294

<210> SEQ ID NO 42
<211> LENGTH: 610
<212> TYPE: DNA
<213> ORGANISM: Homo sapiens
<220> FEATURE:
```

```
<221> NAME/KEY: Unsure
<222> LOCATION: (576)..(576)
<223> OTHER INFORMATION: May be any nucleic acid
<221> NAME/KEY: Unsure
<222> LOCATION: (590)..(590)
<223> OTHER INFORMATION: May be any nucleic acid

<400> SEQUENCE: 42
tacgttttgt atgtttttt atttgctcca ggtggggttt tgactgtcac tttcccacac    60
tctggattag ttctgatccc accacaagga gccctcgaat tggctaaagt gagaaactgg   120
gcctgaagac tccgtaccct ctgccatctt gccgagggag tctcctttta gaaaacaatc   180
aaagggttat tgcatgagtc tggatgaatc ccactctcag ctgtccacgg gcccgaccac   240
ctcatctagc cccctttttg cagggagaa cctggctccc aagttctcct ccttcacttc    300
gttacaaacc aaggggaaga gcccaccgtg agaacgcgcc atctgcaagc tgtctccctt   360
tctccatcct ttggtggaaa cccttttgcg cagaaggcaa cgtggaagct gatgttttta   420
ctcatctcgc tgtttgaaag caccattatg aagtcgggtt gtacagtagt taacagtacc   480
ttttatatat atatctcata tctatcatat atatataaac tggtaaacaa gaggtaacag   540
cgggcttcta gaaactgatt ttcttcaagg tttccngtgt ggtaggcacn tgaaatactg   600
gtagaaaatg                                                          610

<210> SEQ ID NO 43
<211> LENGTH: 283
<212> TYPE: DNA
<213> ORGANISM: Homo sapiens
<220> FEATURE:
<221> NAME/KEY: Unsure
<222> LOCATION: (72)..(72)
<223> OTHER INFORMATION: May be any nucleic acid
<221> NAME/KEY: Unsure
<222> LOCATION: (272)..(272)
<223> OTHER INFORMATION: May be any nucleic acid

<400> SEQUENCE: 43
taactttgtg tcgctacctc agtttgcccc catgtcccctt acacacacgc aaaatactcc   60
ttcagcggag anacgaggtg gcggatgact ggcacgctcc atgaccggcc cagcagtctc   120
tgcctcgcca gcggctcat gttggagacg tcagtatagt ggactgggaa accaaatacc    180
ctttccattt cagtgcacca taagatgtcc tctttctcat tcatgaagac aggaaaaatg   240
ctggtctttg gcctgcttta tggagttttg anctcgtaag taa                     283

<210> SEQ ID NO 44
<211> LENGTH: 383
<212> TYPE: DNA
<213> ORGANISM: Homo sapiens

<400> SEQUENCE: 44
gcggggacgt ccgcagcgtc acacagaagc atatccagga gtggggccca ttcgatctgg    60
tgattggggg cagtccctgc aatgacctct ccatcgtcaa ccctgctcgc aagggcctct   120
acagggcac tggccggctc ttctttgagt tctaccgcct cctgcatgat gcgcggccca    180
aggagggaga tgatcgcccc ttctctggct ctttgagaat tggtggcca tggcgttagt     240
acacagagag gacacatctc gcgatttctc gagtccaacc ctgtatatga ttgatgccaa   300
agaagtctca tctgcacaga ggcccctcta cttctgggt cacctcccg tattaacagg    360
ccgtaggatc cactgttatt ata                                          383
```

```
<210> SEQ ID NO 45
<211> LENGTH: 447
<212> TYPE: DNA
<213> ORGANISM: Homo sapiens
<220> FEATURE:
<221> NAME/KEY: Unsure
<222> LOCATION: (445)..(445)
<223> OTHER INFORMATION: May be any nucleic acid

<400> SEQUENCE: 45
acgttttgta tgttttttta tttgctccag gtggggtttt gactgtcact ttcccacact      60
ctggattagt tctgatccca ccacaaggag ccctcgaatt ggctaaagtg agaaactggg     120
cctgaagact ccgtacgctc tgccatcttg ccgagggagt ctccttttag aaaacaatca     180
aagggttatt gcatgagtct ggatgaatcc cactctcagc tgtccacggg cccgaccacc     240
tcatctaagc ccccttttg gcagggagaa cctggctccc aagttctcct ccttcacttc      300
gttacaaacc aagggaaga gcccaccgtg agaacgcgcc atctgcaagc tgtctccctt      360
tctccatcct tggtgaaacc tttgcgcaga aggcaacgtg gaaagctgaa ggttttact      420 catctcgctg tttgaaaagc accanta                                         447

<210> SEQ ID NO 46
<211> LENGTH: 100
<212> TYPE: DNA
<213> ORGANISM: Homo sapiens
<220> FEATURE:
<221> NAME/KEY: Unsure
<222> LOCATION: (96)..(96)
<223> OTHER INFORMATION: May be any nucleic acid

<400> SEQUENCE: 46
acaccaagaa catgagggat ggagagaagt atcagcaccc agaagagaaa aaggaattta      60
aaacaaaaac cacagaggcg gaaataccgg tgactnttct                           100

<210> SEQ ID NO 47
<211> LENGTH: 150
<212> TYPE: DNA
<213> ORGANISM: Homo sapiens

<400> SEQUENCE: 47
tactccttca gcgggtagga ggtggcggat gactggcacg ctccatgacc ggcccagcag      60
tctctgcctc gccaagcgct catgttggag aggtcagtat agtggactgg gaaaccaaat     120 acccttttcca tttcagtgca ccataagatg                                     150

<210> SEQ ID NO 48
<211> LENGTH: 237
<212> TYPE: DNA
<213> ORGANISM: Homo sapiens
<220> FEATURE:
<221> NAME/KEY: Unsure
<222> LOCATION: (7)..(7)
<223> OTHER INFORMATION: May be any nucleic acid
<221> NAME/KEY: Unsure
<222> LOCATION: (42)..(42)
<223> OTHER INFORMATION: May be any nucleic acid
<221> NAME/KEY: Unsure
<222> LOCATION: (45)..(45)
<223> OTHER INFORMATION: May be any nucleic acid

<400> SEQUENCE: 48
gctgtcncag gggtgtgtgg gtctaggagc ctggctggag gncancgctg ggtgggagct      60
tgggacaccg atgggcctgc atctgacctg ttgtgctcac tgcttaggac cctccaaagg     120
```

| | |
|---|---|
| tttacccacc tgtcccagct gagaagagga agcccatccg ggtgctgtct ctctttgatg | 180 |
| gaatcgctac aggtgagggg tgcaggccca agaggtgctg gcctcgtgcg aattcct | 237 |

<210> SEQ ID NO 49
<211> LENGTH: 442
<212> TYPE: DNA
<213> ORGANISM: Homo sapiens
<220> FEATURE:
<221> NAME/KEY: Unsure
<222> LOCATION: (19)..(19)
<223> OTHER INFORMATION: May be any nucleic acid
<221> NAME/KEY: Unsure
<222> LOCATION: (91)..(91)
<223> OTHER INFORMATION: May be any nucleic acid
<221> NAME/KEY: Unsure
<222> LOCATION: (137)..(137)
<223> OTHER INFORMATION: May be any nucleic acid
<221> NAME/KEY: Unsure
<222> LOCATION: (388)..(388)
<223> OTHER INFORMATION: May be any nucleic acid
<221> NAME/KEY: Unsure
<222> LOCATION: (397)..(397)
<223> OTHER INFORMATION: May be any nucleic acid
<221> NAME/KEY: Unsure
<222> LOCATION: (428)..(428)
<223> OTHER INFORMATION: May be any nucleic acid

<400> SEQUENCE: 49

| | |
|---|---|
| tttttttacta tatatcttnt ttttgttgtc tctagcctga tcagatagga gcacaagcag | 60 |
| gggacggaaa gagagagaca ctcaggcggc natttccctc ccagccactg agctgtcgtg | 120 |
| ccagcaccat tcctggncac gcaaaacaga acccagttag cagcagggag acgagaacac | 180 |
| cacacaagac attttctac agtatttcag gtgcctacca cacaggaaac cttgaagaaa | 240 |
| atcagtttct aggaagccgc tgttacctct tgtttacagt ttatatatat atggatagga | 300 |
| tatgaggata tatatataaa agggtactgt ttaactactg taccaacccg actttcataa | 360 |
| tgggtgcttt tcaaacagcc gaggatgngg ttaaaancat cagcttccac gttgccttct | 420 |
| gcggcaangg gtttcaccag gg | 442 |

<210> SEQ ID NO 50
<211> LENGTH: 395
<212> TYPE: DNA
<213> ORGANISM: Homo sapiens
<220> FEATURE:
<221> NAME/KEY: Unsure
<222> LOCATION: (343)..(343)
<223> OTHER INFORMATION: May be any nucleic acid
<221> NAME/KEY: Unsure
<222> LOCATION: (372)..(372)
<223> OTHER INFORMATION: May be any nucleic acid
<221> NAME/KEY: Unsure
<222> LOCATION: (379)..(379)
<223> OTHER INFORMATION: May be any nucleic acid
<221> NAME/KEY: Unsure
<222> LOCATION: (384)..(384)
<223> OTHER INFORMATION: May be any nucleic acid

<400> SEQUENCE: 50

| | |
|---|---|
| tacgttttgt atgttttttt atttgctcca ggtggggttt tgactgtcac tttcccacac | 60 |
| tctggattag ttctgatccc accacaagga gccctcgaat tggctaaagt gagaaactgg | 120 |
| gcctgaagac tccgtaccct ctgccatctt gccgagggag tctccttta gaaaacaatc | 180 |
| aaagggttat tgcatgagtc tggatgaatc ccactctcag ctgtccacgg gcccgaccac | 240 |
| ctcatctagc cccctttttg ggcagggaga aacctgggct cccaagttct cctccttcac | 300 |
| ttcgttaaca aaccaagggg aagagcccac cgtgaggaac ggngccatct ggcaaggttg | 360 | ttctcccttt tnttccatnc cttnggtgaa aaccc                              395

<210> SEQ ID NO 51
<211> LENGTH: 835
<212> TYPE: DNA
<213> ORGANISM: Homo sapiens
<220> FEATURE:
<221> NAME/KEY: Unsure
<222> LOCATION: (2)..(9)
<223> OTHER INFORMATION: May be any nucleic acid
<221> NAME/KEY: Unsure
<222> LOCATION: (11)..(16)
<223> OTHER INFORMATION: May be any nucleic acid
<221> NAME/KEY: Unsure
<222> LOCATION: (19)..(21)
<223> OTHER INFORMATION: May be any nucleic acid
<221> NAME/KEY: Unsure
<222> LOCATION: (32)..(32)
<223> OTHER INFORMATION: May be any nucleic acid
<221> NAME/KEY: Unsure
<222> LOCATION: (37)..(37)
<223> OTHER INFORMATION: May be any nucleic acid
<221> NAME/KEY: Unsure
<222> LOCATION: (46)..(46)
<223> OTHER INFORMATION: May be any nucleic acid
<221> NAME/KEY: Unsure
<222> LOCATION: (48)..(49)
<223> OTHER INFORMATION: May be any nucleic acid
<221> NAME/KEY: Unsure
<222> LOCATION: (62)..(63)
<223> OTHER INFORMATION: May be any nucleic acid
<221> NAME/KEY: Unsure
<222> LOCATION: (75)..(76)
<223> OTHER INFORMATION: May be any nucleic acid
<221> NAME/KEY: Unsure
<222> LOCATION: (120)..(120)
<223> OTHER INFORMATION: May be any nucleic acid
<221> NAME/KEY: Unsure
<222> LOCATION: (140)..(140)
<223> OTHER INFORMATION: May be any nucleic acid
<221> NAME/KEY: Unsure
<222> LOCATION: (146)..(146)
<223> OTHER INFORMATION: May be any nucleic acid
<221> NAME/KEY: Unsure
<222> LOCATION: (199)..(199)
<223> OTHER INFORMATION: May be any nucleic acid
<221> NAME/KEY: Unsure
<222> LOCATION: (300)..(300)
<223> OTHER INFORMATION: May be any nucleic acid
<221> NAME/KEY: Unsure
<222> LOCATION: (365)..(365)
<223> OTHER INFORMATION: May be any nucleic acid
<221> NAME/KEY: Unsure
<222> LOCATION: (388)..(388)
<223> OTHER INFORMATION: May be any nucleic acid
<221> NAME/KEY: Unsure
<222> LOCATION: (397)..(397)
<223> OTHER INFORMATION: May be any nucleic acid
<221> NAME/KEY: Unsure
<222> LOCATION: (403)..(403)
<223> OTHER INFORMATION: May be any nucleic acid
<221> NAME/KEY: Unsure
<222> LOCATION: (421)..(421)
<223> OTHER INFORMATION: May be any nucleic acid
<221> NAME/KEY: Unsure
<222> LOCATION: (441)..(441)
<223> OTHER INFORMATION: May be any nucleic acid
<221> NAME/KEY: Unsure
<222> LOCATION: (461)..(461)
<223> OTHER INFORMATION: May be any nucleic acid
<221> NAME/KEY: Unsure
<222> LOCATION: (475)..(475)
<223> OTHER INFORMATION: May be any nucleic acid
<221> NAME/KEY: Unsure
<222> LOCATION: (494)..(494)
<223> OTHER INFORMATION: May be any nucleic acid
<221> NAME/KEY: Unsure -continued

```
<222> LOCATION: (514)..(514)
<223> OTHER INFORMATION: May be any nucleic acid
<221> NAME/KEY: Unsure
<222> LOCATION: (536)..(537)
<223> OTHER INFORMATION: May be any nucleic acid
<221> NAME/KEY: Unsure
<222> LOCATION: (545)..(545)
<223> OTHER INFORMATION: May be any nucleic acid
<221> NAME/KEY: Unsure
<222> LOCATION: (550)..(550)
<223> OTHER INFORMATION: May be any nucleic acid
<221> NAME/KEY: Unsure
<222> LOCATION: (554)..(554)
<223> OTHER INFORMATION: May be any nucleic acid
<221> NAME/KEY: Unsure
<222> LOCATION: (562)..(562)
<223> OTHER INFORMATION: May be any nucleic acid
<221> NAME/KEY: Unsure
<222> LOCATION: (565)..(565)
<223> OTHER INFORMATION: May be any nucleic acid
<221> NAME/KEY: Unsure
<222> LOCATION: (569)..(569)
<223> OTHER INFORMATION: May be any nucleic acid
<221> NAME/KEY: Unsure
<222> LOCATION: (580)..(580)
<223> OTHER INFORMATION: May be any nucleic acid
<221> NAME/KEY: Unsure
<222> LOCATION: (584)..(584)
<223> OTHER INFORMATION: May be any nucleic acid
<221> NAME/KEY: Unsure
<222> LOCATION: (587)..(587)
<223> OTHER INFORMATION: May be any nucleic acid
<221> NAME/KEY: Unsure
<222> LOCATION: (595)..(595)
<223> OTHER INFORMATION: May be any nucleic acid
<221> NAME/KEY: Unsure
<222> LOCATION: (599)..(599)
<223> OTHER INFORMATION: May be any nucleic acid
<221> NAME/KEY: Unsure
<222> LOCATION: (617)..(617)
<223> OTHER INFORMATION: May be any nucleic acid
<221> NAME/KEY: Unsure
<222> LOCATION: (629)..(629)
<223> OTHER INFORMATION: May be any nucleic acid
<221> NAME/KEY: Unsure
<222> LOCATION: (639)..(639)
<223> OTHER INFORMATION: May be any nucleic acid
<221> NAME/KEY: Unsure
<222> LOCATION: (658)..(658)
<223> OTHER INFORMATION: May be any nucleic acid
<221> NAME/KEY: Unsure
<222> LOCATION: (660)..(660)
<223> OTHER INFORMATION: May be any nucleic acid
<221> NAME/KEY: Unsure
<222> LOCATION: (663)..(663)
<223> OTHER INFORMATION: May be any nucleic acid
<221> NAME/KEY: Unsure
<222> LOCATION: (695)..(696)
<223> OTHER INFORMATION: May be any nucleic acid
<221> NAME/KEY: Unsure
<222> LOCATION: (699)..(701)
<223> OTHER INFORMATION: May be any nucleic acid
<221> NAME/KEY: Unsure
<222> LOCATION: (706)..(706)
<223> OTHER INFORMATION: May be any nucleic acid
<221> NAME/KEY: Unsure
<222> LOCATION: (710)..(710)
<223> OTHER INFORMATION: May be any nucleic acid
<221> NAME/KEY: Unsure
<222> LOCATION: (716)..(719)
<223> OTHER INFORMATION: May be any nucleic acid
<221> NAME/KEY: Unsure
<222> LOCATION: (727)..(727)
<223> OTHER INFORMATION: May be any nucleic acid
<221> NAME/KEY: Unsure
<222> LOCATION: (731)..(731)
<223> OTHER INFORMATION: May be any nucleic acid
<221> NAME/KEY: Unsure
<222> LOCATION: (735)..(737)
```

<223> OTHER INFORMATION: May be any nucleic acid
<221> NAME/KEY: Unsure
<222> LOCATION: (739)..(739)
<223> OTHER INFORMATION: May be any nucleic acid
<221> NAME/KEY: Unsure
<222> LOCATION: (743)..(745)
<223> OTHER INFORMATION: May be any nucleic acid
<221> NAME/KEY: Unsure
<222> LOCATION: (754)..(755)
<223> OTHER INFORMATION: May be any nucleic acid
<221> NAME/KEY: Unsure
<222> LOCATION: (781)..(781)
<223> OTHER INFORMATION: May be any nucleic acid
<221> NAME/KEY: Unsure
<222> LOCATION: (787)..(787)
<223> OTHER INFORMATION: May be any nucleic acid
<221> NAME/KEY: Unsure
<222> LOCATION: (790)..(790)
<223> OTHER INFORMATION: May be any nucleic acid
<221> NAME/KEY: Unsure
<222> LOCATION: (800)..(801)
<223> OTHER INFORMATION: May be any nucleic acid
<221> NAME/KEY: Unsure
<222> LOCATION: (805)..(805)
<223> OTHER INFORMATION: May be any nucleic acid
<221> NAME/KEY: Unsure
<222> LOCATION: (809)..(809)
<223> OTHER INFORMATION: May be any nucleic acid
<221> NAME/KEY: Unsure
<222> LOCATION: (820)..(820)
<223> OTHER INFORMATION: May be any nucleic acid
<221> NAME/KEY: Unsure
<222> LOCATION: (827)..(830)
<223> OTHER INFORMATION: May be any nucleic acid
<221> NAME/KEY: Unsure
<222> LOCATION: (832)..(832)
<223> OTHER INFORMATION: May be any nucleic acid

<400> SEQUENCE: 51

```
cnnnnnnnng nnnnnnttnn nctgccttta tnctcgntgc cgatantnnt atccatcatc      60
annttcttgg tgttnnatta tgttttgtgt tttttgtttg tttgtttaac tttgtgtcgn     120
tacctcagtt tgcccccatn tccctnacac acacgcaaaa tactccttca gcggagcgaa     180
gaggtggcgg atgactggna cgctccatga ccggcccagc agtctctgcc tcgccaagcg     240
gatcatgttg gagacgtcag tatagtggac tgggaaacca ataccccttt ccatttcagn     300
gcaccataag atgtcctctt tctcattcat gaagacaggg aaaatgctgg tctttggcct     360
gctcnatgga gtttgactcc gtagtaaggg ccctcanttt ggntgacttg ggctatcctg     420
ncatgctcca gacacttccg nagggtcaca acagaagcat nttccagggg gtggnggcca     480
ttccgacctt tggnggattg gggggaagc cccnaaaaat aaccccttca aacggnnaaa     540
ccctngttcn gaangggccc cnttncgang ggaaactggn ccgnttnttt ctttngggnt     600
tcctccccc cccccnaaa ataatgggng gcccaagna ggggaattac ccccccncn       660
ttnttttttt tttggaaatt tggggccccg ggggnnaann naaaanggcn acttcnnnnt     720
ttttggnccc ncccnnnant ttnnnccccaa aaannttaat taaaaaggcc cttttctggg     780
nccccnttn aaccgccccn ngatnggtnc ttggttcccn aacacannnn cncaa           835
```

<210> SEQ ID NO 52
<211> LENGTH: 479
<212> TYPE: DNA
<213> ORGANISM: Homo sapiens
<220> FEATURE:
<221> NAME/KEY: Unsure
<222> LOCATION: (364)..(364)
<223> OTHER INFORMATION: May be any nucleic acid
<221> NAME/KEY: Unsure
<222> LOCATION: (416)..(416)

<223> OTHER INFORMATION: May be any nucleic acid
<221> NAME/KEY: Unsure
<222> LOCATION: (464)..(464)
<223> OTHER INFORMATION: May be any nucleic acid

<400> SEQUENCE: 52

```
tacgttttgt atgtttttt atttgctcca ggtggggttt tgactgtcac tttcccacac      60
tctggattag ttctgatccc accacaagga gccctcgaat tggctaaagt gagaaactgg    120
gcctgaagac tccgtaccct ctgccatctt gccgagggag tctccttta gaaaacaatc    180
aaagggttat tgcatgagtc tggatgaatc ccactctcag ctgtccacgg gcccgaccac    240
ctcatctagc ccccttttg gcagggagaa cctggctccc aagttctcct ccttcacttc    300
gttacaaacc aaggggaaga gcccaccatg agaacgcgcc atctgcaagc tgtctccctt    360
tctncatcct tggtgaaacc tttgcgcaga aggcaacgtg gaagctgatg tttttntcat    420
ctcgctgttt gaaagcacca ttatgaagtc gggttgtaca gtantaacag tacttttag    479
```

<210> SEQ ID NO 53
<211> LENGTH: 521
<212> TYPE: DNA
<213> ORGANISM: Homo sapiens
<220> FEATURE:
<221> NAME/KEY: Unsure
<222> LOCATION: (327)..(327)
<223> OTHER INFORMATION: May be any nucleic acid
<221> NAME/KEY: Unsure
<222> LOCATION: (507)..(507)
<223> OTHER INFORMATION: May be any nucleic acid

<400> SEQUENCE: 53

```
agaacaccac acaagacatt tttctacagt atttcaggtg cctaccacac aggaaacctt     60
gaagaaaatc agtttctaga agccgctgtt acctcttgtt tacagtttat atatatatga   120
tagatatgag atatatatat aaaaggtact gttaactact gtacaacccg acttcataat   180
ggtgctttca aacagcgaga tgagtaaaaa catcagcttc cacgttgcct tctgcgcaaa   240
gggtttcacc aaggatggag aaagggagac agcttgcaga tggcgcgttc tcatggtggg   300
ctcttcccct tggtttgtaa cgaagtntag gaggagaact tgggagccag gttctccctg   360
ccaaaaaggg ggctagatga ggtggtcggg cccgtggaca gctgagagtg ggattcatcc   420
agactcatgc aataaccctt tgattgtttc taaaaggaga ctccctcggc aagatggcag   480
agggtacgga gtcttcaggc ccagttntca ctttagccaa t                       521
```

<210> SEQ ID NO 54
<211> LENGTH: 440
<212> TYPE: DNA
<213> ORGANISM: Homo sapiens

<400> SEQUENCE: 54

```
ctctctttga tggaatcgct acagggctcc tggtgctgaa ggacttgggc attcaggtgg     60
accgctacat tgcctcggag gtgtgtgagg actccatcac ggtgggcatg gtgcggcacc    120
aggggaagat catgtacgtc ggggacgtcc gcagcgtcac acagaagcat atccaggagt    180
ggggcccatt cgatctggtg attggggca gtccctgcaa tgacctctcc atcgtcaacc    240
ctgctcgcaa gggcctctac gagggcactg gccggctctt ctttgagttc taccgcctcc    300
tgcatgatgc gcggcccaag gagggagatg atcgcccctt cttctggctc tttgagaatg    360
tggtggccat gggcgtttag tgacaagagg gacatctcgc gatttctcga gtccaaccct    420
gtgatgattg atgccaaaga                                              440
```

<210> SEQ ID NO 55
<211> LENGTH: 273
<212> TYPE: DNA
<213> ORGANISM: Homo sapiens

<400> SEQUENCE: 55

| | | | | | |
|---|---|---|---|---|---|
| acgttttgta | tgttttttta | tttgctccag | gtggggtttt | gactgtcact | ttcccacact | 60 |
| ctggattagt | tctgatccca | ccacaaggag | ccctcgaatt | ggctaaagtg | agaaactggg | 120 |
| cctgaagact | ccgtaccctc | tgccatcttg | ccgagggagt | ctcctttag | aaaacaatca | 180 |
| aagggttatt | gcatgagtct | ggatgaatcc | cactctcagc | tgtccacggg | cccgaccacc | 240 |
| tcatctagcc | ccctttttgg | cagggagaac | ctg | | | 273 |

<210> SEQ ID NO 56
<211> LENGTH: 190
<212> TYPE: DNA
<213> ORGANISM: Homo sapiens
<220> FEATURE:
<221> NAME/KEY: Unsure
<222> LOCATION: (39)..(39)
<223> OTHER INFORMATION: May be any nucleic acid
<221> NAME/KEY: Unsure
<222> LOCATION: (83)..(83)
<223> OTHER INFORMATION: May be any nucleic acid
<221> NAME/KEY: Unsure
<222> LOCATION: (181)..(181)
<223> OTHER INFORMATION: May be any nucleic acid

<400> SEQUENCE: 56

| | | | | | |
|---|---|---|---|---|---|
| aaaaacacaa | aacataataa | aacaccaaga | acatgaggnt | ggagagaagt | atcagcaccc | 60 |
| agaagagaaa | aaggaattta | aancaaaaac | cacagaggcg | gaaataccgg | agggctttgc | 120 |
| cttgcgaaaa | gggttggaca | tcatctcctg | attttcaat | gttattcttc | agtcctattt | 180 |
| naaaacaaag | | | | | | 190 |

<210> SEQ ID NO 57
<211> LENGTH: 445
<212> TYPE: DNA
<213> ORGANISM: Homo sapiens
<220> FEATURE:
<221> NAME/KEY: Unsure
<222> LOCATION: (167)..(167)
<223> OTHER INFORMATION: May be any nucleic acid
<221> NAME/KEY: Unsure
<222> LOCATION: (353)..(353)
<223> OTHER INFORMATION: May be any nucleic acid

<400> SEQUENCE: 57

| | | | | | |
|---|---|---|---|---|---|
| ttagacaaat | actgattta | attaaacata | aggtaaactc | taggcatccg | tcatctttca | 60 |
| gcctaaaaat | tagcaaaaac | tgttgaaaca | aggcacagtt | tttccccat | atttgttacg | 120 |
| tcgtggctcc | agttacaaaa | aaattttaat | gaaaacgtta | aacatanaaa | tagaagtttg | 180 |
| agatttaaa | aagtgtataa | aaagccccac | aaaacttgtc | aacggttgtt | ccttattcta | 240 |
| caaaatagca | ccagtaagaa | gagtaaaagg | tgttaaaaac | catttatgac | agcatttctg | 300 |
| aaatgcagct | tgtctgaatt | cccggttctc | cctaaaaacg | acttctttat | ggnattaaaa | 360 |
| aagggtttaa | aaaaatctcc | aaaggggagc | accgagcttt | gcaggttttc | cctgtcatct | 420 |
| ctcagatgtg | ggggaagctc | gtggc | | | | 445 |

<210> SEQ ID NO 58
<211> LENGTH: 287

```
<212> TYPE: DNA
<213> ORGANISM: Homo sapiens
<220> FEATURE:
<221> NAME/KEY: Unsure
<222> LOCATION: (38)..(38)
<223> OTHER INFORMATION: May be any nucleic acid
<221> NAME/KEY: Unsure
<222> LOCATION: (171)..(171)
<223> OTHER INFORMATION: May be any nucleic acid
<221> NAME/KEY: Unsure
<222> LOCATION: (204)..(204)
<223> OTHER INFORMATION: May be any nucleic acid
<221> NAME/KEY: Unsure
<222> LOCATION: (274)..(274)
<223> OTHER INFORMATION: May be any nucleic acid

<400> SEQUENCE: 58
ttccccacat ctgagagatg acagggaaaa ctgcaaanct cggtgctccc tttggagatt      60
ttttaatcct tttttattcc ataagaagtc gttttagggg agaacgggaa ttcagacaag     120
ctgcatttca gaaatgctgt cataatggtt tttaacacct tttactcctc nttactggtg    180
ctatttttgt agaataaggg aacnacgttg acaagttttg gtggggggcct ttttatacac   240 cttttttaaa atctccaact tcctaatttt taanggttta accgttt                 287

<210> SEQ ID NO 59
<211> LENGTH: 535
<212> TYPE: DNA
<213> ORGANISM: Homo sapiens
<220> FEATURE:
<221> NAME/KEY: Unsure
<222> LOCATION: (452)..(452)
<223> OTHER INFORMATION: May be any nucleic acid
<221> NAME/KEY: Unsure
<222> LOCATION: (526)..(526)
<223> OTHER INFORMATION: May be any nucleic acid

<400> SEQUENCE: 59
tagacaaata ctgattttaa ttaaacataa ggtaaactct aggcatccgt catctttcag      60
cctaaaaatt agcaaaaact gttgaaacaa ggcacagttt ttccccata tttgttacgt     120 cgtggctcca gttacaaaaa aatttaatg aaaacgttaa acataaaat agaagtttga      180 gattttaaaa agtgtataaa aagccccaca aaacttgtca acgttgttcc ttattctaca    240
aaatagcacc agtaagaaga gtaaaaggtg ttaaaaacca ttatgacagc atttctgaaa    300
tgcagcttgt ctgaattccc gttctcccta aaaacgactt cttatggaat aaaaaaggat    360
taaaaaatct ccaaagggag caccgagctt tgcagttttc cctgtccgtc tctcagatgt    420
ggggaaggta tgagaaatgt atgtctgtcc cngactgctg tcactgcctc tgagttagta    480
aaaggtgaga atgagggtag cagcttccca tctggggcct gtgccngtgg agggt         535

<210> SEQ ID NO 60
<211> LENGTH: 449
<212> TYPE: DNA
<213> ORGANISM: Homo sapiens
<220> FEATURE:
<221> NAME/KEY: Unsure
<222> LOCATION: (7)..(7)
<223> OTHER INFORMATION: May be any nucleic acid
<221> NAME/KEY: Unsure
<222> LOCATION: (200)..(200)
<223> OTHER INFORMATION: May be any nucleic acid

<400> SEQUENCE: 60
atcgcancag gctacctagt cctcaaagag ttgggcataa aggtaggaaa gtacgtcgct      60
tctgaagtgt gtgaggagtc cattgctgtt ggaaccgtga agcacgaggg gaatatcaaa    120
```

-continued

```
tacgtgaacg acgtgaggaa catcacaaag aaaaatattg aagaatgggg cccatttgac      180
ttggtgattg gcggaaccan tgcaacgatc tctcaaatgt gaatccagcc aggaaaggcc      240
tgtatgaggg tacaggccgg ctcttcttcg aattttacca cctgctgaat tactcacgcc      300
ccaaggaggg tgatgaccgg ccgttcttct ggatgtttga gaatgttgta gccatgaagg      360
ttggcgacaa gagggacatc tcacggttcc tggagtgtaa tccagtgatg attgatgcca      420
tccaaagttt ctgctgctca cagggcccg                                        449
```

<210> SEQ ID NO 61
<211> LENGTH: 522
<212> TYPE: DNA
<213> ORGANISM: Homo sapiens
<220> FEATURE:
<221> NAME/KEY: Unsure
<222> LOCATION: (146)..(146)
<223> OTHER INFORMATION: May be any nucleic acid
<221> NAME/KEY: Unsure
<222> LOCATION: (281)..(281)
<223> OTHER INFORMATION: May be any nucleic acid
<221> NAME/KEY: Unsure
<222> LOCATION: (304)..(304)
<223> OTHER INFORMATION: May be any nucleic acid

<400> SEQUENCE: 61

```
aagagggaca tctcacggtt cctggagtgt aatccagtga tgattgatgc catcaaagtt       60
tctgctgctc acagggcccg atacttctgg ggcaacctac ccgggatgaa caggcccgtg      120
atagcatcaa agaatgataa actcgngctg caggactgct tggaatacaa taggatagcc      180
aagttaaaga agtacagac aataaccacc aagtcgaact cgatcaaaca ggggaaaaac      240
caacttttcc ctgttgtcat gaatggcaaa gaagatgttt ngtggtgcac tgagctcgaa      300
aggntctttg gctttcctgt gcactacaca gacgtgtcca acatgggccg tggtgcccgc      360
cagaagctgc tgggaaggtc ctggagcgtg cctgtcatcc gacacctctt cgcccctctg      420
aaggactact ttgcatgtga atagttccag ccagggccca agcccactgg ggtgtgtggc      480
agagcaggac ccaggaggtg tgattctgaa ggcatcccca gg                         522
```

<210> SEQ ID NO 62
<211> LENGTH: 573
<212> TYPE: DNA
<213> ORGANISM: Homo sapiens

<400> SEQUENCE: 62

```
ctaagatcca ttttctaaac tccaattgag cattctctgt atctgggtgg tttttacttt       60
tttacttaat cttgcttgat caggaactct ggtgtcttct tggccccca cgtgatctcg       120 ttcatggtca ctttttttgtt tatctcattt tctctgaggc tggtccttcc tgttaacgtc      180
ttggcatttg tgggaagcac aaaatgttct tgtccctcca actctgcttt tcgctccctg      240
ccctgccatt cctctcccgc gcctgccctc tcccttccat ctttcccagg tacttttctc      300
tcccagccct gccactcttc tgccgcacct gcgctctccc ctccatcttt cccaggtact      360
tttgagcctt gactccccag gtcccttcat tctgtgctca ctccatgatg tcattttgtt      420
ctccagttaa agaaagtaca gacaataacc accaagtcga actcgatcaa acaggggaaa      480
aaccaacttt tccctgttgt catgaatggc aaagaagatg ttttgtggtg cactgagctc      540
gaaaggatct ttggctttcc tgtgcactac aca                                    573
```

<210> SEQ ID NO 63

<211> LENGTH: 559
<212> TYPE: DNA
<213> ORGANISM: Homo sapiens

<400> SEQUENCE: 63

```
agacaaatac tgattttaat taaacataag gtaaactcta ggcatccgtc atctttcagc    60
ctaaaaatta gcaaaaactg ttgaaacaag gcacagtttt ttccccatat ttgttacgtc   120
gtggctccag ttacaaaaaa attttaatga aaacgttaaa cataaaaata gaagtttgag   180
attttaaaaa gtgtataaaa agccccacaa aacttgtcaa cgttgttcct tattctacaa   240
aatagcacca gtaagaagag taaaaggtgt taaaaaccat tatgacagca tttctgaaat   300
gcagcttgtc tgaattcccg ttctccctaa aaacgacttc ttatggaata aaaaaggatt   360
aaaaaatctc caagggagc accgagcttt gcagttttcc ctgtcatcta tcagatgtgg   420
ggaaggtatg agaaatgtat gtctgtccct gactgctgtc actgcctctg agtttagtaa   480
aaagatgaga aatgagggta gcagacttct catctgggga cctgtgcctg tgagggtag    540
gtctcctgga gagggaatg                                                559
```

<210> SEQ ID NO 64
<211> LENGTH: 391
<212> TYPE: DNA
<213> ORGANISM: Homo sapiens

<400> SEQUENCE: 64

```
ttttttttta gacaaatact gattttaatt aacataaggt aaactctag gcatccgtca    60
tctttcagcc taaaaattag caaaaactgt tgaaacaagg cacagttttt tccccatatt   120
tgttacgtcg tggctccagt tacaaaaaaa attttaatga aaacgttaaa cataaaaata   180
gaagtttgag attttaaaaa gtgtataaaa agccccacaa aacttgtcaa cgttgttcct   240
tattctacaa aatagcacca gtaagaagag taaaaggtgt taaaaaccat tatgacagca   300
tttctgaaat gcagcttgtc tgaattcccg ttctccctaa aaacgacttc ttatggaata   360
aaaaaggatt aaaaaatctc caagggagc a                                    391
```

<210> SEQ ID NO 65
<211> LENGTH: 517
<212> TYPE: DNA
<213> ORGANISM: Homo sapiens

<400> SEQUENCE: 65

```
acaaatactg attttaatta aacataaggt aaactctagg caggggcatc tttcagccta    60
aaaattagca aaaactgttg aaacaaggca gttttttc cccatatttg ttacgtcgtg    120
gctccagtta cggaaaaatt ttaatgaaaa cgttaaacat aaaaatagaa gtttgagatt   180
ttaaaaagtg tataaaaagc cccacaaaac ttgtcaacgt tgttccttat tctacaaaat   240
agcaccagta agaagagtaa aaggtgttaa aaaccattat gacagcattt ctgaaatgca   300
gcttgtctga attcccgttc tcctaaaaa cgacttctta tggaataaaa aggattaaa    360
aaatctccaa agggagcacc gagctttgca gttttccctg tcatctctca gatgtgggga   420
aggtatgaga aatgtatgtc tgtccctgac tgctgtcact gcctctgagt ttagtaaaaa   480
gatgagaaat gagggtagca gacttctcat ctgggga                             517
```

<210> SEQ ID NO 66
<211> LENGTH: 442
<212> TYPE: DNA
<213> ORGANISM: Homo sapiens

<400> SEQUENCE: 66

```
gacaaatact gattttaatt aaacataagg taaactctag gcatccgtca tctttcagcc      60
taaaaattag caaaaactgt tgaaacaagg cacagttttt tccccatatt tgttacgtcg     120
tggctccagt tacaaaaaaa attttaatga aaacgttaaa cataaaaata gaagtttgag     180
attttaaaaa gtgtataaaa agccccacaa aacttgtcaa cgttgttcct tattctacaa     240
aatagcacca gtaagaagag taaaaggtgt taaaaaccat tatgacagca tttctgaaat     300
gcagcttgtc tgaattcccg ttctccctaa aaacgacttc ttatgaaata aaaaaggatt     360
aaaaaatctc caagggagc accgagcttt gcagttttcc ctgtcatctc gcagatgtgg     420
ggaaggtatg agaaatgtat gt                                              442
```

<210> SEQ ID NO 67
<211> LENGTH: 396
<212> TYPE: DNA
<213> ORGANISM: Homo sapiens

<400> SEQUENCE: 67

```
gcagtcaggg acagacatac atttctcata ccttccccac atctgagaga tgacagggaa      60
aactgcaaag ctcggtgctc cctttggaga ttttttaatc ctttttttt ccataagaag     120
tcgttttag ggagaacggg aattcagaca agctgcattt cagaaatgct gtcataatgg     180
ttttaacac cttttactct tcttactggt gctattttgt agaataagga acaacgttga     240
caagttttgt ggggcttttt atacactttt taaaatctca aacttctatt tttatgttta     300
acgttttcat taaaattttt ttgtaactgg agccacgacg taacaaatat ggggaaaaaa     360
ctgtgccttg tttcaacagt ttttgctaat ttttag                               396
```

<210> SEQ ID NO 68
<211> LENGTH: 287
<212> TYPE: DNA
<213> ORGANISM: Homo sapiens
<220> FEATURE:
<221> NAME/KEY: Unsure
<222> LOCATION: (7)..(7)
<223> OTHER INFORMATION: May be any nucleic acid
<221> NAME/KEY: Unsure
<222> LOCATION: (169)..(169)
<223> OTHER INFORMATION: May be any nucleic acid

<400> SEQUENCE: 68

```
agacaantac tgattttaat taaacataag gtaaactcta ggcatccgtc atctttcagc      60
ctaaaaatta gcaaaaactg ttgaaacaag gcacagtttt tcccccatat tgttacgtc     120
gtggctccag ttacaaaaaa aattttaatg aaaacgttaa acataaaaant agaagttga     180
gattttaaaa agtgtataaa aagccccaca aaacttgtca acgttgttcc ttattctaca     240
aaatagcacc agtaagaaga gtaaaaggtg ttaaaaacca ttatgac                   287
```

<210> SEQ ID NO 69
<211> LENGTH: 356
<212> TYPE: DNA
<213> ORGANISM: Homo sapiens
<220> FEATURE:
<221> NAME/KEY: Unsure
<222> LOCATION: (193)..(193)
<223> OTHER INFORMATION: May be any nucleic acid

<400> SEQUENCE: 69

```
attgaagaat ggggcccatt tgacttggtg attggcggaa ccgatgcaac gatctctcaa      60
```

```
atgtgaatcc agccaggaaa ggcctgtatg agggtacagg ccggctcttc ttcgaatttt      120
accacctgct gaattactca cgccccaagg agggtgatga ccggccgttc ttctggatgt      180
ttgagaatgt tgnagccatg aaggttggcg acaagaggga catctcacgg ttcctggagt      240
gtaatccagt gatgattgat gccatcaaag tttctgctgc tcacagggcc cgatacttct      300
ggggcaacct acccgggatg aacaggatct tggctttcc tgtgcactac acagac          356
```

<210> SEQ ID NO 70
<211> LENGTH: 408
<212> TYPE: DNA
<213> ORGANISM: Homo sapiens
<220> FEATURE:
<221> NAME/KEY: Unsure
<222> LOCATION: (408)..(408)
<223> OTHER INFORMATION: May be any nucleic acid

<400> SEQUENCE: 70

```
tttagacaaa tactgatttt aattaaacat aaggtaaact ctaggcatcc gtcatctttc       60
agcctaaaaa ttagcaaaaa ctgttgaaac aaggcacagt ttttttcccca tatttgttac     120 gtcgtggctc cagttacaaa aaaaatttta atgaaaacgt taaacataaa aatagaagtt     180 tgagattta aaaagtgtat aaaaagcccc acaaaacttg tcaacgttgt tccttattct      240
acaaaatagc accagtaaga agagtaaaag gtgttaaaaa ccattatgac agcatttctg     300
aaatgcagct tgtctgaatt cccgttctcc ctaaaaacga cttcttatgg aataaaaaag     360
gattaaaaaa tctccaaagg gagcaccgag ctttgcagtt ttccctgn                  408
```

<210> SEQ ID NO 71
<211> LENGTH: 439
<212> TYPE: DNA
<213> ORGANISM: Homo sapiens
<220> FEATURE:
<221> NAME/KEY: Unsure
<222> LOCATION: (50)..(50)
<223> OTHER INFORMATION: May be any nucleic acid
<221> NAME/KEY: Unsure
<222> LOCATION: (85)..(85)
<223> OTHER INFORMATION: May be any nucleic acid
<221> NAME/KEY: Unsure
<222> LOCATION: (405)..(405)
<223> OTHER INFORMATION: May be any nucleic acid

<400> SEQUENCE: 71

```
gcatgtagct acaggacatt tttaagggcc caggatcgtt ttttcccagn tgcaagcaga       60
agagaaaatg ttgtatatgt ctttnacccg gcacattccc cttgcctaaa tacaagggct     120
ggagtctgca cgggacctat tagagtattt tccacaatga tgatgatttc agcagggatg     180
acgtcatcat cacattcagg gctatttttt cccccacaaa cccaagggca ggggccactc     240
ttagctaaat ccctcccccgt gactgcaata gaaccctctg gggagctcag gaaaggggt      300 gtgctgagtt ctataatata agctgccata tattttgtag acaagtatgg ctcctcccat     360
atctccctct tccctaggag aggagtgtga aagcaaggga gcttngataa gacaccccct     420
caaacccatt ccctctcca                                                  439
```

<210> SEQ ID NO 72
<211> LENGTH: 491
<212> TYPE: DNA
<213> ORGANISM: Homo sapiens
<220> FEATURE:
<221> NAME/KEY: Unsure
<222> LOCATION: (26)..(27)

```
<223> OTHER INFORMATION: May be any nucleic acid
<221> NAME/KEY: Unsure
<222> LOCATION: (33)..(33)
<223> OTHER INFORMATION: May be any nucleic acid
<221> NAME/KEY: Unsure
<222> LOCATION: (188)..(188)
<223> OTHER INFORMATION: May be any nucleic acid
<221> NAME/KEY: Unsure
<222> LOCATION: (301)..(301)
<223> OTHER INFORMATION: May be any nucleic acid
<221> NAME/KEY: Unsure
<222> LOCATION: (339)..(339)
<223> OTHER INFORMATION: May be any nucleic acid
<221> NAME/KEY: Unsure
<222> LOCATION: (360)..(360)
<223> OTHER INFORMATION: May be any nucleic acid
<221> NAME/KEY: Unsure
<222> LOCATION: (379)..(379)
<223> OTHER INFORMATION: May be any nucleic acid

<400> SEQUENCE: 72
ttaattaaac ataaggtaaa ctctanngca tcngtcatct ttcagcctaa aaattagcaa      60
aaactgttga acaaggcac  agttttttcc ccatatttgt tacgtcgtgg ctccagttac     120
aaaaaaaatt ttaatgaaaa cgttaaacat aaaaatagaa gtttgagatt ttaaaaagtg    180
tataaaangc cccacaaaac ttgtcaacgt tgttccttat tctacaaaat agcaccagta    240
agaagagtaa aagtgttaa  aaaccattat gacagcattt ctgaaatgca gcttgtctga    300
nttcccgttc tccctaaaaa cgacttctta tgggataana aagggattaa aaaatctccn    360
aaagggaggc accgagcttt gcaggttttc cctggtcatc tctcaggatg tgggggagg    420 gtatggggaa atggtatggt ctggtccctg gactggctgg tcactgcctc tggggttng    480 gtaaaagggt g                                                        491

<210> SEQ ID NO 73
<211> LENGTH: 443
<212> TYPE: DNA
<213> ORGANISM: Homo sapiens
<220> FEATURE:
<221> NAME/KEY: Unsure
<222> LOCATION: (9)..(9)
<223> OTHER INFORMATION: May be any nucleic acid
<221> NAME/KEY: Unsure
<222> LOCATION: (11)..(11)
<223> OTHER INFORMATION: May be any nucleic acid
<221> NAME/KEY: Unsure
<222> LOCATION: (23)..(24)
<223> OTHER INFORMATION: May be any nucleic acid
<221> NAME/KEY: Unsure
<222> LOCATION: (126)..(126)
<223> OTHER INFORMATION: May be any nucleic acid
<221> NAME/KEY: Unsure
<222> LOCATION: (157)..(157)
<223> OTHER INFORMATION: May be any nucleic acid
<221> NAME/KEY: Unsure
<222> LOCATION: (170)..(170)
<223> OTHER INFORMATION: May be any nucleic acid
<221> NAME/KEY: Unsure
<222> LOCATION: (341)..(341)
<223> OTHER INFORMATION: May be any nucleic acid
<221> NAME/KEY: Unsure
<222> LOCATION: (347)..(347)
<223> OTHER INFORMATION: May be any nucleic acid
<221> NAME/KEY: Unsure
<222> LOCATION: (371)..(371)
<223> OTHER INFORMATION: May be any nucleic acid
<221> NAME/KEY: Unsure
<222> LOCATION: (405)..(405)
<223> OTHER INFORMATION: May be any nucleic acid
<221> NAME/KEY: Unsure
<222> LOCATION: (412)..(412)
<223> OTHER INFORMATION: May be any nucleic acid
```

```
<221> NAME/KEY: Unsure
<222> LOCATION: (430)..(430)
<223> OTHER INFORMATION: May be any nucleic acid

<400> SEQUENCE: 73
ttggcggcna ntgcaacgat ctnnaaatgt gaatcagcca ggaaaggctg tatgagggac      60
aggcggctct tcttcgaatt ttccacctgc tgaattactc acgccccaag gagggtgatg     120
accggncgtt cttctggatg tttgagaatg ttgtagncat gaaggttggn gacaagaggg     180
acatctcacg gttcctggag tgtaatccag tgatgattga tgccatcaaa gtttctgctg     240
ctcacagggc ccgatacttc tggggcaacc tacccgggat gaacaggatc tttggctttc     300
ctgtgcacta cacagacgtg tcccaacatg gggccgtggg ngccgcncca ggaagcttgc     360
tggggaaggt nctggggagc gttgccttgt tcatcccgac acctntttcg gnccctattg     420
gaagggattn atttttgcca tgt                                             443

<210> SEQ ID NO 74
<211> LENGTH: 273
<212> TYPE: DNA
<213> ORGANISM: Homo sapiens

<400> SEQUENCE: 74
acgttttgta tgttttttta tttgctccag gtggggtttt gactgtcact ttcccacact      60
ctggattagt tctgatccca ccacaaggag ccctcgaatt ggctaaagtg agaaactggg     120
cctgaagact ccgtacccte tgccatcttg ccgagggagt ctccttttag aaaacaatca     180
aagggttatt gcatgagtct ggatgaatcc cactctcagc tgtccacggg cccgaccacc     240
tcatctagcc ccctttttgg cagggagaac ctg                                  273

<210> SEQ ID NO 75
<211> LENGTH: 250
<212> TYPE: DNA
<213> ORGANISM: Homo sapiens
<220> FEATURE:
<221> NAME/KEY: Unsure
<222> LOCATION: (26)..(27)
<223> OTHER INFORMATION: May be any nucleic acid
<221> NAME/KEY: Unsure
<222> LOCATION: (33)..(33)
<223> OTHER INFORMATION: May be any nucleic acid
<221> NAME/KEY: Unsure
<222> LOCATION: (188)..(188)
<223> OTHER INFORMATION: May be any nucleic acid

<400> SEQUENCE: 75
ttaattaaac ataaggtaaa ctctanngca tcngtcatct ttcagcctaa aaattagcaa      60
aaactgttga aacaaggcac agttttttcc ccatatttgt tacgtcgtgg ctccagttac     120
aaaaaaaatt ttaatgaaaa cgttaaacat aaaaatagaa gtttgagatt ttaaaaagtg     180
tataaaangc cccacaaaac ttgtcaacgt tgttccttat tctacaaaat agcaccagta     240
agaagagtaa                                                            250

<210> SEQ ID NO 76
<211> LENGTH: 443
<212> TYPE: DNA
<213> ORGANISM: Homo sapiens
<220> FEATURE:
<221> NAME/KEY: Unsure
<222> LOCATION: (9)..(9)
<223> OTHER INFORMATION: May be any nucleic acid
<221> NAME/KEY: Unsure
<222> LOCATION: (11)..(11)
```

<223> OTHER INFORMATION: May be any nucleic acid
<221> NAME/KEY: Unsure
<222> LOCATION: (23)..(24)
<223> OTHER INFORMATION: May be any nucleic acid
<221> NAME/KEY: Unsure
<222> LOCATION: (126)..(126)
<223> OTHER INFORMATION: May be any nucleic acid
<221> NAME/KEY: Unsure
<222> LOCATION: (157)..(157)
<223> OTHER INFORMATION: May be any nucleic acid
<221> NAME/KEY: Unsure
<222> LOCATION: (170)..(170)
<223> OTHER INFORMATION: May be any nucleic acid
<221> NAME/KEY: Unsure
<222> LOCATION: (341)..(341)
<223> OTHER INFORMATION: May be any nucleic acid
<221> NAME/KEY: Unsure
<222> LOCATION: (347)..(347)
<223> OTHER INFORMATION: May be any nucleic acid
<221> NAME/KEY: Unsure
<222> LOCATION: (371)..(371)
<223> OTHER INFORMATION: May be any nucleic acid
<221> NAME/KEY: Unsure
<222> LOCATION: (405)..(405)
<223> OTHER INFORMATION: May be any nucleic acid
<221> NAME/KEY: Unsure
<222> LOCATION: (412)..(412)
<223> OTHER INFORMATION: May be any nucleic acid
<221> NAME/KEY: Unsure
<222> LOCATION: (430)..(430)
<223> OTHER INFORMATION: May be any nucleic acid

<400> SEQUENCE: 76

```
ttggcggcna ntgcaacgat ctnnaaatgt gaatcagcca ggaaaggctg tatgagggac      60
aggcggctct tcttcgaatt ttccacctgc tgaattactc acgccccaag gagggtgatg     120
accggncgtt cttctggatg tttgagaatg ttgtagncat gaaggttggn gacaagaggg     180
acatctcacg gttcctggag tgtaatccag tgatgattga tgccatcaaa gtttctgctg     240
ctcacagggc ccgatacttc tggggcaacc tacccgggat gaacaggatc tttggctttc     300
ctgtgcacta cacagacgtg tcccaacatg gggccgtggg ngccgcncca ggaagcttgc     360
tggggaaggt nctggggagc gttgccttgt tcatcccgac acctntttcg gnccctattg     420
gaagggattn attttttgcca tgt                                            443
```

<210> SEQ ID NO 77
<211> LENGTH: 394
<212> TYPE: DNA
<213> ORGANISM: Homo sapiens
<220> FEATURE:
<221> NAME/KEY: Unsure
<222> LOCATION: (1)..(1)
<223> OTHER INFORMATION: May be any nucleic acid

<400> SEQUENCE: 77

```
nttttttttt ttttgaaaaa attgtgaaaa aatttaaacc ccaggggact atccaagggg      60
aaaagtgaaa tatggaaaaa ttggcggtat gaccaatttg ggcattgcaa agagccttgc     120
agaattatga agcataaaag gaaattattg gcttttggag agttttcttt tctctcttct     180
tttttttgtaa tttcaatcta tatcagtagt ggaaaggtca tagcaaaata tggagaatcc     240
aaatggtaga tacaacctga tatcttgtgg aacaaggcat acaacagcaa agcaacacca     300
gtgaaaccaa ggacaccaaa cagtccccag agaactccag ctgtcatgag gtctcttcta     360
tagccatcag gtcctgagat ggagactggc actg                                 394
```

<210> SEQ ID NO 78
<211> LENGTH: 277

<210> SEQ ID NO 78
<211> LENGTH: 277
<212> TYPE: DNA
<213> ORGANISM: Homo sapiens

<400> SEQUENCE: 78

```
gtcatctttc agcctaaaaa ttagcaaaaa ctgttgaaac aaggcacagt ttttccccca    60
tatttgttac gtcgtggctc cagttaccaa aaaattttaa tgaaaacgtt aaacataaaa   120
atagaagttt gagattttaa aaagtgtata aaaagcccca caaaacttgt caacgttgtt   180
ccttattcta caaaatagca ccagtaagaa gagtaaaagg tgttaaaaac cattatgaca   240
gcatttctga aatgcagctt gtctgaattc ccgttct                            277
```

<210> SEQ ID NO 79
<211> LENGTH: 469
<212> TYPE: DNA
<213> ORGANISM: Homo sapiens

<400> SEQUENCE: 79

```
ttttagacaa atactgattt taattaaaca taaggtaaac tctaggcatc cgtcatcttt    60
cagcctaaaa attagcaaaa actgttgaaa catggcacag ttttttcccc atatttgtta   120
cgtcgtggct ccagttacaa aaaaatttta atgaaaacgt taaacataaa aatagaagtt   180
tgagatttta aaaagtgtat aaaaagcccc acaaaacttg tcaacgttgt tccttattct   240
acaaaatagc accagtaaga agagtaaaag gtgttaaaaa ccattatgac agcatttctg   300
aaatgcagct tgtctgaatt cccgttctcc ctaaaaacga cttcttatgg aataaaaaag   360
gattaaaaaa tctccaaagg gagcaccgag ctttgcagtt ttccctgtca tctctcagat   420
gtggggaagg tatgagaaat gtatgtctgt ccctgactgc tgtcactgc                469
```

<210> SEQ ID NO 80
<211> LENGTH: 206
<212> TYPE: DNA
<213> ORGANISM: Homo sapiens

<400> SEQUENCE: 80

```
gacaaatact gatccccccct acacataagg taaactctag gcatccgtca tctttcagcc    60
taaaaattag caaaactgt tgaaacaagg cacagttttt tccccatatt tgttacgtcg   120
tggctccagt tacgaaaaaa attttaatga aaacgttaaa cataaaaata gaagtttgag   180
attttaaaaa gtgtataaaa agcccc                                         206
```

<210> SEQ ID NO 81
<211> LENGTH: 391
<212> TYPE: DNA
<213> ORGANISM: Homo sapiens

<400> SEQUENCE: 81

```
ttttagacaa atactgattt taattaaaca taaggtaaac tctaggcatc cgtcatcttt    60
cagcctaaaa attagcaaaa actgttgaaa caaggcacag ttttttcccc atatttgtta   120
cgtcgtggct ccagttacaa aaaaatttt aatgaaaacg ttaaacataa aaatagaagt   180
ttgagatttt aaaagtgta taaaaagccc cacaaaactt gtcaacgttg ttccttattc   240
tacaaaatag caccagtaag aagagtaaaa ggtgttaaaa accattatga cagcatttct   300
gaaatgcagc ttgtctgaat tcccgttctc cctaaaaacg acttcttatg gaataaaaaa   360
ggattaaaaa atctccaaag ggagcaccga g                                  391
```

<210> SEQ ID NO 82

```
<211> LENGTH: 755
<212> TYPE: DNA
<213> ORGANISM: Homo sapiens
<220> FEATURE:
<221> NAME/KEY: Unsure
<222> LOCATION: (10)..(10)
<223> OTHER INFORMATION: May be any nucleic acid
<221> NAME/KEY: Unsure
<222> LOCATION: (19)..(19)
<223> OTHER INFORMATION: May be any nucleic acid
<221> NAME/KEY: Unsure
<222> LOCATION: (47)..(47)
<223> OTHER INFORMATION: May be any nucleic acid
<221> NAME/KEY: Unsure
<222> LOCATION: (117)..(117)
<223> OTHER INFORMATION: May be any nucleic acid
<221> NAME/KEY: Unsure
<222> LOCATION: (119)..(119)
<223> OTHER INFORMATION: May be any nucleic acid
<221> NAME/KEY: Unsure
<222> LOCATION: (134)..(134)
<223> OTHER INFORMATION: May be any nucleic acid
<221> NAME/KEY: Unsure
<222> LOCATION: (136)..(136)
<223> OTHER INFORMATION: May be any nucleic acid
<221> NAME/KEY: Unsure
<222> LOCATION: (138)..(139)
<223> OTHER INFORMATION: May be any nucleic acid
<221> NAME/KEY: Unsure
<222> LOCATION: (146)..(147)
<223> OTHER INFORMATION: May be any nucleic acid
<221> NAME/KEY: Unsure
<222> LOCATION: (149)..(149)
<223> OTHER INFORMATION: May be any nucleic acid
<221> NAME/KEY: Unsure
<222> LOCATION: (157)..(158)
<223> OTHER INFORMATION: May be any nucleic acid
<221> NAME/KEY: Unsure
<222> LOCATION: (160)..(160)
<223> OTHER INFORMATION: May be any nucleic acid
<221> NAME/KEY: Unsure
<222> LOCATION: (162)..(162)
<223> OTHER INFORMATION: May be any nucleic acid
<221> NAME/KEY: Unsure
<222> LOCATION: (164)..(164)
<223> OTHER INFORMATION: May be any nucleic acid
<221> NAME/KEY: Unsure
<222> LOCATION: (170)..(172)
<223> OTHER INFORMATION: May be any nucleic acid
<221> NAME/KEY: Unsure
<222> LOCATION: (176)..(178)
<223> OTHER INFORMATION: May be any nucleic acid
<221> NAME/KEY: Unsure
<222> LOCATION: (180)..(181)
<223> OTHER INFORMATION: May be any nucleic acid
<221> NAME/KEY: Unsure
<222> LOCATION: (186)..(186)
<223> OTHER INFORMATION: May be any nucleic acid
<221> NAME/KEY: Unsure
<222> LOCATION: (191)..(194)
<223> OTHER INFORMATION: May be any nucleic acid
<221> NAME/KEY: Unsure
<222> LOCATION: (199)..(199)
<223> OTHER INFORMATION: May be any nucleic acid
<221> NAME/KEY: Unsure
<222> LOCATION: (205)..(205)
<223> OTHER INFORMATION: May be any nucleic acid
<221> NAME/KEY: Unsure
<222> LOCATION: (215)..(215)
<223> OTHER INFORMATION: May be any nucleic acid
<221> NAME/KEY: Unsure
<222> LOCATION: (217)..(217)
<223> OTHER INFORMATION: May be any nucleic acid
<221> NAME/KEY: Unsure
<222> LOCATION: (219)..(220)
<223> OTHER INFORMATION: May be any nucleic acid
<221> NAME/KEY: Unsure
<222> LOCATION: (226)..(226)
<223> OTHER INFORMATION: May be any nucleic acid
```

-continued

```
<221> NAME/KEY: Unsure
<222> LOCATION: (231)..(231)
<223> OTHER INFORMATION: May be any nucleic acid
<221> NAME/KEY: Unsure
<222> LOCATION: (234)..(234)
<223> OTHER INFORMATION: May be any nucleic acid
<221> NAME/KEY: Unsure
<222> LOCATION: (237)..(237)
<223> OTHER INFORMATION: May be any nucleic acid
<221> NAME/KEY: Unsure
<222> LOCATION: (243)..(244)
<223> OTHER INFORMATION: May be any nucleic acid
<221> NAME/KEY: Unsure
<222> LOCATION: (257)..(257)
<223> OTHER INFORMATION: May be any nucleic acid
<221> NAME/KEY: Unsure
<222> LOCATION: (259)..(259)
<223> OTHER INFORMATION: May be any nucleic acid
<221> NAME/KEY: Unsure
<222> LOCATION: (275)..(275)
<223> OTHER INFORMATION: May be any nucleic acid
<221> NAME/KEY: Unsure
<222> LOCATION: (298)..(298)
<223> OTHER INFORMATION: May be any nucleic acid
<221> NAME/KEY: Unsure
<222> LOCATION: (301)..(301)
<223> OTHER INFORMATION: May be any nucleic acid
<221> NAME/KEY: Unsure
<222> LOCATION: (338)..(338)
<223> OTHER INFORMATION: May be any nucleic acid
<221> NAME/KEY: Unsure
<222> LOCATION: (374)..(374)
<223> OTHER INFORMATION: May be any nucleic acid
<221> NAME/KEY: Unsure
<222> LOCATION: (382)..(832)
<223> OTHER INFORMATION: May be any nucleic acid
<221> NAME/KEY: Unsure
<222> LOCATION: (416)..(416)
<223> OTHER INFORMATION: May be any nucleic acid
<221> NAME/KEY: Unsure
<222> LOCATION: (436)..(436)
<223> OTHER INFORMATION: May be any nucleic acid
<221> NAME/KEY: Unsure
<222> LOCATION: (481)..(481)
<223> OTHER INFORMATION: May be any nucleic acid
<221> NAME/KEY: Unsure
<222> LOCATION: (486)..(486)
<223> OTHER INFORMATION: May be any nucleic acid
<221> NAME/KEY: Unsure
<222> LOCATION: (498)..(498)
<223> OTHER INFORMATION: May be any nucleic acid
<221> NAME/KEY: Unsure
<222> LOCATION: (502)..(502)
<223> OTHER INFORMATION: May be any nucleic acid
<221> NAME/KEY: Unsure
<222> LOCATION: (504)..(504)
<223> OTHER INFORMATION: May be any nucleic acid
<221> NAME/KEY: Unsure
<222> LOCATION: (524)..(524)
<223> OTHER INFORMATION: May be any nucleic acid
<221> NAME/KEY: Unsure
<222> LOCATION: (528)..(528)
<223> OTHER INFORMATION: May be any nucleic acid
<221> NAME/KEY: Unsure
<222> LOCATION: (568)..(568)
<223> OTHER INFORMATION: May be any nucleic acid
<221> NAME/KEY: Unsure
<222> LOCATION: (572)..(572)
<223> OTHER INFORMATION: May be any nucleic acid
<221> NAME/KEY: Unsure
<222> LOCATION: (577)..(577)
<223> OTHER INFORMATION: May be any nucleic acid
<221> NAME/KEY: Unsure
<222> LOCATION: (579)..(579)
<223> OTHER INFORMATION: May be any nucleic acid
<221> NAME/KEY: Unsure
<222> LOCATION: (587)..(587)
<223> OTHER INFORMATION: May be any nucleic acid
<221> NAME/KEY: Unsure
```

```
<222> LOCATION: (596)..(596)
<223> OTHER INFORMATION: May be any nucleic acid
<221> NAME/KEY: Unsure
<222> LOCATION: (598)..(599)
<223> OTHER INFORMATION: May be any nucleic acid
<221> NAME/KEY: Unsure
<222> LOCATION: (615)..(615)
<223> OTHER INFORMATION: May be any nucleic acid
<221> NAME/KEY: Unsure
<222> LOCATION: (619)..(619)
<223> OTHER INFORMATION: May be any nucleic acid
<221> NAME/KEY: Unsure
<222> LOCATION: (624)..(624)
<223> OTHER INFORMATION: May be any nucleic acid
<221> NAME/KEY: Unsure
<222> LOCATION: (626)..(626)
<223> OTHER INFORMATION: May be any nucleic acid
<221> NAME/KEY: Unsure
<222> LOCATION: (628)..(628)
<223> OTHER INFORMATION: May be any nucleic acid
<221> NAME/KEY: Unsure
<222> LOCATION: (631)..(631)
<223> OTHER INFORMATION: May be any nucleic acid
<221> NAME/KEY: Unsure
<222> LOCATION: (638)..(638)
<223> OTHER INFORMATION: May be any nucleic acid
<221> NAME/KEY: Unsure
<222> LOCATION: (643)..(643)
<223> OTHER INFORMATION: May be any nucleic acid
<221> NAME/KEY: Unsure
<222> LOCATION: (655)..(655)
<223> OTHER INFORMATION: May be any nucleic acid
<221> NAME/KEY: Unsure
<222> LOCATION: (663)..(663)
<223> OTHER INFORMATION: May be any nucleic acid
<221> NAME/KEY: Unsure
<222> LOCATION: (666)..(666)
<223> OTHER INFORMATION: May be any nucleic acid
<221> NAME/KEY: Unsure
<222> LOCATION: (668)..(668)
<223> OTHER INFORMATION: May be any nucleic acid
<221> NAME/KEY: Unsure
<222> LOCATION: (701)..(701)
<223> OTHER INFORMATION: May be any nucleic acid
<221> NAME/KEY: Unsure
<222> LOCATION: (716)..(716)
<223> OTHER INFORMATION: May be any nucleic acid
<221> NAME/KEY: Unsure
<222> LOCATION: (739)..(739)
<223> OTHER INFORMATION: May be any nucleic acid
<221> NAME/KEY: Unsure
<222> LOCATION: (747)..(747)
<223> OTHER INFORMATION: May be any nucleic acid

<400> SEQUENCE: 82
tcttcgaagn cgagtcggnc tgtaccctca tacaggcctt tcctggntgg attcacattt      60
gagagatcgt tgcatgggct tccgccaatc accaagtcaa atgggcccca ttcttcnana     120
tttttctttg gggngngnnc ccccenngnc ccccccnngn tntnttttn nntttnnncn      180 ngtccncccg nnnngggtnc tcacncactt cagangngnn gggctntcct nccnttntgg     240
ccnnctcttt gcggatngnt aggctgtcgc gatgncatca aacaatgaca ggactcgnct     300
nggcgccttc gggctgcggg aatgggagga tctttggntt tcctgtgcac tacacagacg     360
tgtccaacat gggncgtggt gnccgccaga agcttgctgg ggaaggtcct tggagnggtg     420
tcttgtcaat cccganaacc tctttccggc cccccttgga aggggcttac ttctgggaat     480
ngttgnattt ggtcccangc cnangggccc caaaaggccc ccantttngg gggttgtttt     540
ttggaaagga ggcccaaggg accccccngg gnggggngnt tgtttcnccc ctgggnanng    600
```

-continued

```
ggaattcccc cccangggnc cccngntntt nttccccncc aantttttgg ggttngggt      660 tanaanancc cggggggtttc cccccaagg ccccccctct ntttgggttc aaaaangggg      720 ggggggaag gggccccnc cctgaanttt ttttc                                  755
```